(12) United States Patent
Gerwick et al.

(10) Patent No.: US 9,045,401 B2
(45) Date of Patent: Jun. 2, 2015

(54) METHODS FOR TREATING OR AMELIORATING A MELANOMA AND KILLING MELANOMA CELLS

(75) Inventors: William Gerwick, La Jolla, CA (US);
Wolfgang Wrasidlo, La Jolla, CA (US);
Dennis Carson, La Jolla, CA (US);
Dwayne Stupack, San Diego, CA (US);
Takashi Suyama, Albany, OR (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1032 days.

(21) Appl. No.: 12/600,930

(22) PCT Filed: May 21, 2008

(86) PCT No.: PCT/US2008/064402
§ 371 (c)(1),
(2), (4) Date: Jul. 8, 2010

(87) PCT Pub. No.: WO2008/144747
PCT Pub. Date: Nov. 27, 2008

(65) Prior Publication Data
US 2010/0266675 A1 Oct. 21, 2010

Related U.S. Application Data

(60) Provisional application No. 60/939,331, filed on May 21, 2007.

(51) Int. Cl.
*A61K 9/127* (2006.01)
*C07C 323/60* (2006.01)
*C07C 233/47* (2006.01)

(52) U.S. Cl.
CPC ............ *C07C 323/60* (2013.01); *C07C 233/47* (2013.01)

(58) Field of Classification Search
None
See application file for complete search history.

(56) References Cited

U.S. PATENT DOCUMENTS

2007/0082042 A1* 4/2007 Park et al. ............... 424/450

OTHER PUBLICATIONS

Nogle et al. Somocystinamide (Organic Letters 2002 vol. 4, No. 7 1095-1098.*
Mutation Reseach 4-80 481 (2001) 219 229.*
Kang, Young Jin, Written Opinion issued in PCT/US2008/064402, Dec. 10, 2008.
Mulhausen, Dorothee, International Preliminary Examination Report issued in PCT/US2008/064402, Nov. 24, 2009.
Nogle, "Somocystinamide A, A Novel Cytotoxic Disulfide Dimer from a Fijian Marine Cyanobacterial Mixed Assemblage," Organic Letters, 2002, vol. 4, No. 7, 1095-1098.
Manger et al., "Detection of Sodium Channel Toxins: Directed Cytotoxicity Assays of Purified Ciguatoxins, Brevetoxins, Saxitoxins, and Seafood Extracts," Journal of AOAC International, vol. 78, No. 2, 1995, pp. 521-527.

* cited by examiner

*Primary Examiner* — Snigdha Maewall
(74) *Attorney, Agent, or Firm* — Gregory P. Einhorn; Greer Burns & Crain LLP

(57) ABSTRACT

The invention provides novel compositions—lipopeptides and analogs, including somocystinamide A, and somocystinamide A variants and analogs, and pharmaceutical compositions, liposomes and nanoparticles comprising them, and methods of making and using them. In one embodiment, these lipopeptides and analogs are used to induce apoptosis in a cell, which can be a normal cell, a dysfunctional cell and/or a cancer (tumor) cell. In alternative embodiments, the compositions of the invention, including the lipopeptides and analogs of the invention, and the pharmaceutical compositions comprising them, are used to treat or ameliorate (including slowing the progression of) normal, dysfunctional (e.g., abnormally proliferating) and/or tumor associated blood vessels, including endothelial and/or capillary cell growth; including neovasculature related to (within, providing a blood supply to) a tumor.

20 Claims, 39 Drawing Sheets

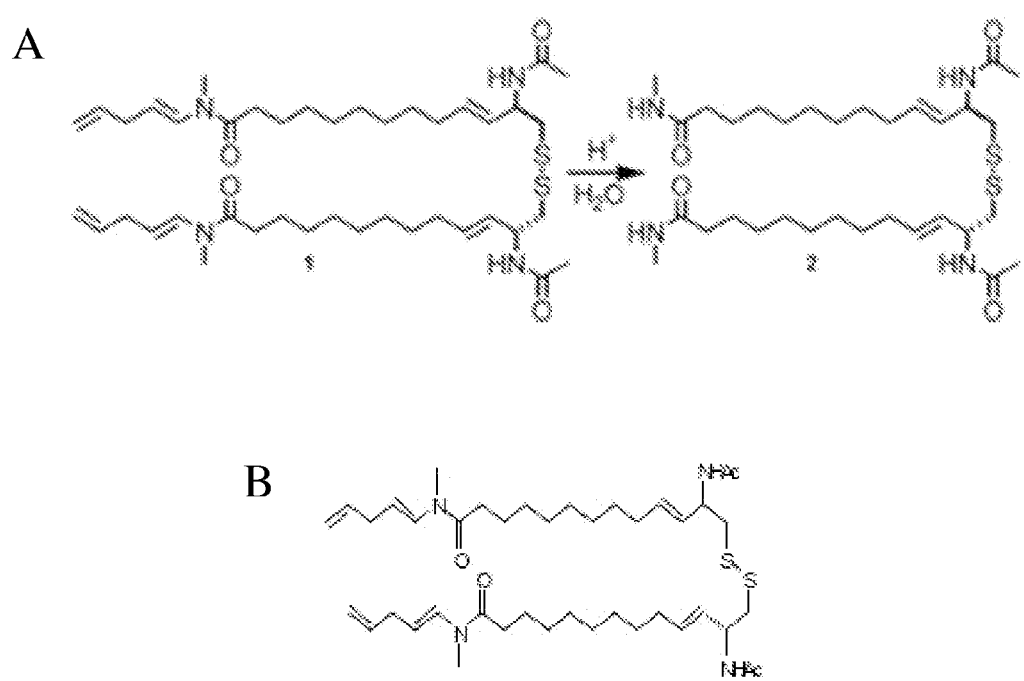
Figure 1 (A, B)

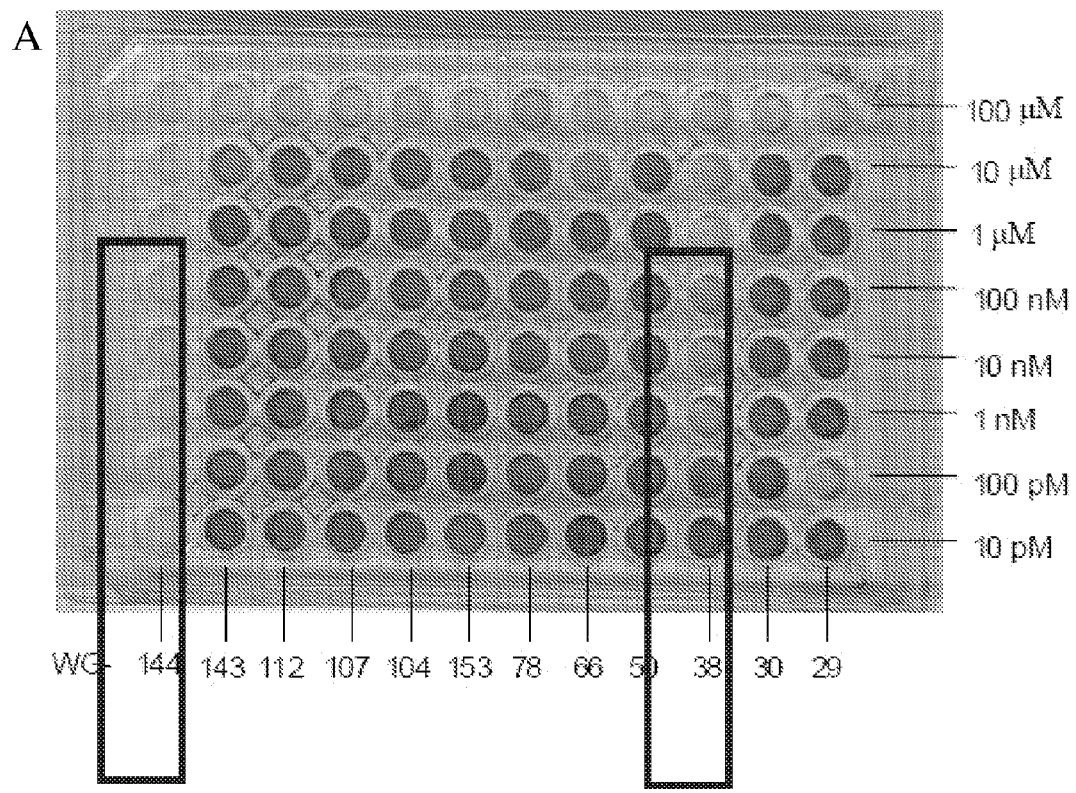
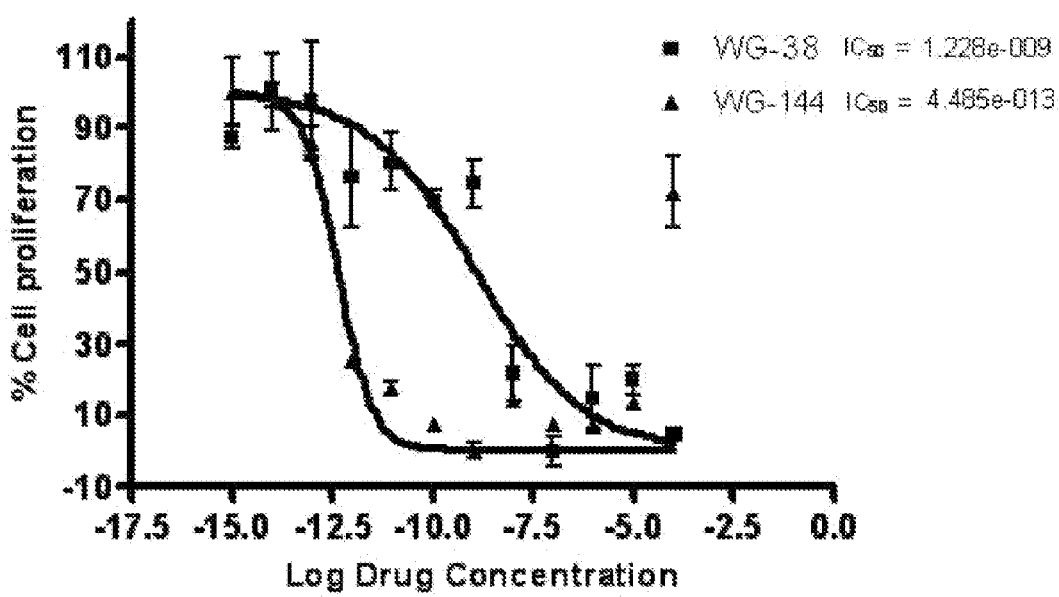
Figure 2 (A, B)

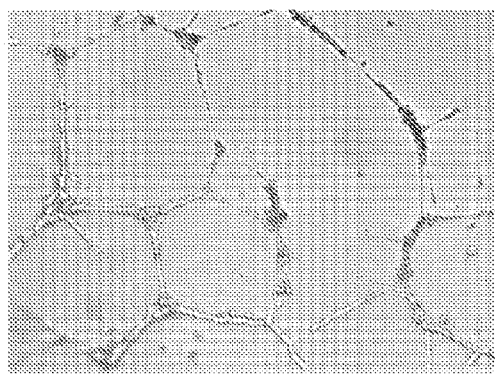 3A. Control (culture medium)
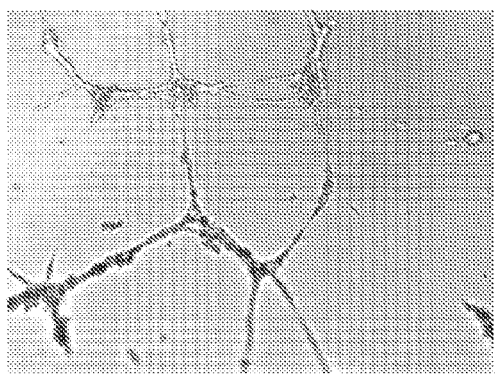 3B. WG-144 (1 pM)
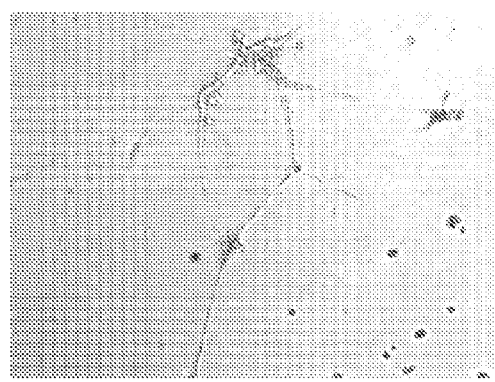 3C. WG-144 (100 pM)
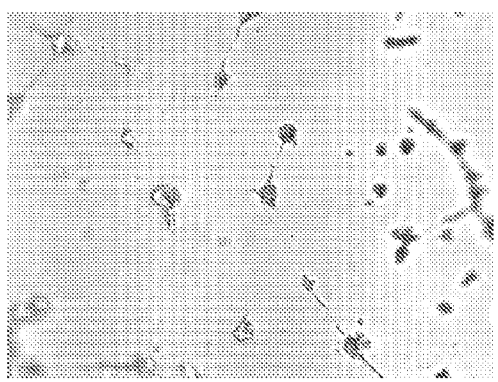 3D. WG-144 (10 nM)
Figure 3 (A, B, C, D)

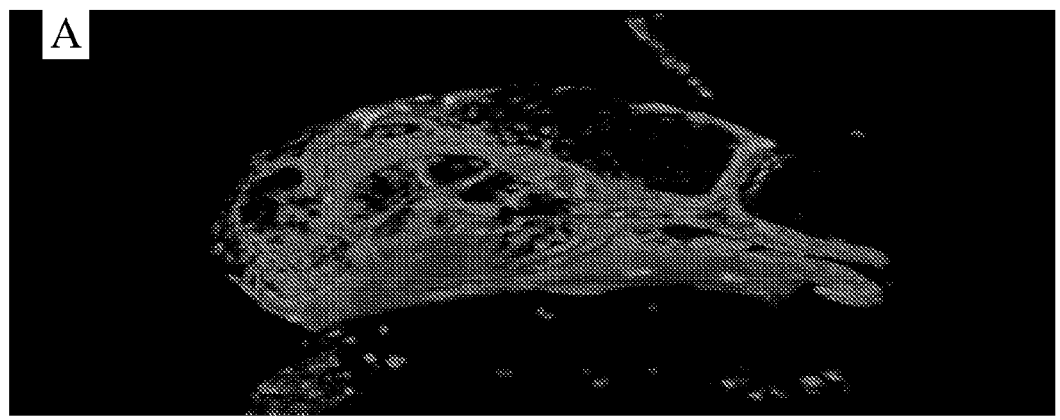
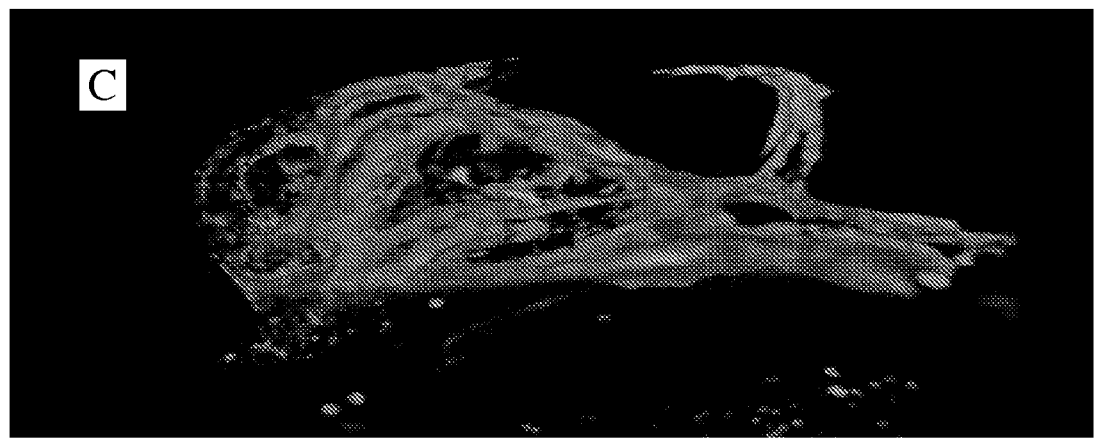
Figure 4 (A, B, C)

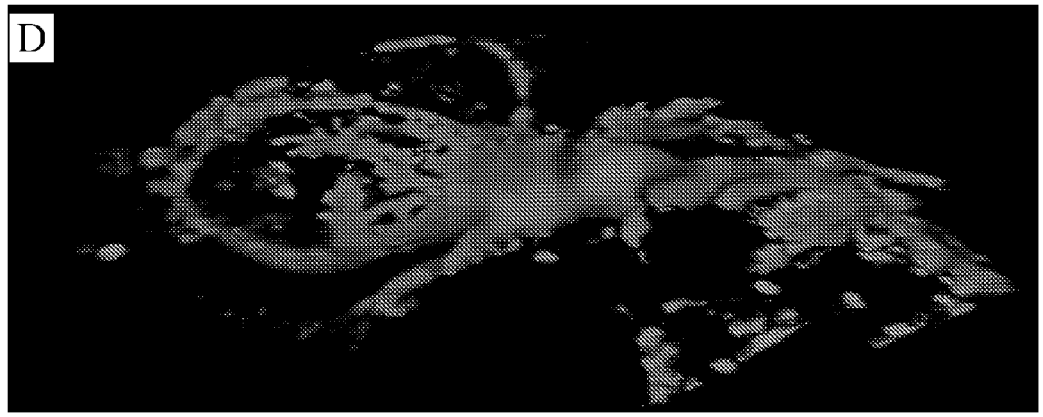
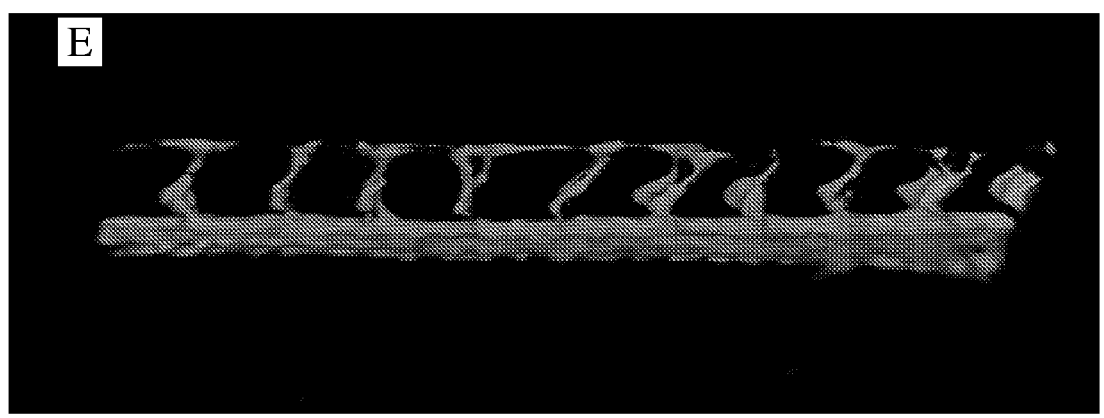
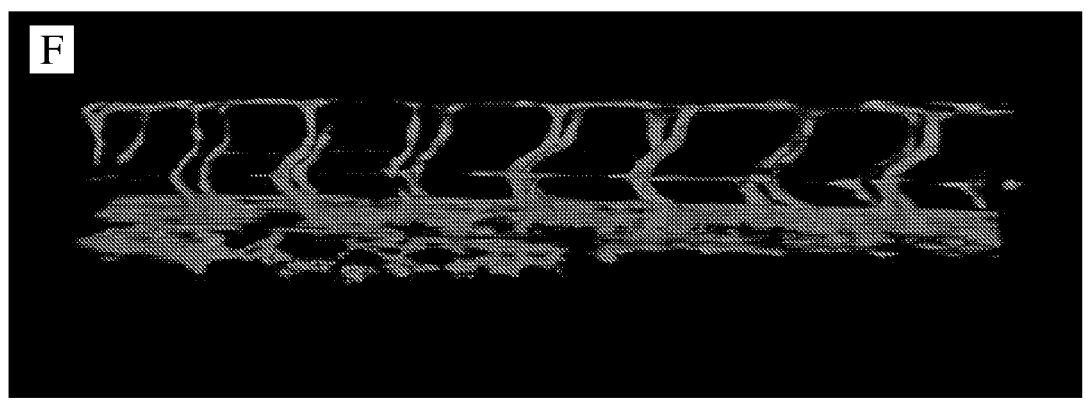
Figure 4 (D, E, F)

A 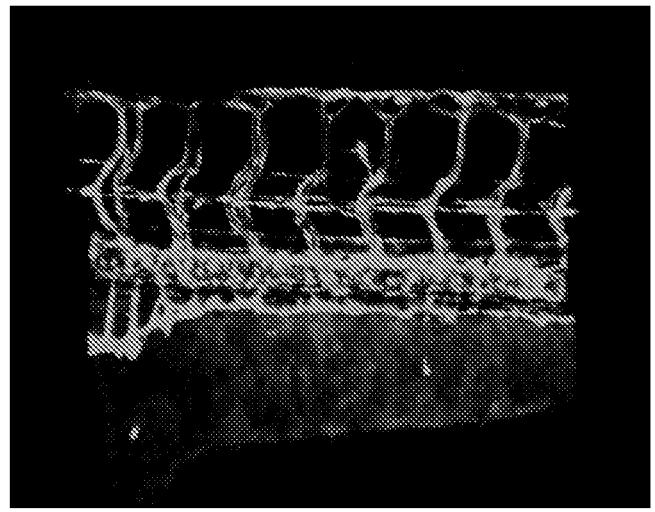
B 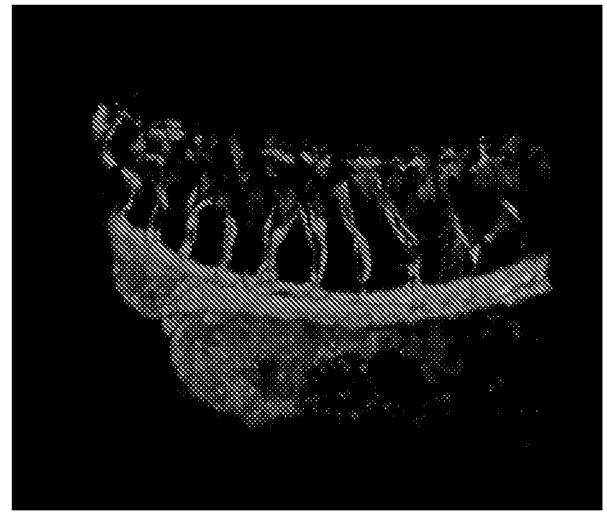
Figure 5 (A, B)

C
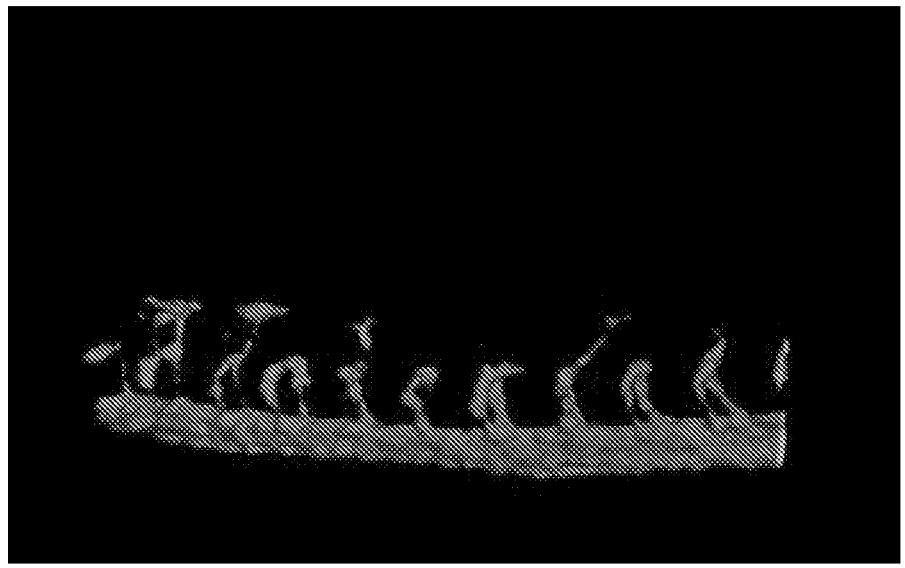
D
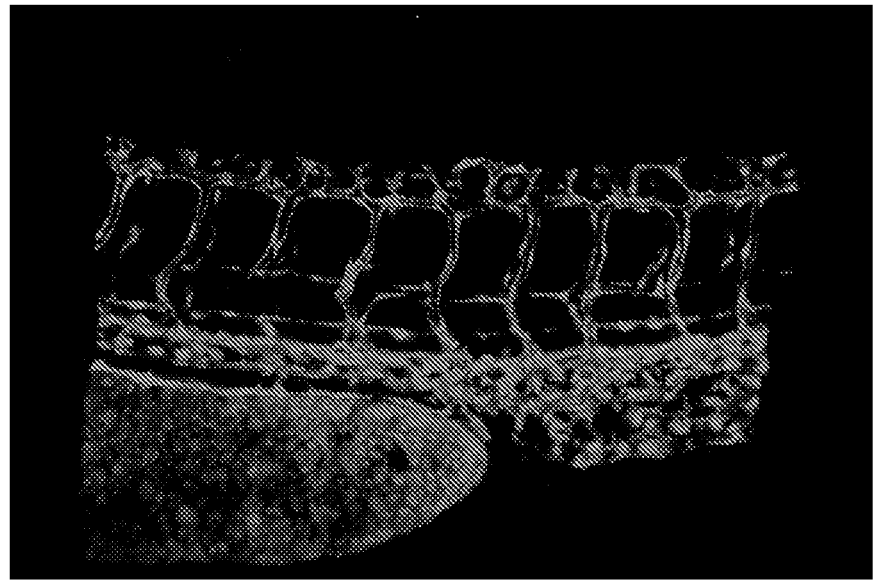
Figure 5 (C, D)

E
F
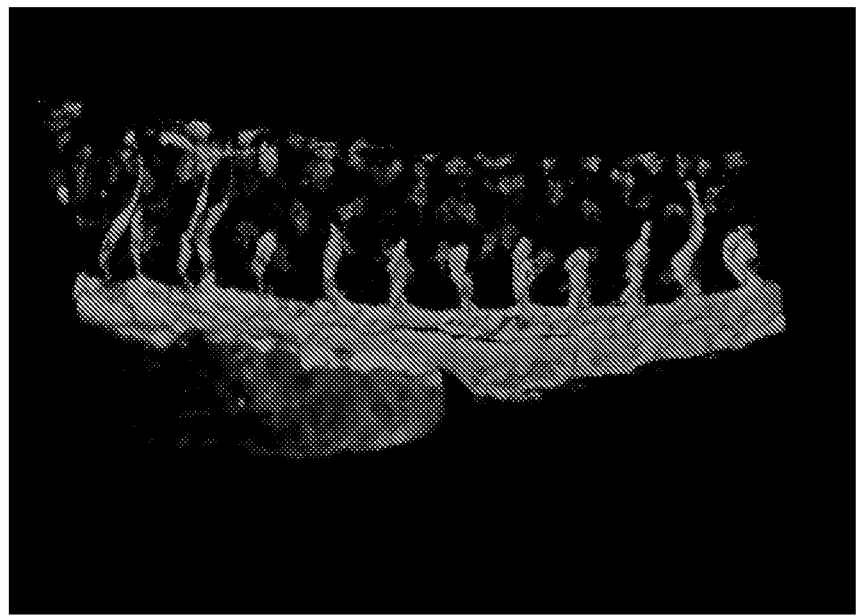
Figure 5 (E, F)

| Cell Line | IC$_{50}$ | |
|---|---|---|
| M21 Melanoma | 1.28 uM | MTT |
| PC3 prostate cancer | 0.97 uM | MTT |
| TJK304 | 0.83 uM | MTT |
| Molt-4 Tell leukemia | 0.60 uM | XTT |
| NB7 neuroblastoma | 0.81 uM | XTT |
| NB7 (caspase 8 positive) | 0.012 uM | XTT |
| A-549 Lung cancer | 0.046 uM | MTT |
| Pancreatic metastatic mouse carcinoma | 0.008 uM | XTT |
| HUVEC primary endothelial cells | 0.000004 uM | XTT |

Figure 6

WG-144 (Mol Log P = 10.3336)

Analoging Natural Compound for Drugability active natural compund
d= 2.07 Å ridgid linker analog
d= 2.10 Å flexible either glyco-lipid n = 8 for somocystinamide analog but can be varied between 4-22
p = 1 for somocystinamide but can vary from 1 - 12

| | A linker length | |
|---|---|---|
| 1 | 6.31 | Disulfide linker of natural product |
| 2 | 4.77 | simplest flexible, stable ether linkage |
| 3 | 5.01 | NHAc shielded ester linkage (may be esterase cleavable) |
| 4 | 5.93 | ethylene glycol type linkage with R groups for further analoging R1/R2 could be ring structure for inducing ridgidity |
| 5 | 5.51 | ideal flexible linker for phospholipid formation at R3 position |
| 6 | 4.67 | flexible hydrazide peptide like linker |
| 7 | 5.02 | ridgid oxazole linker made from 6 |

METHODS FOR TREATING OR AMELIORATING A MELANOMA AND KILLING MELANOMA CELLS

CROSS-REFERENCE TO RELATED APPLICATIONS

This United States utility patent application is the §371 national phase of PCT international patent application no. PCT/US2008/064402 having an international filing date of May 21, 2008, which claims benefit of priority to U.S. Provisional Patent Application Ser. No. 60/939,331, filed May 21, 2007. The aforementioned applications are expressly incorporated herein by reference in their entirety and for all purposes.

TECHNICAL FIELD

This invention generally relates to biochemistry, cell and tumor biology and medicine. The invention provides novel compositions—lipopeptides and analogs, including somocystinamide A and analogs, and pharmaceutical compositions comprising them, and methods of making and using them. In one embodiment, these lipopeptides and analogs are used to induce apoptosis in a cell, which can be a normal cell, a dysfunctional cell and/or a cancer (tumor) cell. In alternative embodiments, the compositions of the invention, including the lipopeptides and analogs of the invention, and the pharmaceutical compositions comprising them, are used to treat, prevent or ameliorate (including slowing the progression of) normal, dysfunctional (e.g., abnormally proliferating) and/or tumor associated blood vessels, including endothelial and/or capillary cell growth; including neovasculature related to (within, providing a blood supply to) hyperplastic tissue, a granuloma or a tumor. Accordingly, in alternative embodiments the compositions of the invention are used as antiangiogenic agents.

BACKGROUND

Massive efforts by the pharmaceutical industry to develop anticancer drugs via high throughput screening of large chemical libraries and structure based designs for targeted tumor therapy have so far yielded poor returns. The majority of anticancer drugs presently used in clinical practice are based on natural product chemistry. Thus the search for improved cancer therapeutics from natural resources with novel mechanisms of drug action has gained renewed relevance. A drug screening program of small molecules from marine environments has lead to the discovery of a family of secondary metabolites from cyanobacterium. These pluripotent lipopeptides exhibit nanomolar potencies against tumor cells.

An extract from a *Lyngbya majusculal Schizothrix* sp. mixed assemblage of marine cyanobacteria led to the discovery of somocystinamide A, an extraordinary disulfide dimer of mixed polyketide synthase (PKS) and nonribosomal peptide synthetase (NRPS), or "PKS/NRPS," biosynthetic origin. See, e.g., Nogle, et al. (2002) Org. Lett., 4(7):1095-1098. Somocystinamide A was shown to exhibit significant cytotoxicity against mouse neuro-2a neuroblastoma cells (with an $IC_{50}=1.4$ µg/mL); see e.g., Nogle (id).

Vascular Endothelial Growth Factor (VEGF) is a selective angiogenic growth factor that can stimulate endothelial cell mitogenesis. Human tumor biopsies exhibit enhanced expression of VEGF mRNAs by malignant cells and VEGF receptor mRNAs in adjacent endothelial cells.

SUMMARY

The invention provides novel compositions—lipopeptides and analogs, including somocystinamide A (ScA) and analogs, e.g. as disulfide-linked lipopeptide dimers, and pharmaceutical compositions comprising them, and methods of making and using them. In one embodiment, these lipopeptides and analogs are used to induce apoptosis in a cell, which can be a normal cell, a dysfunctional cell and/or a cancer (tumor) cell. In alternative embodiments, the compositions of the invention, including the lipopeptides and analogs of the invention, and the pharmaceutical compositions comprising them, are used to treat, prevent or ameliorate (including slowing the progression of) normal, dysfunctional (e.g., abnormally proliferating) and/or tumor associated blood vessels, including endothelial and/or capillary cell growth; including neovasculature related to (within, providing a blood supply to) hyperplastic tissue, a granuloma or a tumor. Accordingly, in alternative embodiments the invention provides compositions as antiangiogenic agents and methods for using them, e.g., as antitumor agents.

For example, the lipopeptides and analogs of the invention (including e.g., somocystinamide A and analogs, including disulfide-linked lipopeptide dimers), and the pharmaceutical compositions comprising them, can be used to stop, reverse or slow the growth and/or proliferation of normal, dysfunction and/or cancerous blood vessels, including endothelial and/or capillary cell growth and/or blood vessel formation, such as tumor-associated neovasculature. While the invention is not limited by any specific mechanism of action, in one aspect, the compositions and methods of the invention are used to induce apoptosis in a target cell, e.g., endothelial and/or capillary cell growth and/or blood vessel formation, such as tumor-associated neovasculature.

While the invention is not limited by any specific mechanism of action, in one aspect, the compositions and methods of the invention are used as antiangiogenic agents. The lipopeptides and analogs of the invention, and the pharmaceutical compositions comprising them, can be used to stop, reverse or slow the growth of a hyperplastic or dysfunctional cell, e.g., vascular cells, such as endothelial and/or capillary cells, such as cells involved in inflammation, psoriasis, endometriosis, diabetic retinopathy or wet-age related macular degeneration, benign prostate hyperplasia, for treating abnormal uterine bleeding (see, e.g., U.S. Pat. No. 6,440, 445), arterio-venous (AV) malformations, myocardial angiogenesis, plaque neovascularization, telangiectasia, hemophiliac joints, angio-fibroma, wound granulation, wound healing, telangiectasia psoriasis scleroderma, pyogenic granuloma, coronary collaterals, ischemic limb angiogenesis, rubeosis, arthritis, diabetic neovascularization, fractures, vasculogenesis, and hematopoiesis. Thus, the compositions and methods of the invention are used to inhibit, slow or reverse endothelial cell migration and to inhibit, slow or reverse angiogenesis. While the invention is not limited by any specific mechanism of action, in one aspect, the compositions and methods of the invention are used to induce apoptosis in a target cell, e.g., a hyperplastic or dysfunctional cell, e.g., vascular cells.

The lipopeptides and analogs of the invention, and the pharmaceutical compositions comprising them, can be useful to treat, reverse, prevent or ameliorate any vascular or endothelial cell proliferative condition, e.g., a skin condition such as psoriasis, or a hormone-dependent tumor or a hormone-influenced non-malignant disorder such as benign prostate hyperplasia (BPH) and endometriosis; or any disease or condition having an inflammatory component, e.g., an autoimmune disease such as rheumatoid arthritis, or an infectious disease; including treating, preventing or ameliorating any disease states associated with unwanted angiogenesis and/or cellular proliferation, such as diabetic retinopathy, wet-age related macular degeneration, neovascular glaucoma, rheumatoid arthritis, psoriasis or an arterio-venous (AV) malformation (e.g., a pulmonary AV malformation, such as Osler-Weber Syndrome).

The lipopeptides and analogs of the invention, and the pharmaceutical compositions comprising them, can be useful to treat, reverse, prevent (prophylaxis) or ameliorate any dysfunctional cell, or any abnormally (dysfunctional) dividing or metastasizing cell, e.g., a cancer or a tumor cell. Cancers that can be treated, prevented or ameliorated by using compositions of this invention include lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and/or any combination thereof.

Also provided herein are kits comprising the compositions and methods of this invention, and instructions for making, formulating and/or using them, e.g., for the therapeutic and/or prophylactic applications as described herein.

The invention provides compounds (a) having a formula as set forth in FIG. 1a-compound 2, FIG. 1b, FIG. 13, FIG. 19 (e.g., analog 1 and analog 2 structures), FIG. 20, FIG. 21, FIG. 25a or FIG. 25b, FIG. 26, or FIG. 27; or (b) the compound of (a), wherein the disulfide linking group is replaced by a rigid linker analog or a flexible ether analog, or a glycolipid moiety. The invention provides compounds having the following formula:

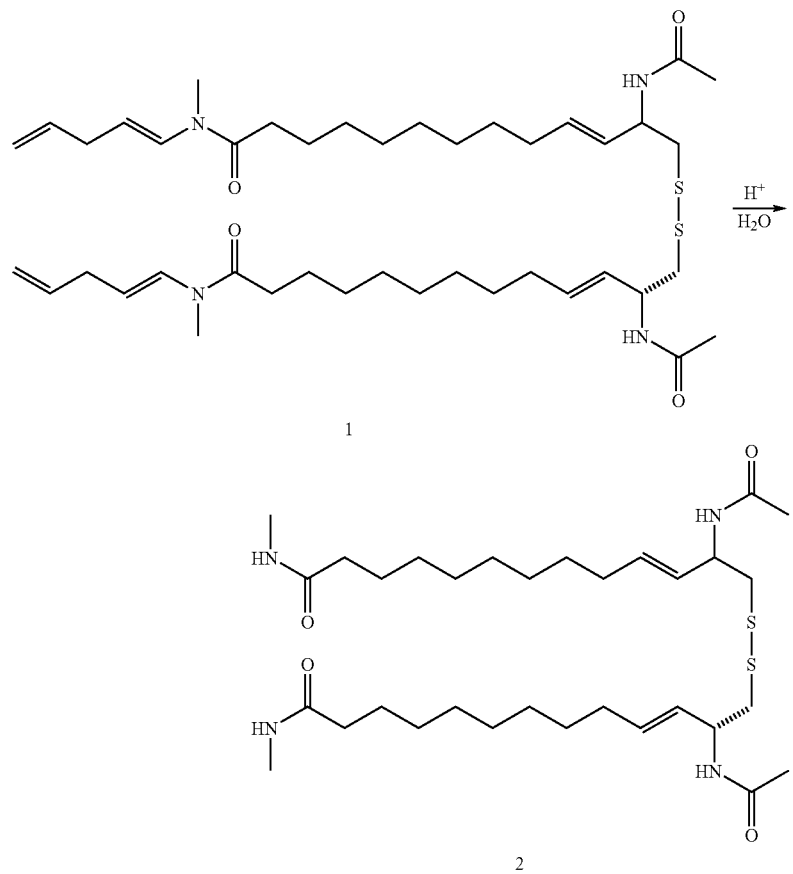

and variations of this compound, wherein the disulfide linking group is replaced by a rigid linker analog or a flexible ether analog, or a glycolipid moiety.

The invention provides somocystinamide A variants or analogues (i) having a formula as set forth in FIG. 1a-compound 2, FIG. 1b, FIG. 13, FIG. 19 (e.g., analog 1 and analog 2 structures), FIG. 20, FIG. 21, FIG. 25a or FIG. 25b, FIG. 26, or FIG. 27; or, (ii) having a formula of somocystinamide A, wherein (a) one or both of the acetate groups are replaced by an $R_1$ group independently selected from the group consisting of hydrogen, halo, hydroxy (—OH), thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—$NO_2$), alkoxy, haloalkoxy, thioalkoxy, alkanoyl, haloalkanoyl and carbonyloxy; or, (b) any one of the acetate units is substituted with an $R_1$ group independently selected from the group consisting of hydrogen, halo, hydroxy (—OH), thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—$NO_2$), alkoxy, haloalkoxy, thioalkoxy, alkanoyl, haloalkanoyl and carbonyloxy; or (iii) having a formula of (i) or (ii), wherein the disulfide linking group is replaced by a rigid linker analog or a flexible ether analog, or a glycolipid moiety; or (iv) having a formula of (i), (ii) or (iii), in the form of a disulfide-linked lipopeptide dimer.

The invention provides methods for making somocystinamide A, or an analogue or variant thereof, comprising:

(i) the steps of: (a) an L-cysteine is ketide extended with one, two, three, four, five, six, seven, eight, nine or ten acetate units; (b) followed by linkage of an N-methyl glycine moiety; (c) then further modified by extension with one, two, three, four, five, six, seven, eight, nine or ten additional acetates; and (d) decarboxylation to produce a terminal olefin; wherein optionally the method further comprises the step (e) dimerization to complete the synthesis, or optionally the disulfide linking group is replaced by a rigid linker analog or a flexible ether analog, or a glycolipid moiety; or (ii) a method as illustrated in FIG. 19, FIG. 20, FIG. 21, FIG. 25a or FIG. 25b, or FIG. 27 or a combination thereof; or (iii) a combination of (i) and (ii); or (iv) any of the methods of (i), (ii) or (iii), wherein the product is in the form of a disulfide-linked lipopeptide dimer.

In one embodiment, the invention provides methods comprising the steps of: (a) an L-cysteine is ketide extended with five (5) malonyl CoA derived acetate units; (b) followed by linkage of an N-methyl glycine moiety; (c) then further modified by extension with two additional acetates; (d) decarboxylation to produce a terminal olefin; and, (e) dimerization to complete the synthesis. In one embodiment, the invention provides methods wherein one or both of the acetate groups are replaced by an $R_1$ group independently selected from the group consisting of hydrogen, halo, hydroxy (—OH), thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—$NO_2$), alkoxy, haloalkoxy, thioalkoxy, alkanoyl, haloalkanoyl and carbonyloxy. In one embodiment, the invention provides methods wherein any one of the malonyl CoA derived acetate units is substituted with an $R_1$ group independently selected from the group consisting of hydrogen, halo, hydroxy (—OH), thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—$NO_2$), alkoxy, haloalkoxy, thioalkoxy, alkanoyl, haloalkanoyl and carbonyloxy.

In one aspect, the term "alkyl" includes straight-chain, branched-chain and cyclic monovalent hydrocarbyl radicals, and combinations of these, which contain only C and H when they are unsubstituted. Alkyl groups may be optionally unsaturated, such as in alkenyl or alkynyl groups. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as C1-C10 or as C1-10 or as $C_{1-10}$.

In one aspect, "alkenyl" and "alkynyl" groups are defined similarly to alkyl groups, and include straight-chain, branched-chain and cyclic monovalent hydrocarbyl radicals, and combinations of these, which contain only C and H when they are unsubstituted. However, alkenyl groups contain one or more carbon-carbon double bonds, and alkynyl groups contain one or more carbon-carbon triple bonds.

In alternative aspects, the alkyl, alkenyl and alkynyl substituents of the invention contain 1-8C (alkyl) or 2-8C (alkenyl or alkynyl). In alternative aspects, they contain 1-4C (alkyl) or 2-4C (alkenyl or alkynyl).

Alkyl, alkenyl and alkynyl groups are often substituted to the extent that such substitution makes sense chemically. In alternative aspects, substituents include, but are not limited to, halo, =O, —CN, —OR', —SR', —S(O)R', —$SO_2$R', —COOR', —C(O)$NR'_2$, —$NR'_2$ and —NHC(=NH)$NH_2$, where each R' independently represents H, C1-C4 alkyl or C5-C12 arylalkyl, or a heteroform of one of these.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue. When heteroatoms (typically N, O and S) are allowed to replace carbon atoms of an alkyl, alkenyl or alkynyl group, as in heteroalkyl groups, the numbers describing the group, though still written as e.g. C1-C6, represent the sum of the number of carbon atoms in the group plus the number of such heteroatoms that are included as replacements for carbon atoms in the ring or chain being described. Such heteroalkyl groups may be optionally substituted with the same substituents as alkyl groups.

Where such groups contain N, the nitrogen atom may be present as NH or it may be substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than two contiguous heteroatoms as part of the heteroalkyl chain, although an oxo group may be present on N or S as in a nitro or sulfonyl group. Thus —C(O)$NH_2$ can be a C2 heteroalkyl group substituted with =O; and —$SO_2$NH— can be a C2 heteroalkylene, where S replaces one carbon, N replaces one carbon, and S is substituted with two =O groups.

While "alkyl" in one aspect includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the base molecule through an alkyl linker. For example, cyclohexylalanine (Cha) comprises a cycloalkylalkyl substituent. Similarly, "heterocyclyl" may be used to describe a non-aromatic cyclic group that contains at least one heteroatom as a ring member and that is connected to the molecule via a ring atom of the cyclic group, which may be C or N; and "hetero-cyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. Where an alkyl group is substituted with an aryl or heteroaryl group, it is referred to as an arylalkyl or heteroarylalkyl substituent.

In one aspect, an "aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like.

Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the ring systems contain 5-12 ring member atoms. In alternative aspects, the monocyclic heteroaryl groups contain 5-6 ring members, and the bicyclic heteroaryls contain 8-10 ring members.

Aryl and heteroaryl moieties may be substituted with a variety of substituents which are known in the art. In alternative aspects, substituents include, but are not limited to, halo, C1-C8 alkyl, —$NO_2$, —CN, —OR', —SR', —COOR', —C(O)$NR'_2$, and —$NR'_2$, where each R' independently represents H, C1-C4 alkyl or C5-C12 arylalkyl, or a heteroform of one of these.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moieties. "Heteroarylalkyl" refers to a moiety comprising an aryl group that is attached through a linking group, and differs from "arylalkyl" in that at least one ring atom of the aryl moiety or one atom in the linking group is a heteroatom selected from N, O and S.

An aryl or heteroaryl ring in an arylalkyl or heteroarylalkyl group may be optionally substituted on the aromatic portion with the same substituents described above for aryl groups. In alternative embodiments, an arylalkyl group includes a phenyl ring and a heteroarylalkyl group includes a C5-C6 monocyclic or C8-C10 fused bicyclic heteroaromatic ring, each of which may be optionally substituted with the groups defined above for aryl groups and a C1-C4 alkylene that is unsubstituted or is substituted with one or two C1-C4 alkyl groups, where the alkyl groups can optionally cyclize to form a ring, and wherein the alkyl or heteroalkyl groups may be optionally fluorinated. In certain embodiments, the arylalkyl or heteroarylalkyl ring comprises a phenol or an indole ring. In alternative aspects, substituents on phenyl include OH, C1-C4 alkoxy, and halo.

"Arylalkyl" and "heteroarylalkyl" groups are described by the total number of carbon atoms in the ring and alkylene or similar linker. Thus a benzyl group is a C7-arylalkyl group, and phenethyl is a C8-arylalkyl group.

"Alkylene" in one aspect refers to a divalent hydrocarbyl group; because it is divalent, it can link two other groups together. Typically it refers to —$(CH_2)_n$— where n is 1-8, or n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —$(CH_2)_3$—, i.e., the specified length represents the number of atoms linking the attachment points rather than the total number of atoms in the hydrocarbyl group: —C(Me)$_2$- would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene may contain one or more double or triple bonds.

"Heteroalkylene" in one aspect is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

In one aspect, an "aminoalkyl" group refers to a C1-C6 alkyl group that is substituted with at least one amine group having the formula —NR2, where each R is independently H, C1-C8 alkyl, C5-C12 aryl and C5-C12 arylalkyl, or a heteroform of one of these. Such aminoalkyl groups may be optionally substituted on the alkyl portion with one or more other groups suitable as substituents for an alkyl group. In some embodiments, the aminoalkyl substituent is a 1-aminoalkyl group such as a 1-aminomethyl, 1-aminoethyl, 1-aminopropyl or 1-aminobutyl group. In certain embodiments, the aminoalkyl group may comprise a protected amine. One of skill in the art would appreciate that appropriate amine protecting groups may vary depending on the functionality present in the particular monomer. Suitably protected amines may include, for example, carbamates (e.g. tert-butoxycarbonyl, benzyloxycarbonyl, fluorenylmethyloxy-carbonyl, allyloxycarbonyl or (trialkylsilyl)ethoxycarbonyl), carboxamides (e.g. formyl, acyl or trifluoroacetyl), sulfonamides, phthalimides, Schiff base derivatives, and the like. In certain embodiments, an aminoalkyl group may be coupled through an alkylene or heteroalkylene linker to a group such as biotin, or a fluorophore-containing group, such as rhodamine, and such compounds may be useful for screening or mechanistic studies.

"Heteroform" in one aspect refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" in one aspect indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo", in one aspect includes fluoro, chloro, bromo and iodo. Fluoro and chloro can be used.

"Amino" in one aspect refers to $NR'_2$ wherein each R' is independently H, or is an alkyl, alkenyl, alkynyl, acyl, aryl, or arylalkyl group or a heteroform of one of these groups, as defined above, each of which may be optionally substituted with the substituents described herein as suitable for the corresponding type of group. In certain embodiments, the two R' groups on one nitrogen atom may be linked together to form an azacyclic ring.

In one aspect, an 'azacyclic' group refers to a heterocyclic group containing at least one nitrogen atom as a ring atom, wherein the group is attached to the base molecule through a nitrogen atom of the azacyclic group. Typically azacyclic groups are 3-8 membered monocyclic rings or 8-12 membered bicyclic fused ring systems, and may be saturated, unsaturated or aromatic and may contain a total of 1-3 heteroatoms independently selected from N, O and S as ring members. In certain embodiments, an azacyclic ring may comprise a nitrogen-containing ring fused to a phenyl ring. For example, the unnatural amino acid "Tic" comprises a tetrahydroisoquinoline ring, which represents a 10-membered fused bicyclic azacyclic group.

The invention provides compositions made by any of the biosynthetic or synthetic methods described herein, and equivalents thereof, and pharmaceutical compositions comprising these compounds.

The invention provides pharmaceutical compositions comprising somocystinamide A, or a variant or analog thereof, wherein the somocystinamide A, or variant or analog, comprises any compound of this invention, or a compound made by any of the biosynthetic or synthetic methods of this invention.

The invention provides liposomes comprising somocystinamide A, or a variant or analog thereof, wherein the somocystinamide A, or variant or analog comprises any compound of this invention, or a compound made by any of the biosynthetic or synthetic methods of this invention.

The invention provides nanoparticles comprising somocystinamide A, or a variant or analog thereof, wherein the somocystinamide A, or variant or analog comprises any compound of this invention, or a compound made by any of the biosynthetic or synthetic methods of this invention.

The invention provides use of somocystinamide A (ScA) or a variant or analog thereof, for the manufacture of a medicament for the treatment, prevent or amelioration of diseases or conditions associated with dysfunctional angiogenesis and/or abnormally proliferating blood vessels, wherein the somocystinamide A variant or analog comprises any compound of this invention, or a compound made by any of the biosynthetic or synthetic methods of this invention. In alternative embodiments, the blood vessels treated or ameliorated by the medicament comprise endothelial or capillary cells, and endothelial and/or capillary cell growth and/or viability is slowed, reversed or inhibited; or, the diseases or conditions treated or ameliorated by the medicament comprises an inflammatory component; or, the diseases or conditions treated or ameliorated by the medicament is psoriasis, endometriosis, diabetic retinopathy, wet-age related macular degeneration or abnormal uterine bleeding; or, the medicament treats or ameliorates dysfunctional angiogenesis and/or abnormally proliferating blood vessels, or abnormal endothelial or capillary cells in a granuloma, a retinal tissue, a retinal pigment epithelium, an endometrial tissue or a synovial tissue; or, the medicament treats or ameliorates a pathological angiogenesis in diabetic retinopathy, rheumatoid arthritis, choroidal neovascularization, pyogenic granuloma, endometriosis, pulmonary edema, female reproductive cycling disorders or pulmonary tuberculosis; or the medicament treats, prevents or ameliorates psoriasis, benign prostate hyperplasia (BPH) and endometriosis, a disease or condition having an inflammatory component, an autoimmune disease, a rheumatoid arthritis, an infectious disease, a diabetic retinopathy, wet-age related macular degeneration, neovascular glaucoma, rheumatoid arthritis and/or psoriasis; or the medicament treats, prevents or ameliorates arterio-venous (AV) malformation formation, a pulmonary AV malformation, Osler-Weber Syndrome, myocardial angiogenesis, plaque neovascularization, telangiectasia, hemophiliac joints, angiofibroma, wound granulation, wound healing, telangiectasia psoriasis scleroderma, pyogenic granuloma, coronary collaterals, ischemic limb angiogenesis, rubeosis, arthritis, diabetic neovascularization, fractures or any vasculogenesis; or the blood vessels or ameliorated treated by the medicament comprise neovasculature related to (within, or providing a blood supply to) a tumor, and neovasculature cell growth is slowed, reversed or inhibited; or the blood vessels or ameliorated treated by the medicament comprise neovasculature related to (within, or providing a blood supply to) a lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma or pituitary adenoma, and any combination thereof.

The invention provides methods for treating, preventing or ameliorating a disease or condition associated with dysfunctional angiogenesis and/or abnormally proliferating blood vessels comprising use of somocystinamide A, or a variant or analog thereof, wherein the somocystinamide A variant or analog comprises any compound of this invention, or a compound made by any of the biosynthetic or synthetic methods of this invention, or any formulation of the invention, or any pharmaceutical composition of the invention, or any liposome of the invention, or any nanoparticle of the invention. In alternative embodiments, the blood vessels treated or ameliorated by the medicament comprise endothelial or capillary cells, and endothelial and/or capillary cell growth and/or viability is slowed, reversed or inhibited; or the diseases or conditions treated or ameliorated by the medicament comprises an inflammatory component; or the diseases or conditions treated or ameliorated by the medicament is psoriasis, endometriosis, diabetic retinopathy, wet-age related macular degeneration or abnormal uterine bleeding; or the medicament treats or ameliorates dysfunctional angiogenesis and/or abnormally proliferating blood vessels, or abnormal endothelial or capillary cells in a granuloma, a retinal tissue, a retinal pigment epithelium, an endometrial tissue or a synovial tissue; or the medicament treats or ameliorates a pathological angiogenesis in diabetic retinopathy, rheumatoid arthritis, choroidal neovascularization, pyogenic granuloma, endometriosis, pulmonary edema, female reproductive cycling disorders or pulmonary tuberculosis; or the medicament treats, prevents or ameliorates psoriasis, benign prostate hyperplasia (BPH) and endometriosis, a disease or condition having an inflammatory component, an autoimmune disease, a rheumatoid arthritis, an infectious disease, a diabetic retinopathy, wet-age related macular degeneration, neovascular glaucoma, rheumatoid arthritis and/or psoriasis; or the medicament treats, prevents or ameliorates arterio-venous (AV) malformation formation, a pulmonary AV malformation, Osler-Weber Syndrome, myocardial angiogenesis, plaque neovascularization, telangiectasia, hemophiliac joints, angiofibroma, wound granulation, wound healing, telangiectasia psoriasis scleroderma, pyogenic granuloma, coronary collaterals, ischemic limb angiogenesis, rubeosis, arthritis, diabetic neovascularization, fractures or any vasculogenesis; or the blood vessels or ameliorated treated by the medicament comprise neovasculature related to (within, or providing a blood supply to) a tumor, and neovasculature cell growth is slowed, reversed or inhibited; or the blood vessels or ameliorated treated by the medicament comprise neovasculature related to (within, or providing a blood supply to) a lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma or pituitary adenoma, and any combination thereof.

The invention provides methods for inducing apoptosis in a cell comprising contacting the cell with a somocystinamide A variant or analog thereof, wherein the somocystinamide A variant or analog comprises any compound of this invention, or a compound made by any of the biosynthetic or synthetic methods of this invention, or any formulation of the invention, or any pharmaceutical composition of the invention, or any liposome of the invention, or any nanoparticle of the invention.

The invention provides methods for killing a cancer cell comprising contacting the cancer cell with a somocystinamide A variant or analog thereof, wherein the somocystinamide A variant or analog comprises any compound of this invention, or a compound made by any of the biosynthetic or synthetic methods of this invention, or any formulation of the invention, or any pharmaceutical composition of the invention, or any liposome of the invention, or any nanoparticle of the invention. In one aspect, the cancer is a lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma or pituitary adenoma, and/or any combination thereof.

The invention provides methods for killing an endothelial or neovascular cell comprising contacting the cell with a somocystinamide A, or a somocystinamide A variant or analog thereof, wherein the somocystinamide A variant or analog comprises any compound of this invention, or a compound made by any of the biosynthetic or synthetic methods of this invention, or any formulation of the invention, or any pharmaceutical composition of the invention, or any liposome of the invention, or any nanoparticle of the invention.

The invention provides methods for interacting with one or more death inducing signaling complex (DISC) molecules at a specified orientation in a cell membrane to induce apoptosis, comprising contacting the cell with a somocystinamide A, or a somocystinamide A variant or analog thereof, wherein the somocystinamide A variant or analog comprises any compound of this invention, or a compound made by any of the biosynthetic or synthetic methods of this invention, or any formulation of the invention, or any pharmaceutical composition of the invention, or any liposome of the invention, or any nanoparticle of the invention. In one aspect, the cell membrane is a cancer cell membrane, e.g., from or derived from a lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma or pituitary adenoma, and/or any combination thereof.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

The patent or application file contains at least one drawing executed in color. Copies of this patent or patent application publication with color drawing(s) will be provided by the Office upon request and payment of the necessary fee.

FIG. 1a, illustrates how somocystinamide A (compound 1) is highly acid-sensitive, rapidly and completely converting to a characterizable derivative (compound 2 in the figure) composition of this invention, as described in detail in Example 1, below. FIG. 1b is an exemplary composition of this invention, as described in detail in Example 1, below.

FIG. 2A illustrates a microtiter plate 72 hour (h) XTT assay for Huvec cell proliferation, showing serial dilutions (as set forth in the figure) of structurally diverse marine natural compounds, as described in detail in Example 1, below. FIG. 2B graphically illustrates the data for this study, as described in detail in Example 1, below.

FIGS. 3A to D illustrate photomicrographs demonstrating that somocystinamide A (ScA) at various concentrations; with control (no ScA) illustrated in FIG. 3A, and at 1 pM (FIG. 3B), 100 pM (FIG. 3C) and 10 nM (FIG. 3D), inhibits tube formation of HUVEC/matrigel, as described in detail in Example 1, below.

FIG. 4 illustrates confocal microscopy images of zebrafish expressing transgenic green fluorescent protein (GFP) in their endothelial cells, with 300 nM of somocystinamide A (ScA, designed "WG-144") and without ScA (control); showing expression of transgenic GFP in their endothelial cells after 12 hours (h) and 24 h in the brain, intersegmental vesicles and dorsal aorta, as indicated in the figure, as described in detail in Example 1, below. In summary, FIG. 4A (top) and 4B (lower) illustrate brain sections controls at 12 and 24 hours, respectively; FIG. 4C (top) and 4D (lower) illustrate brain sections of experiment with 300 nM of somocystinamide A (ScA, designed "WG-144") at 12 and 24 hours, respectively; FIG. 4E (top) and 4F (lower) illustrate intersegmental vesicles and dorsal aorta section controls at 12 and 24 hours, respectively; FIG. 4G (top) and 4H (lower) illustrate intersegmental vesicles and dorsal aorta sections of experiment with 300 nM of somocystinamide A (ScA, designed "WG-144") at 12 and 24 hours, respectively. In the confocal microscopy image of the intersegmental vesicles and dorsal aorta sections, the intersegmental vesicles are the structures of the top row of the depicted section, and the dorsal aorta are the structures of the bottom row of the depicted section.

FIG. 5 illustrates confocal microscopy images of the zebrafish expressing transgenic GFP in their endothelial cells, with a dose-response study of somocystinamide A (ScA): control is no ScA, and at 0.30 μM, 3.0 μM, 0.16 μM, 1.6 μM, and 0.08 μM ScA, as described in detail in Example 1, below. In summary, FIG. 5A left side image depicts the control sample; FIG. 5B right side image depicts the 0.30 μM ScA sample; FIG. 5C left side image depicts the 3.0 μM ScA sample; FIG. 5D right side image depicts the 0.16 μM ScA sample; FIG. 5E left side image depicts the 1.6 μM ScA sample; FIG. 5F right side image depicts the 0.08 μM ScA sample.

FIG. 6 is a chart summary of cell proliferation assays of somocystinamide A (ScA), demonstrating the anti-proliferative effect of somocystinamide A on M21 melanoma cells ($IC_{50}$ of 1.28 μM), PC3 prostate cancer cells ($IC_{50}$ of 0.97 μM), TJK304 cells ($IC_{50}$ of 0.83 μM), Molt-4 T cell leukemia cells ($IC_{50}$ of 0.60 μM), NB7 neuroblastoma cells ($IC_{50}$ of 0.81 μM), NB7 caspase 8 positive cells ($IC_{50}$ of 0.012 μM), A-549 lung cancer cells ($IC_{50}$ of 0.046 μM), pancreatic metastatic mouse carcinoma cells ($IC_{50}$ of 0.008 μM), and HUVEC primary endothelial cells ($IC_{50}$ of 0.000004 μM), as described in detail in Example 1, below.

FIG. 26 illustrates alternative exemplary compounds of this invention having, e.g., different linkers, including different structure, which can be used for the further synthesis of new analogs, as described in detail in Example 5, below.

FIG. 29(A) graphically illustrates data showing cell viability assessed by XTT assay where ScA was mixed to form liposomes and ScA completely partitioned into the lipid nanosomes, then cells were cultured with "free" ScA added in DMSO diluent or with ScA incorporated into nanosomes, and cell viability assessed by XTT assay; FIG. 29B and FIG. 29C illustrates images of A549 cells stained with anti-ceramide (red Channel) DAPI (blue channel) and anti-caspase 8 (green channel) 30 minutes after treatment with 300 nM arachidonic acid, a control lipid, FIG. 29(B) or 300 nM ScA FIG. 29(C), colocalization of the green and red channels is shown by the merge (yellow signal); FIG. 29(D) schematically illustrates a limited structure-function analysis of the required elements for ScA (shown at left of figure), as described in detail in Example 7, below.

FIG. 30(A) graphically illustrates data showing the results of an XTT assay, where human endothelial cells were incubated with ScA at decreasing concentrations, as shown in the figure, and viability assessed by XTT assay after 72 hours; FIG. 30(B) illustrates an image of human endothelial cells that were plated on Matrigel-coated surfaces and allowed to form tubules for 48 hours in the presence of DMSO diluent (upper panel), when ScA was added at 10 mN and 100 µM (lower two panels), as described in detail in Example 7, below.

FIGS. 31(A-F) illustrates fluorescence microscopy images of transgenic Tg(fli1:EGFP) zebrafish embryos in which GFP is expressed in endothelial cells, where the embryos were incubated without ScA, FIG. 31(A), or with increasing concentrations of ScA: 80 nM in FIG. 31(B), 160 nM in FIG. 31(C), 300 nM in FIG. 31(D) 1.6 µM in FIG. 31(E) or 3 µM in FIG. 31(F), and FIG. 31(G) graphically illustrates data as collated from blood vessel morphology (growth) as recorded by fluorescence microscopy, where disks impregnated with 100 ng of bFGF were placed on the chorioallantoic membrane of eleven day old chicks to induce angiogenesis in the absence or presence of ScA, and after 72 hours (h), disks were removed, and the vascularity of the underlying chorioallantoic membrane determined by direct counting of branch points using a dissecting microscope; FIG. 31(H) graphically illustrates data from NB7 neuroblastoma cells lacking caspase 8 (filled bar) or NB7-C8 cells reconstituted for caspase 8 expression (open bars), which were seeded into ten day old chick chorioallantoic membranes to form tumors and after 72 hours, ScA was added topically to each growing tumor mass, as described in detail in Example 7, below.

Like reference symbols in the various drawings indicate like elements.

DETAILED DESCRIPTION

Figure 7A:
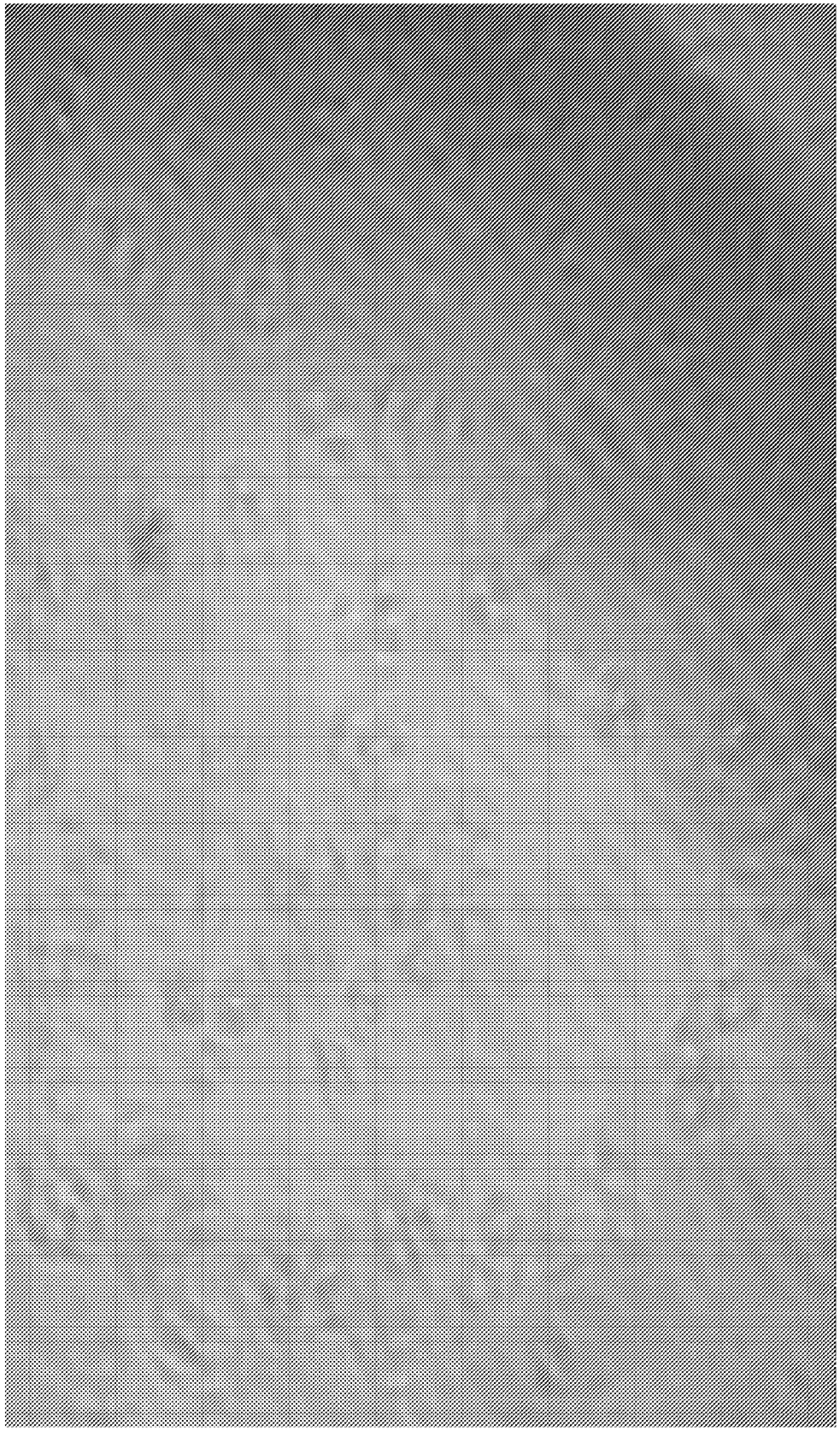
FIG. 7A illustrates microscopy images of cells with DMSO (1%) as a control at 24 h.
Figure 7B:
FIG. 7B—ScA (WG-144) on A-549 cells at 100 nM 24 h.
Figure 7C:
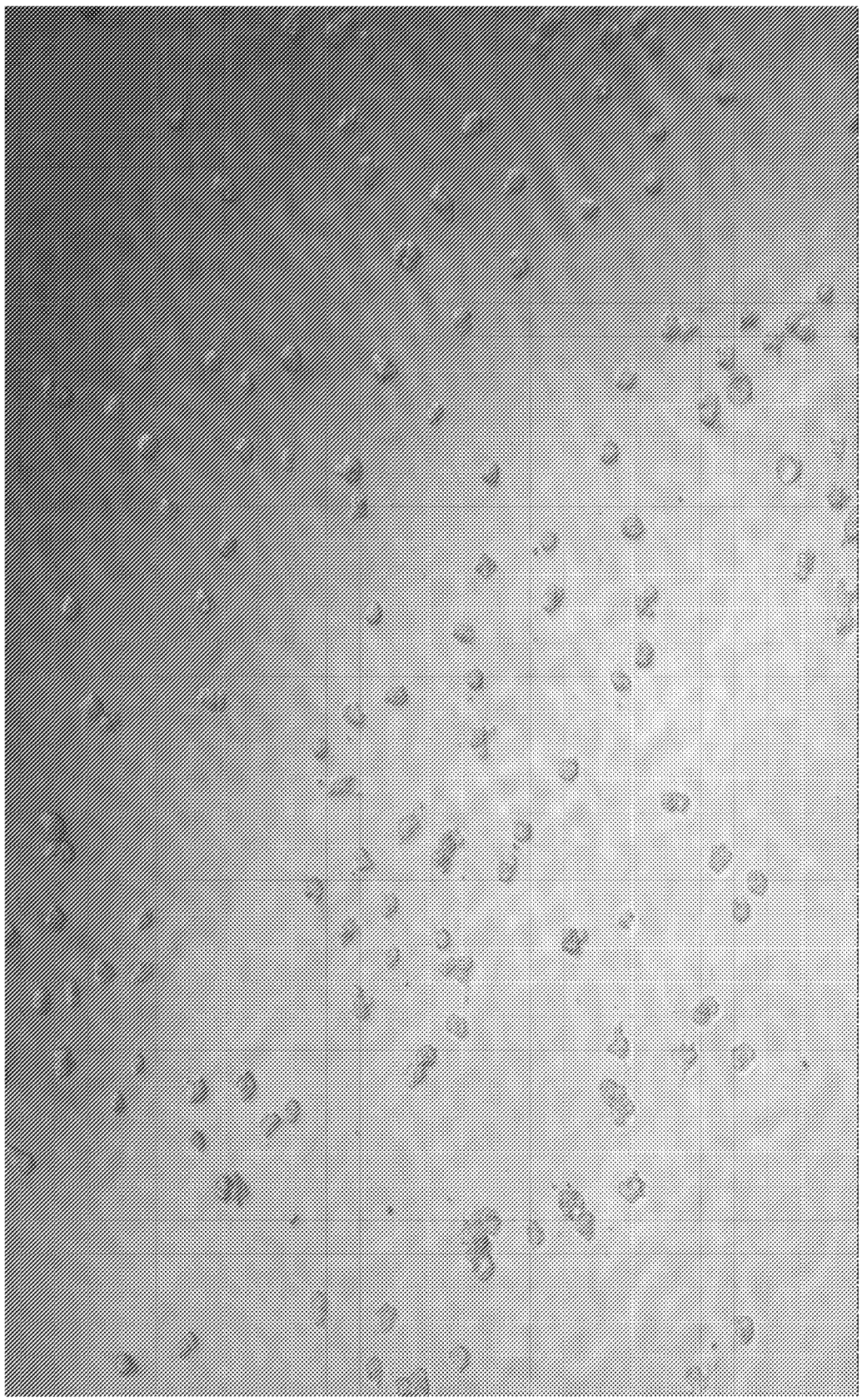
FIG. 7C—ScA (WG-144) on A549 cells 1.0 uM 24 h.
Figure 7D:
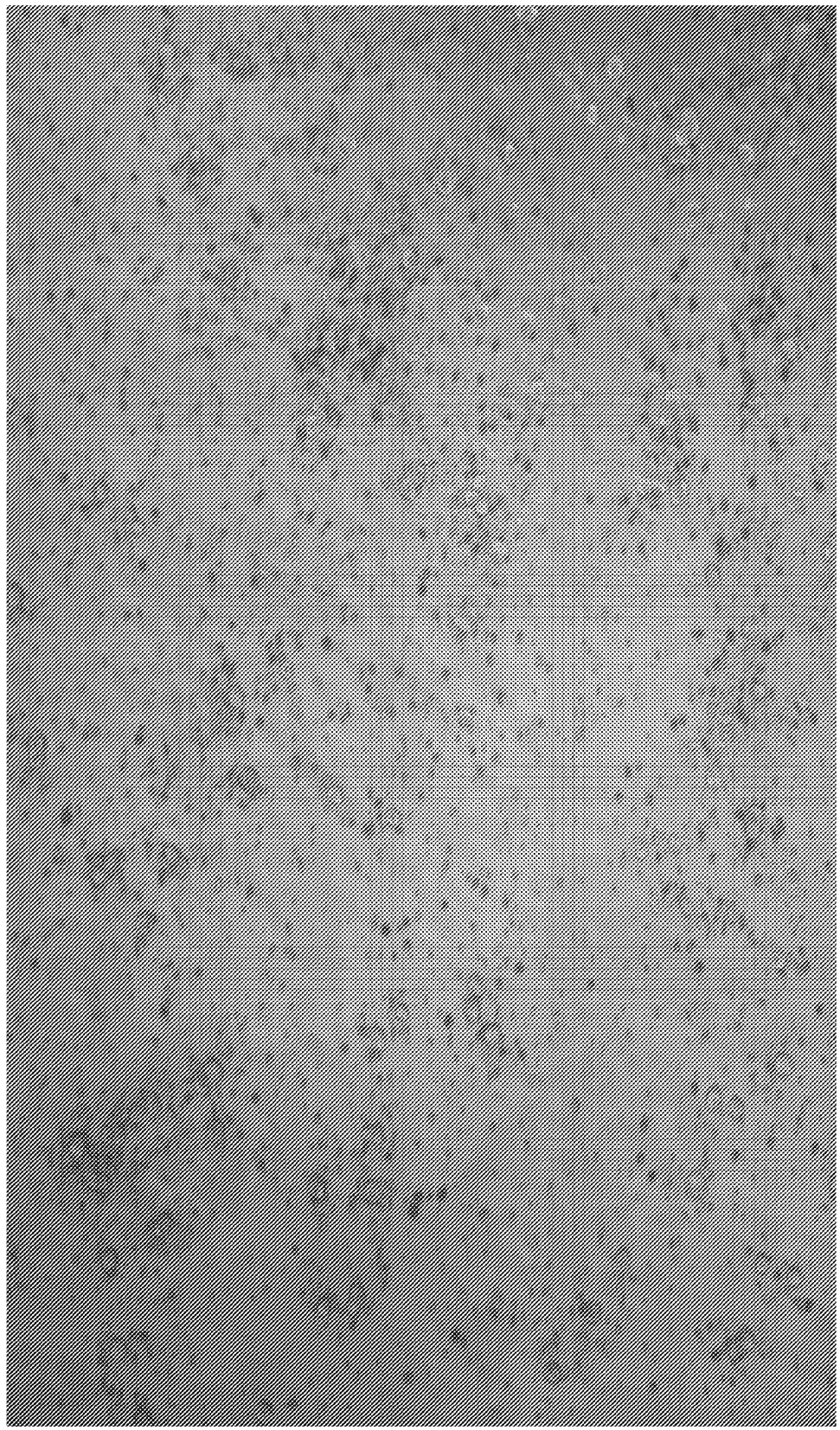
FIG. 7D—ScA (WG-144) on A549 cells, 10 uM, 24 h, as described in detail in Example 1, below.

The invention provides lipopeptides and analogs, and pharmaceutical compositions comprising them, and methods for using them comprising treating, preventing, reversing and/or ameliorating any cell proliferative condition, e.g., a skin condition such as psoriasis, or a hormone-dependent tumor or a hormone-influenced non-malignant disorder such as benign prostate hyperplasia (BPH) and endometriosis; or any disease or condition having an inflammatory component, e.g., an autoimmune disease such as rheumatoid arthritis, or an infectious disease; including treating, preventing or ameliorating any disease states associated with unwanted angiogenesis and/or cellular proliferation, such as diabetic retinopathy, wet-age related macular degeneration, neovascular glaucoma, rheumatoid arthritis, and psoriasis.

While the invention is not limited by any specific mechanism of action, in one aspect, the compositions and methods of the invention are used to induce apoptosis in a target cell, e.g., a hyperplastic or dysfunctional cell, e.g., vascular cells and/or tumor-associated neovasculature. Cell based assays with somocystinamide A demonstrated a plasma membrane based mechanism of induction of apoptosis via an extracellular death inducing signaling path. Triggering the external apoptotic program in tumor cells by aggregation of death-inducing signaling complexes with the use of novel small molecules of this invention provides a novel approach to antitumor and anti-neovasculature or dysfunctional vasculature therapeutics and prophylaxis. Thus, in one aspect, the compositions and methods of the invention are used to induce apoptosis in a target cell via an extracellular death inducing signaling path.

In order to invade normal tissues, and to metastasize, malignant cells acquire new surface properties; while the invention is not limited by any specific mechanism of action, in one aspect, the compositions and methods of the invention can disrupt the cells ability to acquire and/or maintain these new surface properties. Thus, in one aspect, the compositions and methods of the invention are used to modify changes in cell polarity and/or accompanying alterations in the local topology of proteins, lipids and sugars, including those induced by the acquiring of a dysplastic, e.g., cancerous or malignant, state. In one aspect, the compositions and methods of the invention are used to modify local surface anatomic changes of dysplastic, e.g., cancerous or malignant, cells to create a therapeutic effect.

In one aspect, this invention encompasses novel molecules, as described herein, that are low molecular weight, constrained and dimeric cytotoxins that can selectively kill cells, e.g., cancer cells, having a specific spatial relationship between receptors, e.g., targeted receptors. In one aspect, novel molecules of this invention trigger an external apoptosis pathway by clustering together on the plasma membrane various components of the Death-Inducing-Signaling-Complex (so-called "DISC"). Novel molecules of this invention, including the dimeric cytotoxin embodiments, can selectively assemble the DISC, depending on the distance between the receptors, and whether they are to be cross-linked.

In alternative embodiments, compounds of this invention are low-molecular weight, symmetrically dimeric lipid-like molecules with an internal disulfide bridge. Initial screening assays have shown that they are cytotoxic to cell lines at widely varying concentrations from low picomolar to low micromolar, consistent with variable expression of a receptor target. In one aspect, under some conditions, reduction of the internal disulfide may significantly reduce cytotoxic activity.

As discussed below, the exemplary somocystinamide A compound potently inhibited angiogenesis in a transgenic zebrafish model, without acute toxicity to the fish. Mechanistic investigations revealed that cell killing by the somocystinamide A compound dimer required the expression of caspase-8, a critical effector of the external apoptosis pathway. Moreover, cell visualization experiments showed that the lead compound induced the local clustering of DISC components into discrete cellular regions of susceptible cells. Accordingly, the invention provides a diverse class of dimeric molecules that can interact with one or more DISC molecules at a specified orientation in a cancer cell membrane, e.g., to induce apoptosis.

In one aspect, compositions of the invention are designed to target a specific cell, e.g., a cancer cell (to have specificity for a specific cell, e.g., a specific cancer cell) by the matching of the distance and angles between the two halves of a dimer of a composition of this invention with the distance and angles of the corresponding target receptors on the surface of the cell, e.g., a cancer cell.

In one aspect, compositions of the invention are designed to identify a specific cell, e.g., a cancer cell (to specifically identify a type of cell, e.g., a type of cancer cell) that can be a target for a specific therapy; in this embodiment, immune microscopic analysis using one or more antibodies to different components of the DISC complex is used. In this embodiment, the density and polarity of the DISC components, as revealed by microscopy, predict sensitivity to compositions of this invention (e.g., the dimeric cytotoxins of this invention) with different space lengths.

The invention provide molecules having different bridge lengths and angles, thereby also providing methods for selectively killing cells, e.g., cancer cells, by matching a composition of this invention (e.g., a dimeric toxin) with one or more surface anatomic properties of the target cell, e.g., a cancer cell, as revealed by immune microscopy using antibodies against components of the DISC.

Diseases and Conditions

The lipopeptides and analogs of the invention, and the pharmaceutical compositions comprising them, can be useful to treat, reverse, prevent or ameliorate any vascular or endothelial cell proliferative condition; e.g., they can be used to treat, prevent or ameliorate (including slowing the progression of) normal, dysfunction (e.g., abnormally proliferating) blood vessels, including endothelial and/or capillary cell growth; including neovasculature related to (within, providing a blood supply to) hyperplastic tissue, a granuloma or a tumor.

Diabetic Retinopathy

In one embodiment of the invention, compositions and methods of the invention are used to treat, prevent or ameliorate an abnormal or diseased retinal tissue, e.g., to treat or ameliorate proliferative retinopathy and/or retinal neovascularization (ocular neovascularization) in an animals, including human beings, such as those with or at high risk of diabetic retinopathy. Diabetic retinopathy is a common microvascular complication in patients with type 1 diabetes; thus, the compositions and methods of the invention can be practiced on individuals with or at high risk of acquiring type 1 diabetes. The compositions and methods of the invention are used to treat, prevent or ameliorate the progression of background retinopathy to proliferative retinopathy, and to treat, prevent or ameliorate visual impairment through bleeding or retinal detachment by accompanying fibrous tissues.

Diabetic rat models of experimental retinopathy are well known in the art and can be used to validate the efficacy of various dosages and formulations of compositions and methods of the invention. For example, chronic hyperglycemia can be induced in 4-6 week old Wistar rats by intravenous injection of 60-65 mg/kg body weight streptozotocin. Diabetes can be monitored consecutively by taking body weight and blood glucose levels into consideration. When these rats reach, for example, a body weight of about 330g and their blood glucose levels of 25 nmol/l, compositions and methods of the invention can be administered to the retinal tissue at various times, e.g., at 1 to 2 week intervals.

Choroidal Neovascularization—age-related macular degeneration

In one embodiment of the invention, compositions and methods of the invention are used to treat, prevent or ameliorate choroidal neovascularization (CNV), a serious complication of age related macular degeneration characterized by the growth of new blood vessels from the choroid (through the Buch's membrane into the subretinal space). Compositions and methods of the invention are used to treat, prevent or ameliorate the formation of choroidal neovascular membranes from which blood and serum may leak, causing vision loss. Thus, compositions and methods of the invention are used to treat, prevent or ameliorate age-related macular degeneration.

Animal models of choroidal neovascularization in the subretinal space are well known in the art, e.g., see Tobe (1994) J. Jpn. Ophthaliol. Soc. 98:837-845; Shen (1998) Br. J. Ophthamomol. 82:1062-1071, can be used to validate the efficacy of various dosages and formulations of compositions and methods of the invention.

For example, a rat with CNV can be administered with compositions and methods of the invention. The CNV rats can be used for subretinal injections of compositions of the invention. See, e.g., Giordano, G., U.S. Pat. Application No. 20070077233.

In addition, fluorescein angiograms can be used to detect vascular leakage and determine and evaluate the vaso-permeability effect on blood vessels of the compositions and methods of this invention. Fluorescein angiography in the context of CNV is well known in the art. For example, fluorescein angiograms 5 to 10 days post-administration of a composition of this invention can be performed to determine areas of vascular leakage.

Rheumatoid Arthritis

In one embodiment of the invention, compositions and methods of the invention are used to treat, prevent or ameliorate pathological angiogenesis in rheumatoid arthritis (RA), or any pathological angiogenesis associated with a synovial tissue, such as chronic articular rheumatism. Compositions and methods of the invention are used to treat, prevent or ameliorate blood vessel and/or synovial cells proliferation in response to inflammatory stimuli, e.g., to treat, prevent or ameliorate the formation of a rheumatoid pannus, an aggressive invasive tissue. Compositions and methods of the invention are used to treat, prevent or ameliorate early states of synovitis, to treat, prevent or ameliorate the development of new vessels in the synovium (which deliver nutrients, oxygen, and cells to the proliferating pannus).

Animal models of RA are well known in the art and can be used to validate the efficacy of various dosages and formulations of compositions and methods of the invention. For example, one mouse arthritis model is the KRN/NOD mouse model, see, e.g., Kouskoff (1996) Cell 87:811-822 (a spontaneous mouse model RA generated by crossing a T cell receptor (TCR) transgenic line with the NOD strain). The transgenic KRN/NOD mice develop arthritis. In these animals, the disease starts between 25 and 29 days after birth with a very acute stage characterized by joint effusions and florid synovitis that spread to all joints between days 27 and 36. The nontransgenic KRN/NOD mice remain in good condition with no signs of arthritis during this period.

Throughout the disease duration the animals are scored for clinical symptoms of arthritis. In the control animals, arthritis development is unaltered. As part of the assessment, arthritis is quantified by measuring the thickness of each paw, for example, with a caliper-square. Then an arthritis index is calculated for each animal as the sum of the measures of the paws.

Some of the joints into which vector can be delivered for treatment and analyzed after the treatment are wrist, ankle, knee, shoulder, elbow, metacarpophalangeal, metatarsophalangeal and hip joints. Improvement in histologic features of arthritis after administration of a composition of this invention is analyzed. Tendon ruptures, synovial membranes invaded by the inflammatory materials, articular space filled with inflammatory materials, severe destructive lesions of the tarsal and carpal joints, panus proliferation and invasion, very intense bone lesions in terms of bone or cartilage destruction, fibrosis and fusion are some of the features of arthritis which are seen in the control RA animals but should be absent or should be seen with reduced severity in treated animals. In one aspect, administration of a composition of this invention reduces the clinical score as well as the extent of synovitis and joint destruction, which is indicative of a suppression of the formation of the pannus. Since blood vessels are required to nourish and maintain the pannus, inhibiting angiogenesis and synovial mass is almost certainly associated with a decrease in the total number of blood vessels.

Tumors and Neovasculature

The lipopeptides of the invention, and the pharmaceutical compositions comprising them, can be useful to treat, reverse, prevent (prophylaxis) or ameliorate any dysfunctional cell, or any abnormally (dysfunctional) dividing or metastasizing cell, e.g., a cancer or a tumor cell. The lipopeptides of the invention, and the pharmaceutical compositions comprising them, can be useful to treat, reverse, prevent (prophylaxis) or ameliorate any neovasculature related to (within, or providing a blood supply to) a tumor, and neovasculature cell growth is slowed, reversed or inhibited.

For example, cancers that can be treated, prevented or ameliorated by using compositions of this invention include lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and any combination thereof.

For example, many cancers, e.g., malignant gliomas, have extremely poor prognosis despite the use of currently available therapies such as surgery, radiation therapy, and chemotherapy; thus, administering pharmaceutical compositions comprising the compositions of this invention (the lipopeptides of the invention) can interfere with or block tumor angiogenesis and to inhibit tumor growth.

To evaluate and validate dosages, formulations, etc., of pharmaceutical compositions of this invention, tumors can be established in a suitable animal model, such as a mouse or a rat animal model. For example, GS9L (rat glioblastoma) cells can be used to establish tumors in rats; the GS9L cells can be transplanted intracerebrally to establish intracerebral tumor model and subcutaneously to establish a subcutaneous tumor model, as described by, e.g., by Heidenreich (2007) Int. J. Cancer 120(9):1899-908; Machein (1999) Human Gene Therapy 10:1117-1128.

Any clinically relevant assay can be used to screen the anticancer drugs of this invention in vivo, including orthotopic and metastatic rodent tumor models; e.g., a breast cancer tumor model can be used to evaluate and demonstrate the efficacy of compositions of the invention, including targeted nanoparticles comprising lipoproteins and analogs of this invention. A dorsal skinfold window chamber model can be used for direct imaging during the evolution of tumor vasculature and subcutaneous tumor tissue of breast cancer implants. The confocal microscopy data obtained can be quantified for determining the efficacy of a composition of this invention.

Pharmaceutical Compositions

The invention provides pharmaceutical compositions comprising lipopeptides and analogs of the invention, including somocystinamide A and analogs, and methods for making and using these pharmaceutical compositions, e.g., in the manufacture of medicaments for arterio-venous (AV) malformation, myocardial angiogenesis, plaque neovascularization, telangiectasia, hemophiliac joints, angiofibroma, wound granulation, wound healing, telangiectasia psoriasis scleroderma, pyogenic granuloma, coronary collaterals, ischemic limb angiogenesis, rubeosis, arthritis, diabetic neovascularization, fractures, vasculogenesis, and hematopoiesis; and other conditions and diseases as described herein.

The lipopeptides and analogs of the invention, and the pharmaceutical compositions comprising them, can be combined with, or used in conjunction with, any anti-angiogenic agent, e.g., thrombospondin, angiostatin5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, sulfonated distamycin A derivatives (e.g., PNU145156E, PNU153529, see, e.g., Corallini (1998) AIDS Res. Hum. Retroviruses 14:1561-1571); 16K prolactin fragment, linomide, thalidomide, pentoxifylline, genistein, TNP-470, endostatin, paclitaxel, docetaxel, polyamines, a proteasome inhibitor, a kinase inhibitor, a signaling peptide, accutin, cidofovir, vincristine, bleomycin, AGM-1470, platelet factor 4, minocycline or an anti-angiogenically effective amount of a 1,2-dithiol-3-thione (see, e.g., U.S. Pat. No. 7,199,122), or peripheral artery disease.

In alternative embodiments, the lipopeptides and analogs of the invention are formulated with a pharmaceutically acceptable carrier. In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents of the invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of lipopeptides and analogs of the invention include those suitable for oral/ nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of the hydrophobic active agents of the invention, including the somocystinamide A and analogs of the invention. Oil-based suspensions can be formulated by suspending an active agent (e.g., a somocystinamide A analog of the invention) in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these.

Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing this invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing this invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations of the invention can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations of the invention can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions of the invention are administered in an amount sufficient to treat, prevent and/or ameliorate normal, dysfunction (e.g., abnormally proliferating) blood vessels, including endothelial and/or capillary cell growth; including neovasculature related to (within, providing a blood supply to) hyperplastic tissue, a granuloma or a tumor. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of somocystinamide A or an analog thereof is in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for treating cancer, septic shock, infection, fever, pain and related symptoms or conditions. For example, the methods and/or compositions and formulations of the invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles and Liposomes

The invention also provides nanoparticles and liposomal membranes which target specific molecules, including biologic molecules, such as polypeptide, including cell surface polypeptides. Thus, in alternative embodiments, the invention provides nanoparticles and liposomal membranes targeting diseased and/or tumor (cancer) cells, dysfunction cells and/or normal cells, e.g., the compositions of the invention can target any neovasculature, e.g., a tumor vasculature, via incorporating specific ligands that specifically bind to growing blood vessels, including disease-associated or tumor vasculature, such as RGD or any $\alpha v \beta 3$ integrin antagonist to inhibit angiogenesis, Vascular Endothelial Growth Factor (VEGF, to target VEGF-R), and the like. See, e.g., U.S. patent application publication nos. 20070036751; 20060177443; 20060009622; and U.S. Pat. No. 7,115,261;

In alternative embodiments, the invention provides nanoparticles and liposomal membranes comprising molecules, e.g., peptides or antibodies, that selectively target diseased, infected, dysfunctional and/or cancer (tumor) cell receptors. In alternative embodiments, the invention provides nanoparticles and liposomal membranes using IL-11 receptor and/or the GRP78 receptor to targeted receptors on cells, e.g., on tumor cells, e.g., on prostate or ovarian cancer cells. See, e.g., U.S. patent application publication no. 20060239968.

Thus, in one aspect, the compositions of the invention are specifically targeted for inhibiting, ameliorating and/or preventing endothelial cell migration and for inhibiting angiogenesis, e.g., tumor-associated or disease- or infection-associated neovasculature.

The invention also provides nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., such as cancer, inflammatory diseases such as asthma, autoimmune diseases such as rheumatoid arthritis or infectious diseases. In treating cancer, a traditional antineoplastic agent is contained in the outer lipid vesicle of the nanocell, and an antiangiogenic agent of this invention is loaded into the nanocore. This arrangement allows the antineoplastic agent to be released first and delivered to the tumor before the tumor's blood supply is cut off by the composition of this invention.

The invention also provides multilayered liposomes, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome of the invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles to deliver a composition of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Kits and Libraries

The invention provides kits comprising compositions and methods of the invention, including cells and/or fish of the invention, target sequences, transfecting agents, transducing agents, instructions (regarding the methods of the invention), or any combination thereof. As such, kits, cells, vectors and the like are provided herein.

The invention will be further described with reference to the following examples; however, it is to be understood that the invention is not limited to such examples.

EXAMPLES

Example 1

Identifying Compounds of the Invention as Cell Cytotoxic and Anticancer Agents and Demonstrating their Efficacy This example provides data demonstrating somocystinamide A (compound 1 in FIG. 1a) induces cell cytotoxicity (in particular, apoptosis) at a nanomolar range. FIG. 1a, illustrates how somocystinamide A (compound 1) is highly acid-sensitive, rapidly and completely converting to a characterizable derivative (compound 2), also a composition of this invention. Somocystinamide A (compound 1) was shown to exhibit significant cytotoxicity against mouse neuro-2a neuroblastoma cells (with an $IC_{50}$=1.4 μg/mL); see Nogle, et al. (2002) Org. Lett., 4(7):1095-1098. Thus, FIG. 1b is an exemplary composition of this invention.

FIGS. 3A to D illustrate photomicrographs demonstrating that somocystinamide A (designed "WG-144") at various concentrations; with control, FIG. 3A, and at 1 μM (FIG. 3B), 100 μM (FIG. 3C) and 10 nM (FIG. 3D), inhibits tube formation of HUVEC/matrigel.

FIG. 4 illustrates confocal microscopy images of zebrafish expressing transgenic green fluorescent protein (GFP) in their endothelial cells, with 300 nM of somocystinamide A (ScA, designed "WG-144") and without ScA (control). In particular, FIG. 4 illustrates confocal microscopy images of the zebrafish expressing transgenic GFP in their endothelial cells after 12 hours (h) and 24 h in the brain (top two rows), intersegmental vesicles and dorsal aorta (bottom two rows), as indicated in the figure.

FIG. 5 illustrates confocal microscopy images of the zebrafish expressing transgenic GFP in their endothelial cells, with a dose-response study of somocystinamide A (ScA), as indicated in the figure: control is no ScA, and at 0.30 μM, 3.0 μM, 0.16 μM, 1.6 μM, and 0.08 μM ScA.

FIG. 6 is a chart summary of cell proliferation assays of somocystinamide A (ScA), demonstrating the anti-proliferative effect of somocystinamide A on M21 melanoma cells

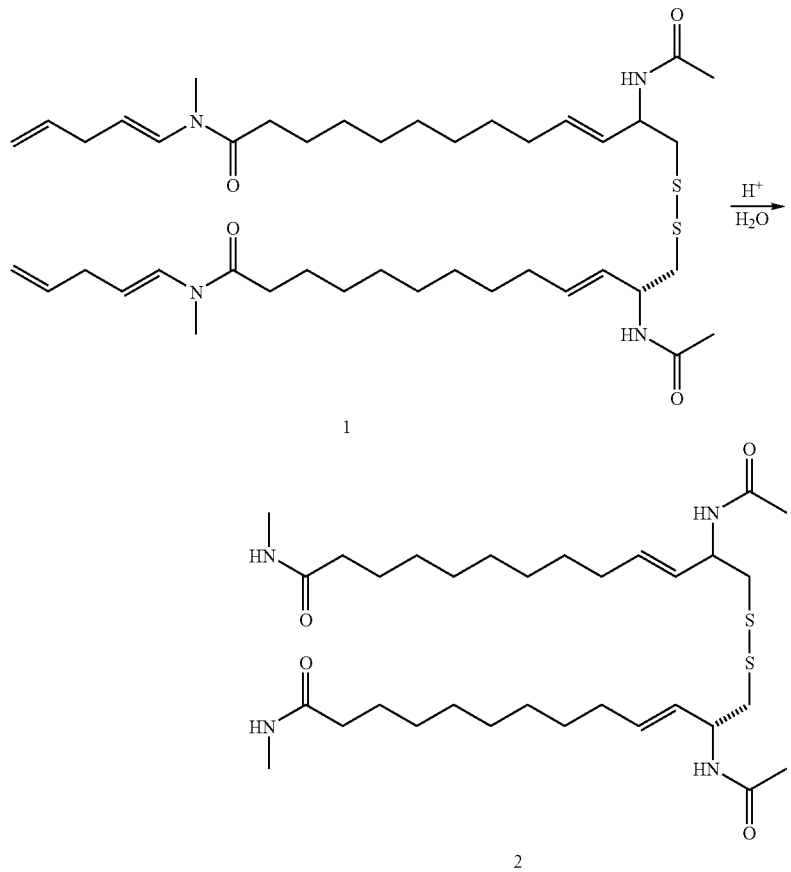

1

2

FIG. 2A illustrates a microtiter plate 72 hour (h) XTT assay for Huvec cell proliferation (2500 cells/well seeded), showing serial dilutions of structurally diverse marine natural compounds. Somocystinamide A (designated "WG-144") showed cytotoxicity in the nanomolar concentration range. FIG. 2B graphically illustrates the data for this study.

($IC_{50}$ of 1.28 μM), PC3 prostate cancer cells ($IC_{50}$ of 0.97 μM), TJK304 cells ($IC_{50}$ of 0.83 μM), Molt-4 T cell leukemia cells ($IC_{50}$ of 0.60 μM), NB7 neuroblastoma cells ($IC_{50}$ of 0.81 μM), NB7 caspase 8 positive cells ($IC_{50}$ of 0.012 μM), A-549 lung cancer cells ($IC_{50}$ of 0.046 μM), pancreatic metastatic mouse carcinoma cells ($IC_{50}$ of 0.008 μM), and HUVEC primary endothelial cells ($IC_{50}$ of 0.000004 μM), as described in detail in Example 1, below. The sensitivity of the caspase 8 positive cells is noted to be 100 times more sensitive to ScA.

FIG. 7 illustrates cell toxicity studies using A-549 cells and somocystinamide A (ScA); FIG. 7A illustrates microscopy images of cells with DMSO (1%) as a control at 24 h; FIG. 7B-ScA (WG-144) on A-549 cells at 100 nM 24 h; FIG. 7C-ScA (WG-144) on A549 cells 1.0 uM 24 h; FIG. 7D-ScA (WG-144) on A549 cells, 10 uM, 24 h. In FIG. 7A, the negative control (no ScA) the live cells are confluent. In FIG. 7B the cell are transitioning to apoptosis, in FIG. 7C the cells are in a state of apoptosis but no lysis, and in FIG. 7D the cells are in total lysis.

Figure 8:
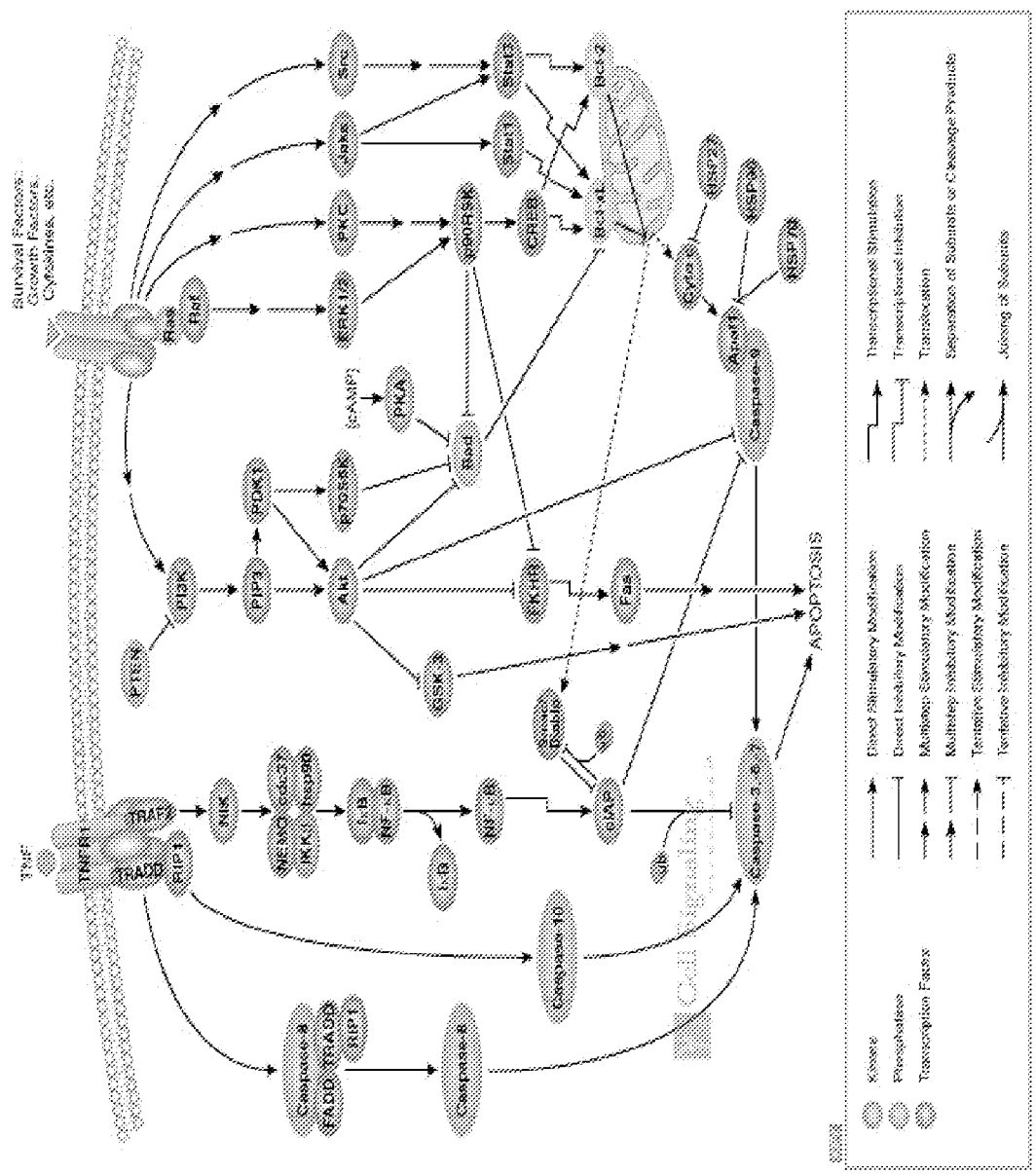
FIG. 8 illustrates exemplary, alternative biologic target(s) of compositions of this invention, as described in detail in Example 1, below.

While the invention is not limited by any particular mechanism of action for any somocystinamide A or any of the exemplary somocystinamide A analogs and variants thereof of this invention, FIG. 8 illustrates potential biologic target(s) of compositions of this invention; for example, in alternative embodiments, the compositions of this invention can inhibit directly or indirectly the biological activity of any of the biologic target(s) set forth in FIG. 8.

Figure 9:
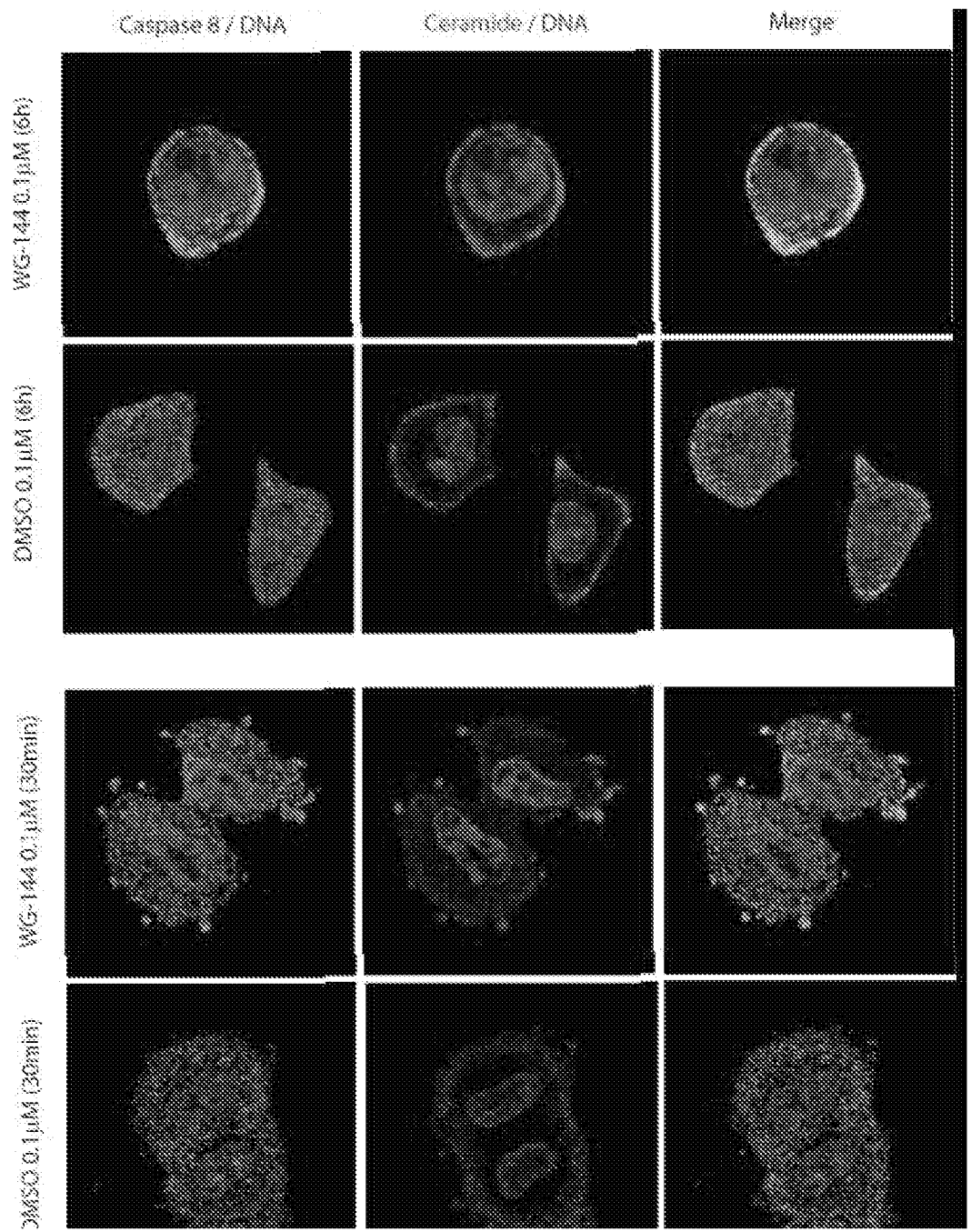
FIG. 9 illustrates confocal microscopy images of A-549 cells after exposure to 100 nm ScA, as described in detail in Example 1, below.
Figure 10:
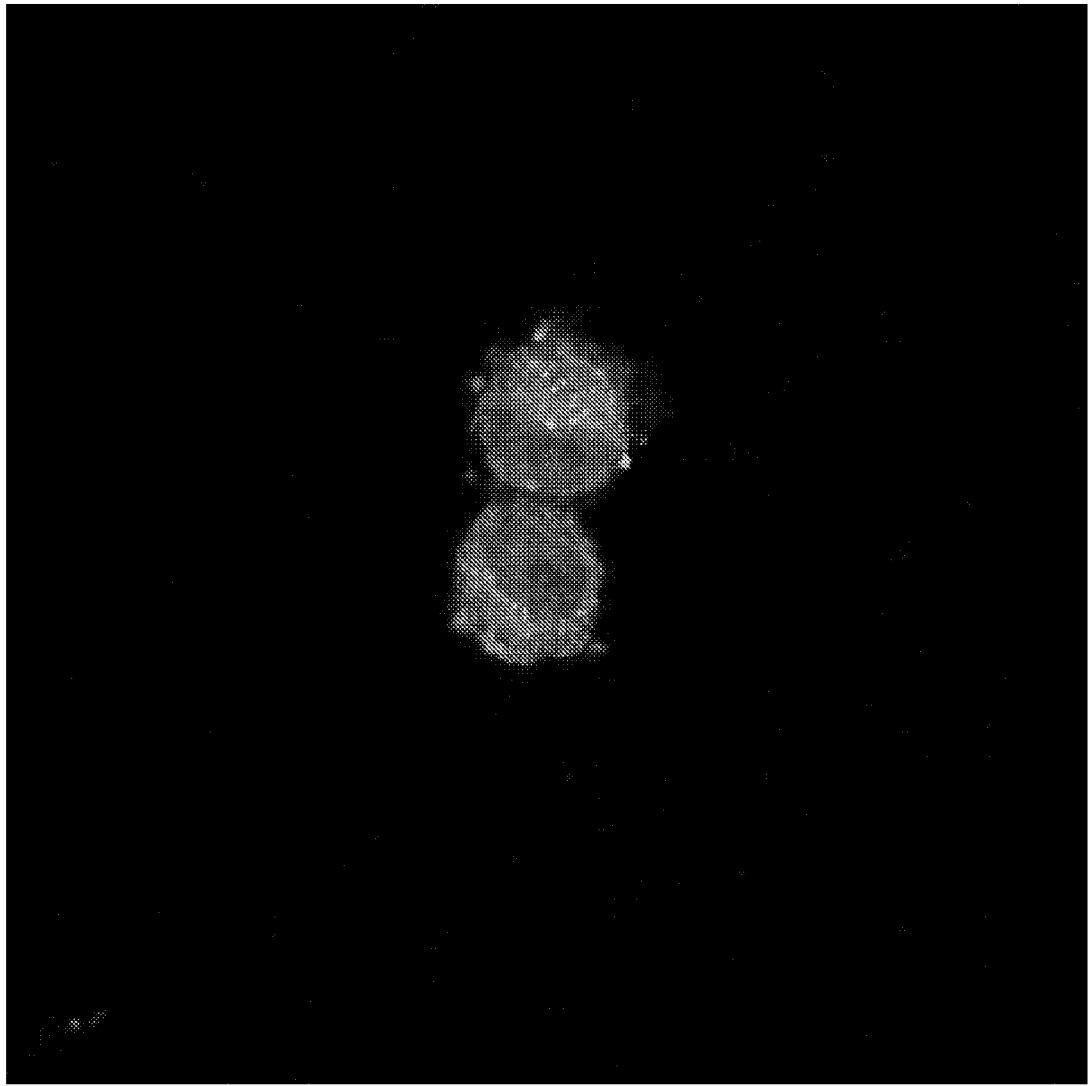
FIG. 10 illustrates a confocal microscopy image of ScA-induced colocalization of ceramide and caspase 8, showing migration towards polar caps and displacement of nucleus, as described in detail in Example 1, below.

While the invention is not limited by any particular mechanism of action for any somocystinamide A or any of the exemplary somocystinamide A analogs and variants thereof of this invention, proposed cellular mechanisms of action any one, several or all of the following:
Partitioning to form ceramide- enriched membrane domains (lipid rafts);
Direct activation of execution caspase 3, blocking ICAD/CAD;
Apoptosis;
Translocation and super-aggregation of death receptor (trimerized Fas/Trail);
Lateral segregation and colocalization into caps on one pole of cell;
Maximum Fas-signaling in caspase 8 expressing cells by
a.) Recruitment of cytoplasmic adapter protein FADD;
b.) Binding of pro-caspase 8 to FADD;
c.) formation of death inducing signaling complex—DISC;

FIG. 9 illustrates confocal microscopy images of A-549 cells after exposure to 100 Nm (0.10 μM) ScA (WG-144), as noted in detail in the figure; the cells were treated with ScA (WG-144) for 30 minutes or six hours with no ScA (the DMSO control) or 0.10 μM ScA, then stained for ceramide and caspase 8. This data demonstrates ScA (WG-144) induced colocalization of ceramide and caspase 8 showing migration towards polar caps and displacement of nucleus. FIG. 10 illustrates a confocal microscopy image of ScA (WG-144) induced colocalization of ceramide and caspase 8 showing migration towards polar caps and displacement of nucleus.

Figure 11:
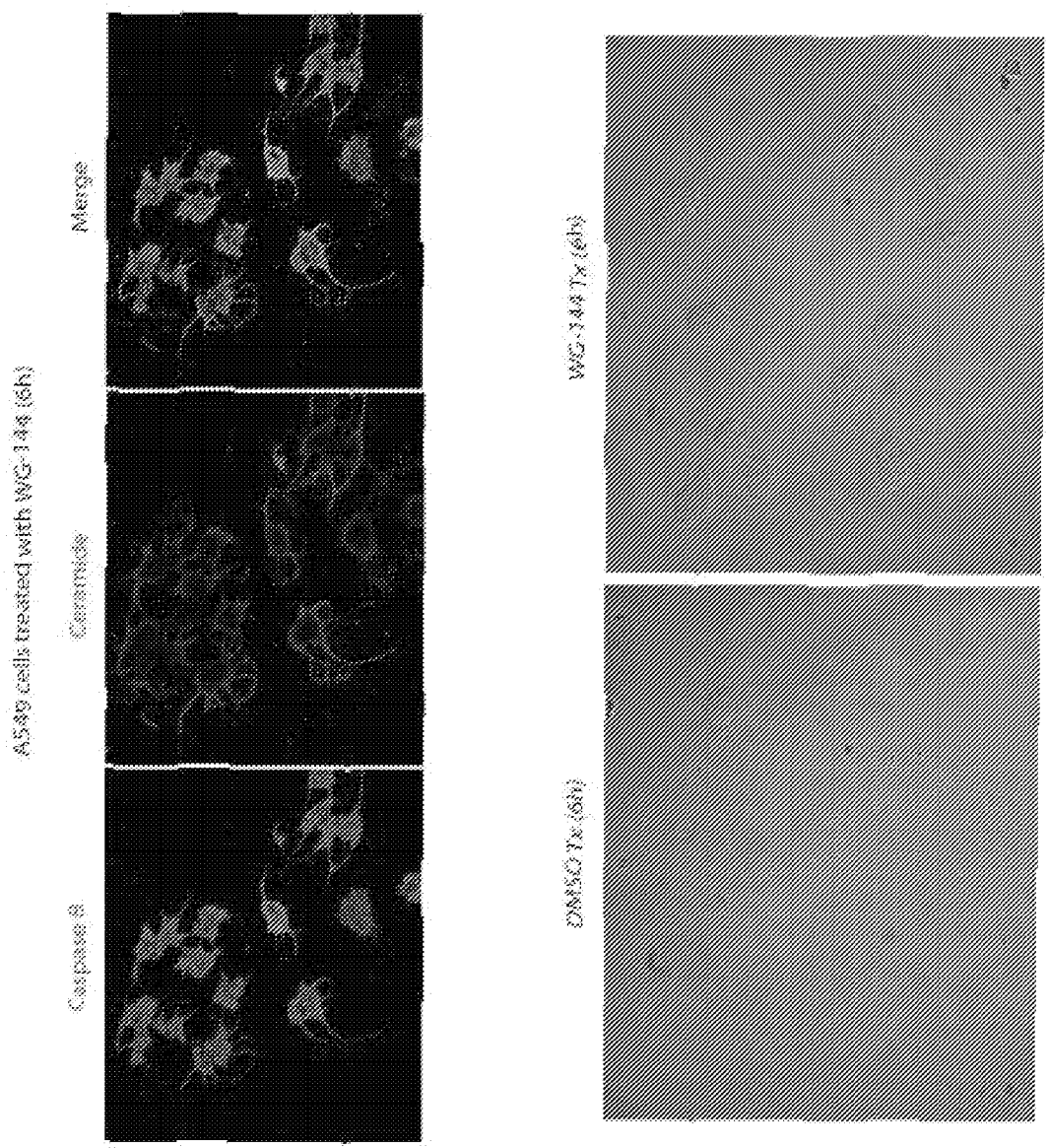
FIG. 11 illustrates a confocal microscopy image of the appearance of filopodia like protrusions in A-549 cells after sublytic (1 uM) exposure to ScA (WG-144), as described in detail in Example 1, below.

FIG. 11 illustrates a confocal microscopy image of the appearance of filopodia like protrusions in A-549 cells after sublytic (1 uM) exposure to ScA (WG-144); the cells were treated with ScA (WG-144) for six hours, then stained for ceramide and caspase 8.

Figure 12:
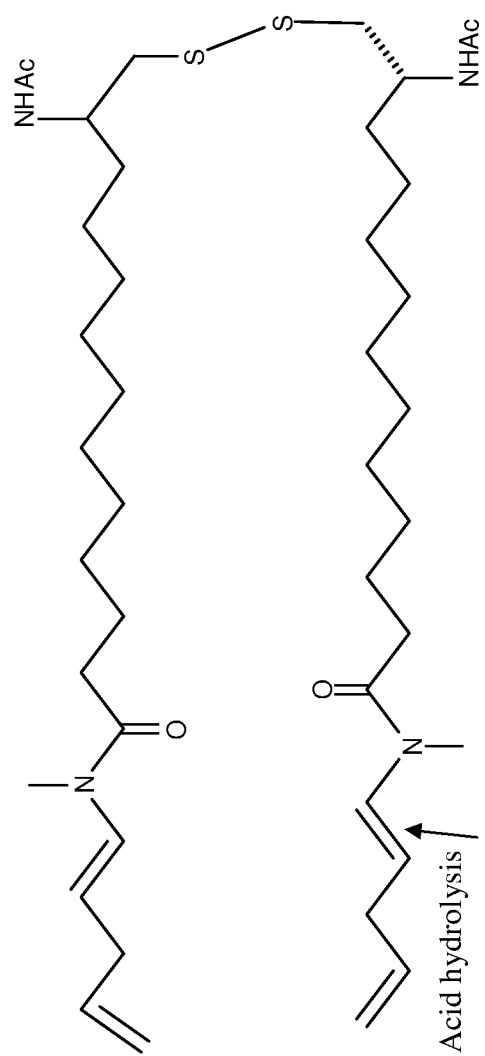
FIG. 12 illustrates alternative means (e.g., enzymatic reduction or acid hydrolysis) to modify somocystinamide A or any exemplary analog of this invention to generate an alternative molecule of this invention, as described in detail in Example 1, below.

FIG. 12 illustrates alternative means (e.g., enzymatic reduction or acid hydrolysis) to modify somocystinamide A or any exemplary analog of this invention to generate an alternative molecule of this invention, or as a chemical means to conjugate somocystinamide A or any exemplary analog of this invention to another molecule, which is also a composition of the invention. The arrow indicates an exemplary site of acid hydrolysis on ScA; enzymatic reduction of ScA can occur at the disulfide bond. The products of enzymatic reduction or acid hydrolysis are also compositions of the invention.

Figure 13:
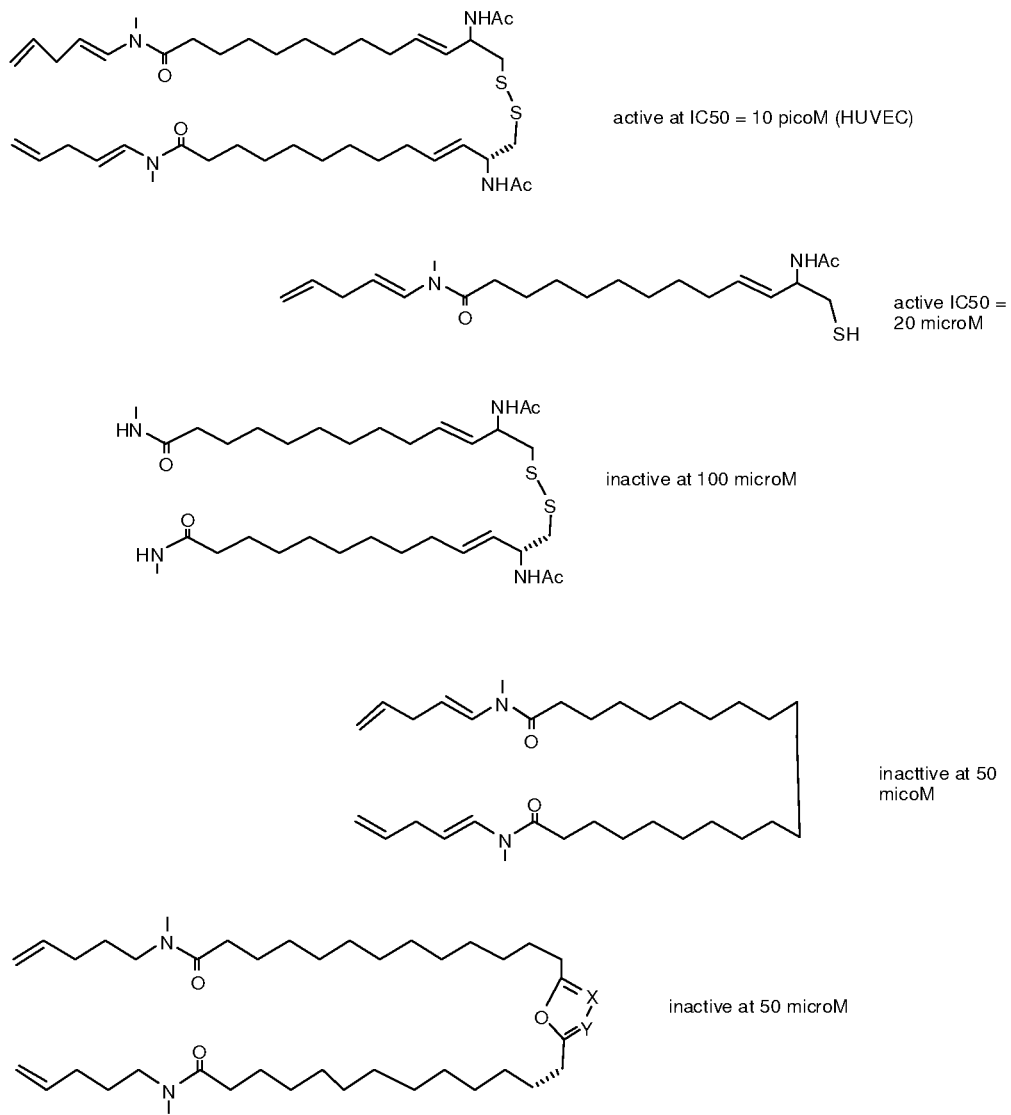
FIG. 13 illustrates structure-activity of exemplary somocystinamide analogs of the invention, as described in detail in Example 1, below.

FIG. 13 illustrates structure-activity of exemplary somocystinamide analogs of the invention; all are also compositions of the invention.

Figure 14:
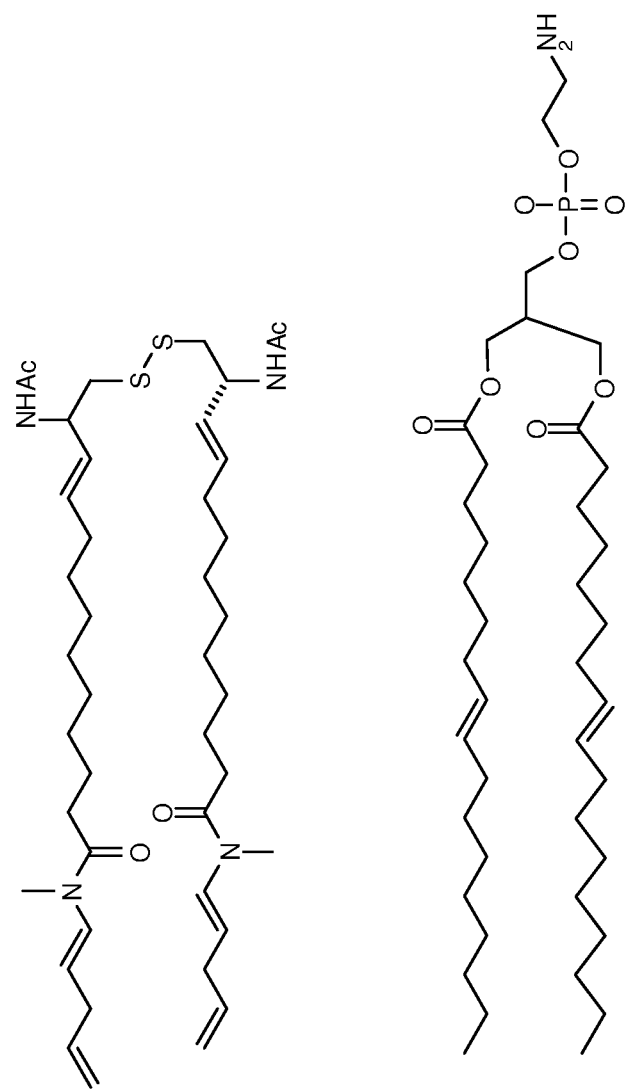
FIG. 14 illustrates structural similarities between somocystinamide A (designed "WG-144") and phospholipids (DOPE, or dioleoylphosphatidylethanolamine, is shown in the figure), as described in detail in Example 1, below.

FIG. 14 illustrates structural similarities between somocystinamide A (designed "WG-144") and phospholipids (DOPE, or dioleoylphosphatidylethanolamine, is shown in the figure), which are the building blocks of liposome nanoparticles. DOPE is just one of many phospholipids that can be used to practice this invention, e.g., to build liposomes and/or nanoparticles of this invention.

Figure 15:
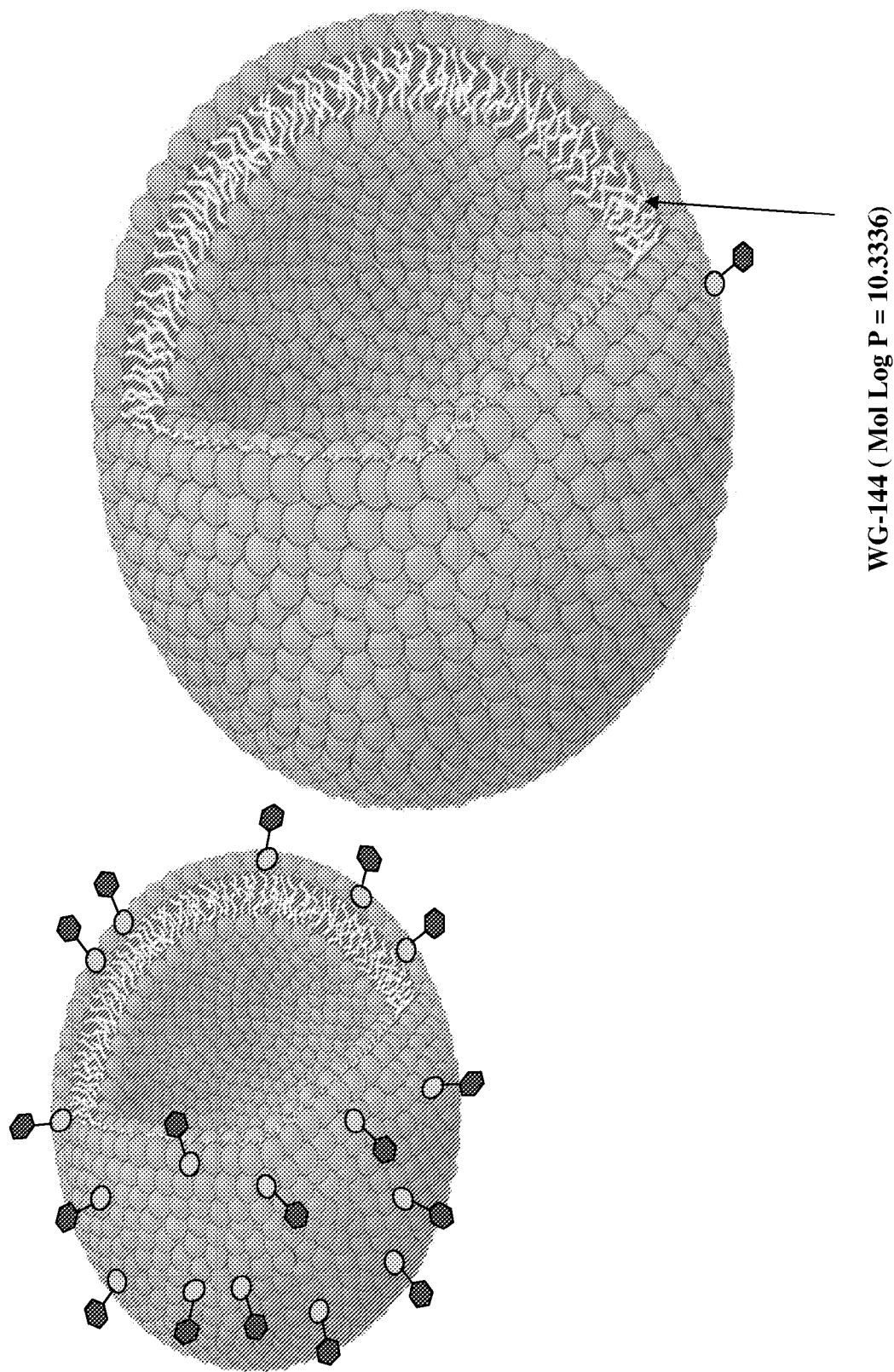
FIG. 15 illustrates an exemplary nanoparticle of the invention, as described in detail in Example 1, below.

FIG. 15 illustrates an exemplary nanoparticle of the invention comprising: somocystinamide A (designed "WG-144"), (2%) DSPE=distearoyl-phosphatidylethanolamine (30%), DOPE-mPeg (8%), cholesterol (30%), where DOPE=dioleoylphosphatidylethanolamine (30%). This exemplary nanoparticle has a 100 nm hydrodynamic diameter and a mol. Log P of 10.3336.

Figure 16:
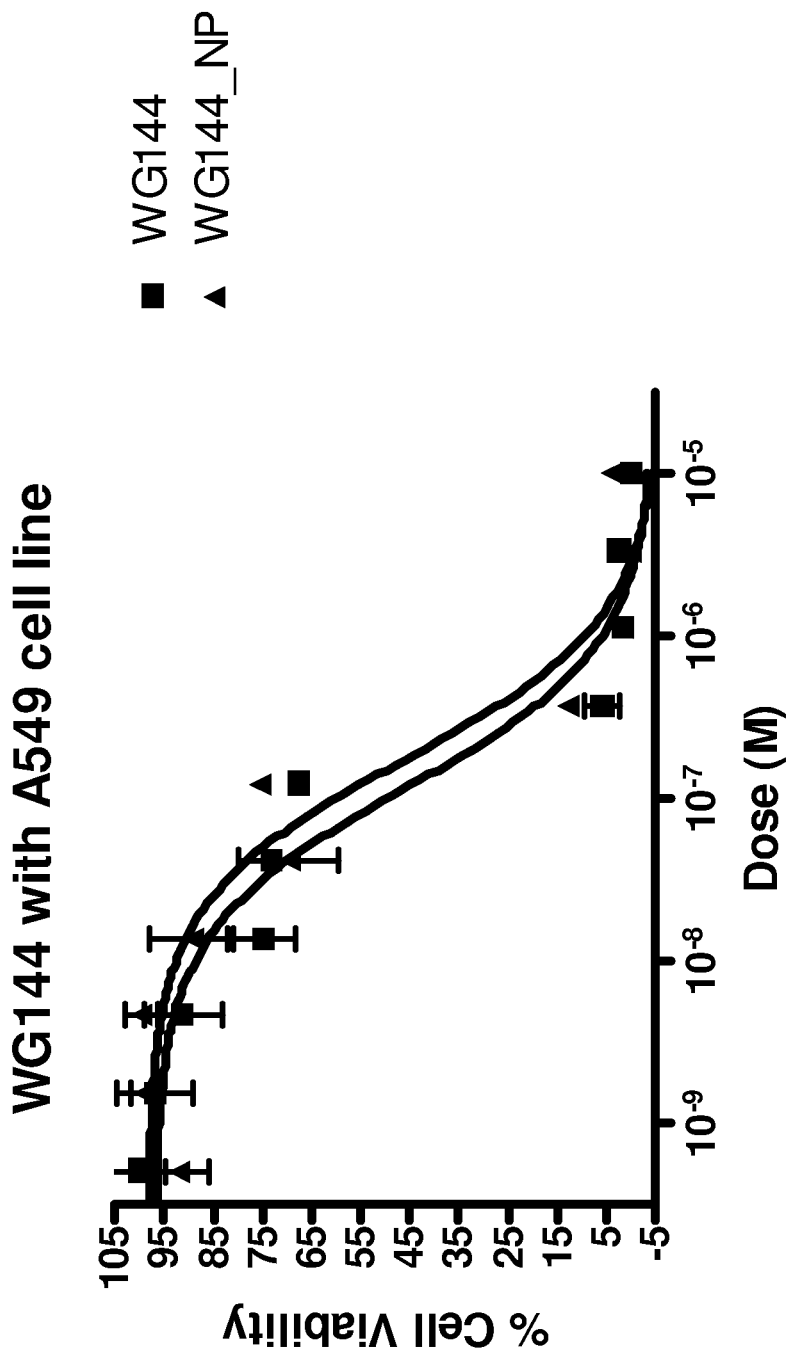
FIG. 16 graphically summarizes the data demonstrating the cytotoxicity of an exemplary somocystinamide A nanoparticles of this invention on A-549 cells, as described in detail in Example 1, below.

FIG. 16 graphically summarizes the data demonstrating the cytotoxicity (as indicated by percent "cell viability") of an exemplary somocystinamide A nanoparticles of this invention (the "MC-144" nanoparticle of FIG. 15) on A-549 cells; where the ScA comprising nanoparticles at the indicated dosages (in M, at $10^{-9}, 10^{-8}, 10^{-7}, 10^{-6}, 10^{-5}$) have an $IC_{50}$ of 172 nM, and the ScA alone has an $IC_{50}$ of 114 nM.

Figure 17:
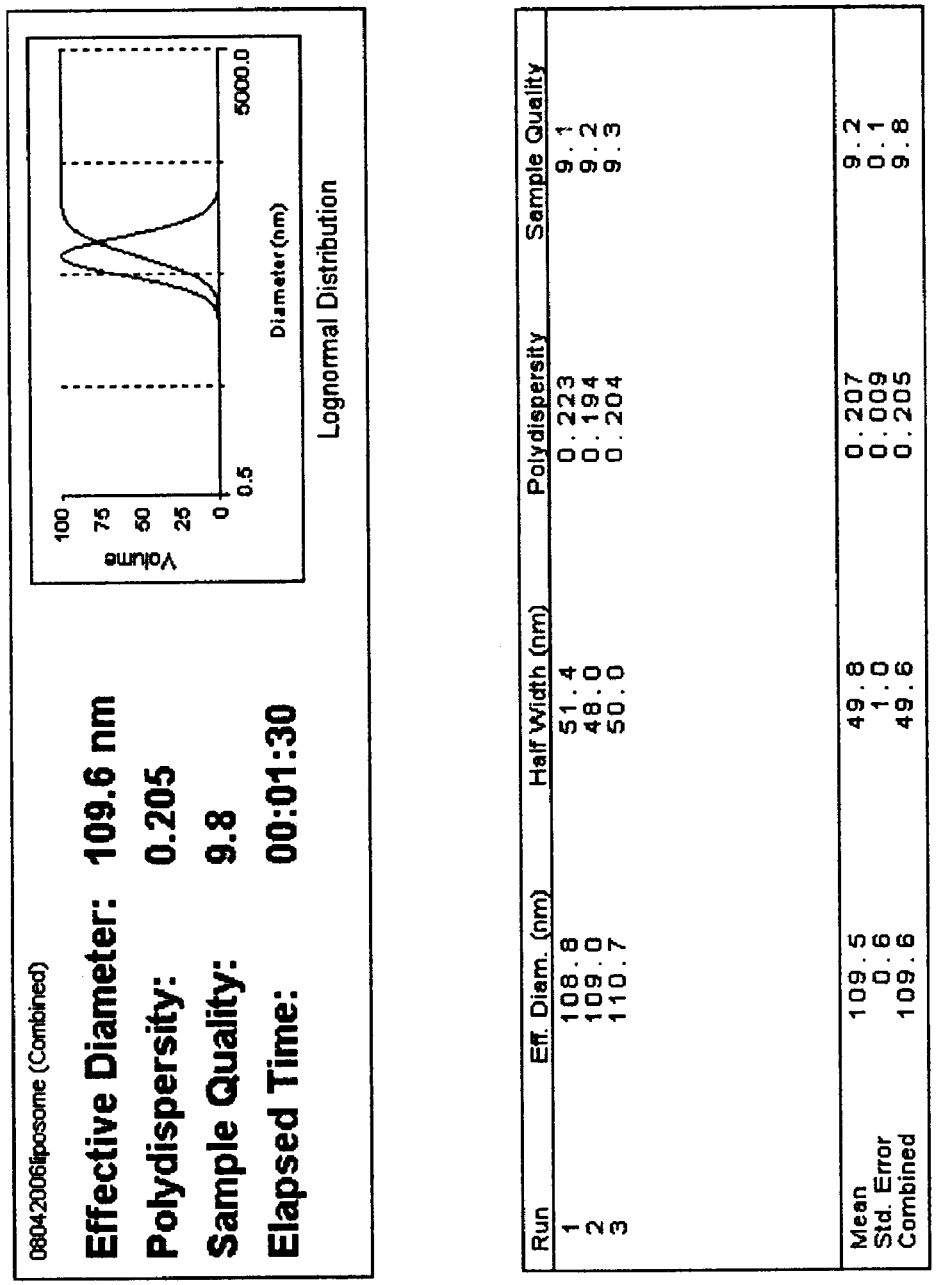
FIG. 17 in chart and graphic form summarizes particle size and distribution of exemplary nanoparticle of the invention, as described in detail in Example 1, below.

FIG. 17 in chart and graphic form summarizes particle size and distribution of exemplary nanoparticle of the invention; noting it has a 109.6 nm hydrodynamic diameter, a polydispersity of 0.205, a sample quality of 9.8. Lognormal distribution of diameter per unit volume is indicated in graphic form.

Figure 18:
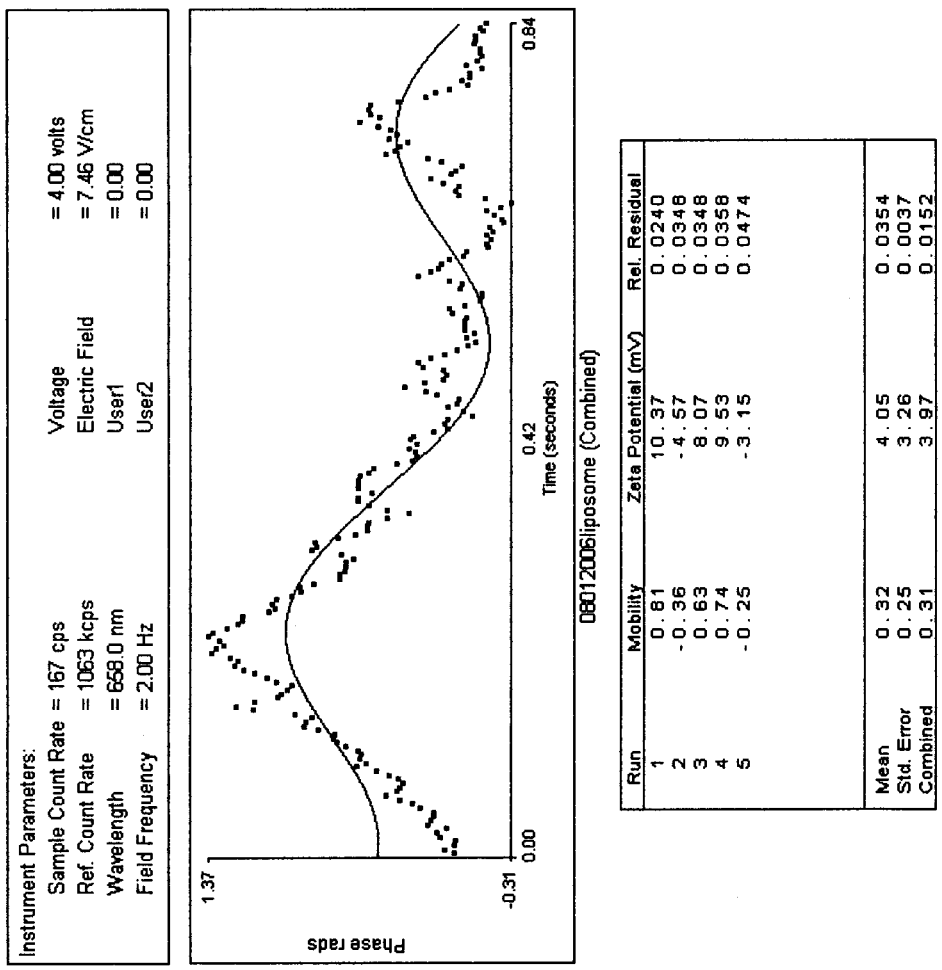
FIG. 18 in chart and graphic form summarizes the zeta potential (in mV) of exemplary somocystinamide A (designed "WG-144") nanoparticles of the invention, as described in detail in Example 1, below.

FIG. 18 in chart and graphic form summarizes the zeta potential (in mV) of exemplary somocystinamide A (designed "WG-144") nanoparticles of the invention.

Figure 19:
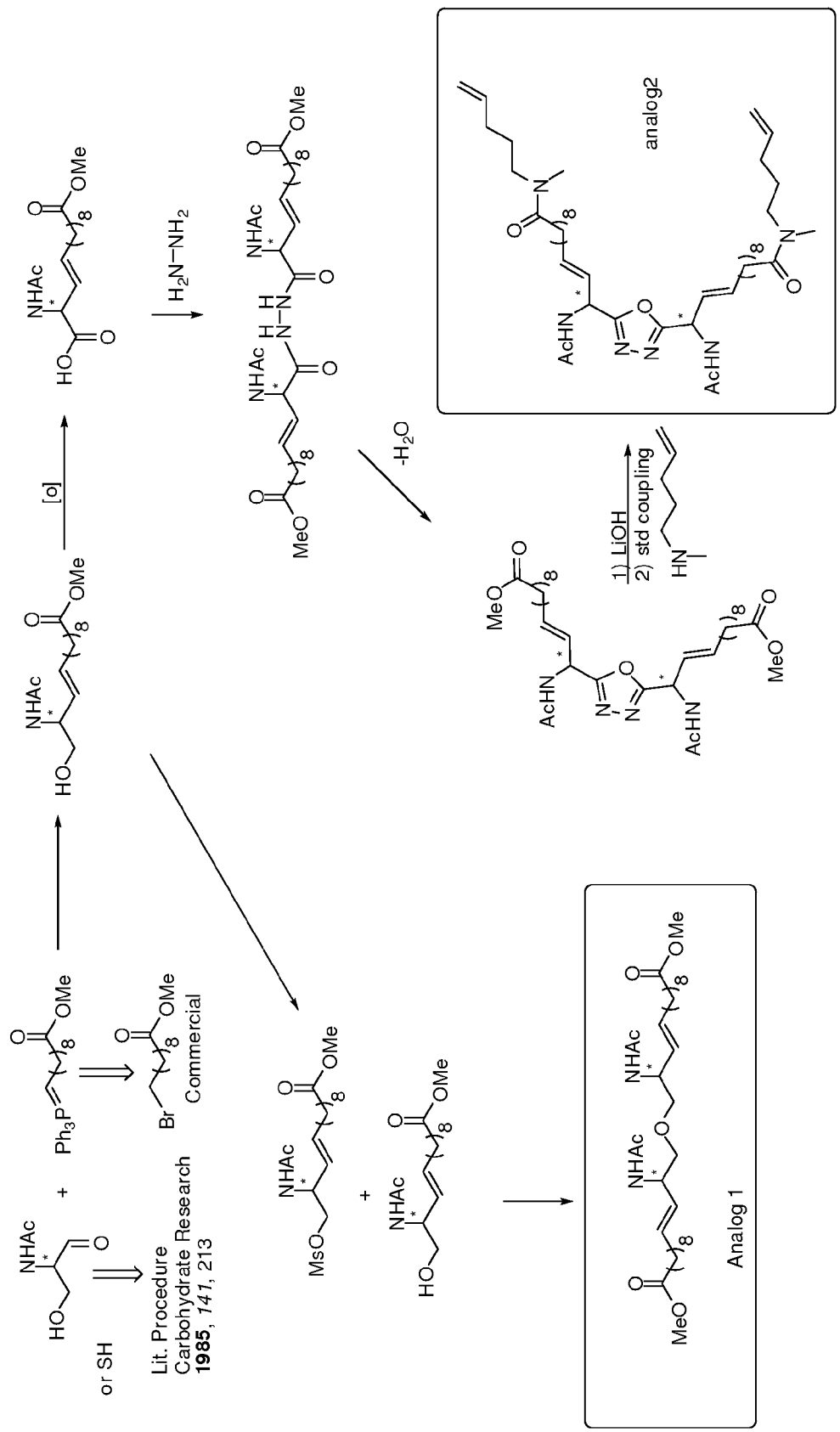
FIG. 19 illustrates the total synthesis and analoging of somocystinamide A, as described in detail in Example 1, below.

FIG. 19 illustrates the total synthesis and analoging of somocystinamide A.

Figure 20:
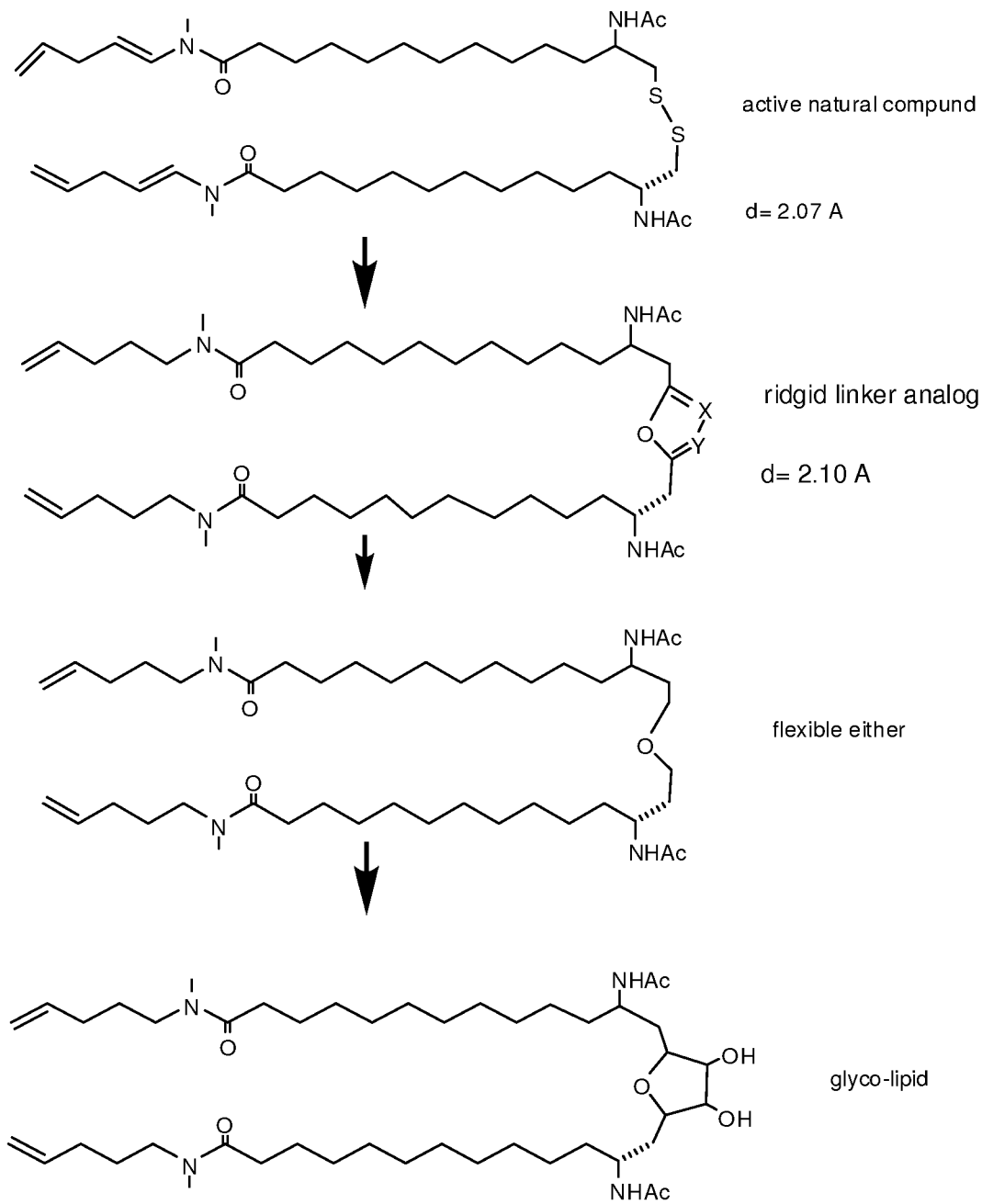
FIG. 20 ("analoging natural compound for drugability") illustrates various exemplary compositions of this invention, analogs of somocystinamide A, e.g., as an "active natural compound" and with a "rigid liker" analog, or as a flexible ether, or as a glycolipid, as described in detail in Example 1, below.

FIG. 20 ("analoging natural compound for drugability") illustrates various exemplary compositions of this invention, analogs of somocystinamide A, e.g., as an "active natural compound" and with a "rigid liker" analog, or as a flexible ether, or as a glycolipid.

Figure 21:
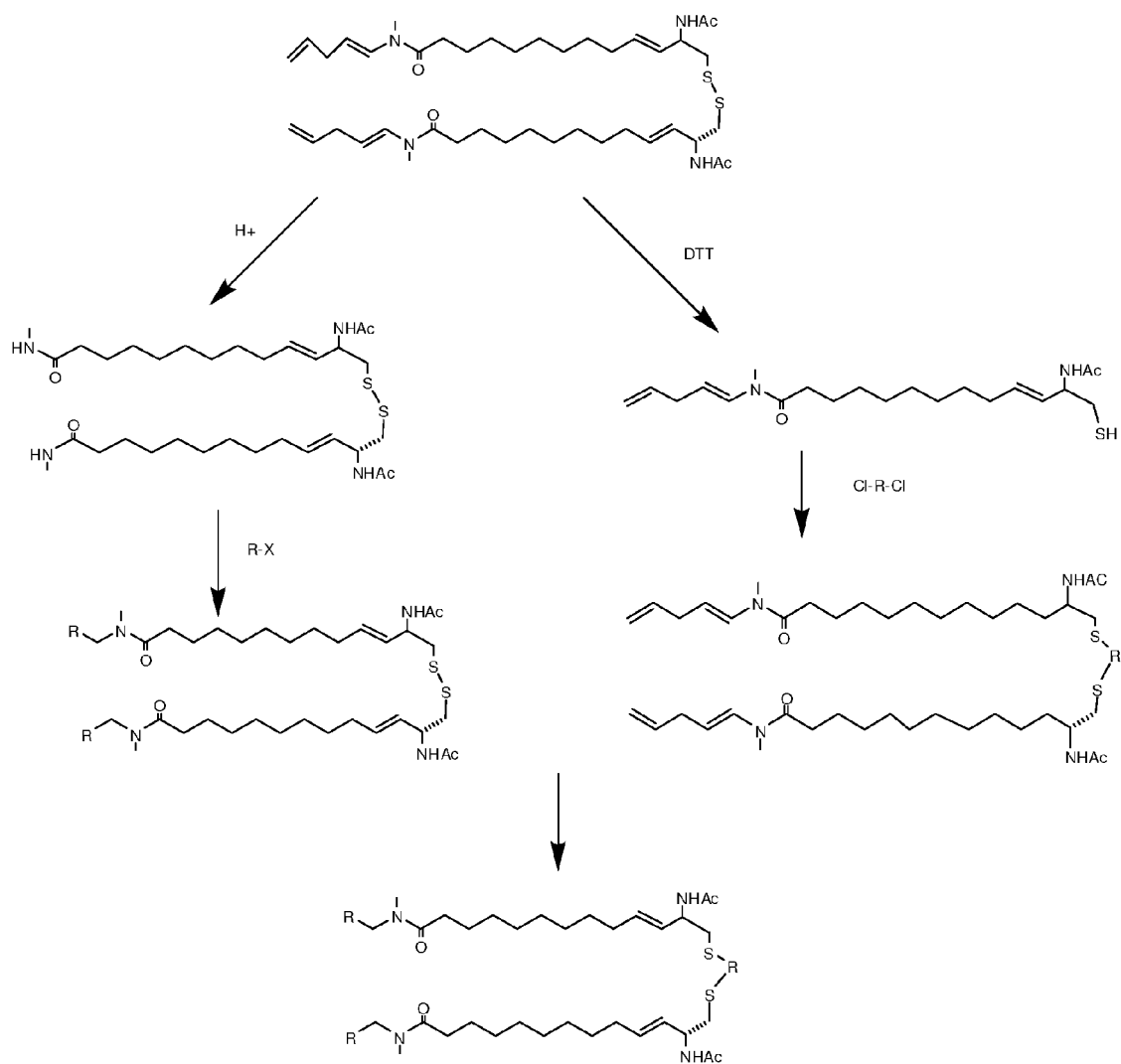
FIG. 21 illustrates compositions of this invention, and an exemplary regioselective reconstructive fragmentation of somocystinamide A, as described in detail in Example 1, below.

FIG. 21 illustrates compositions of this invention, and an exemplary regioselective reconstructive fragmentation of somocystinamide A.

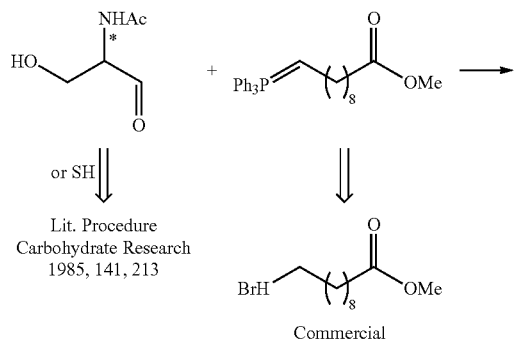

31 32
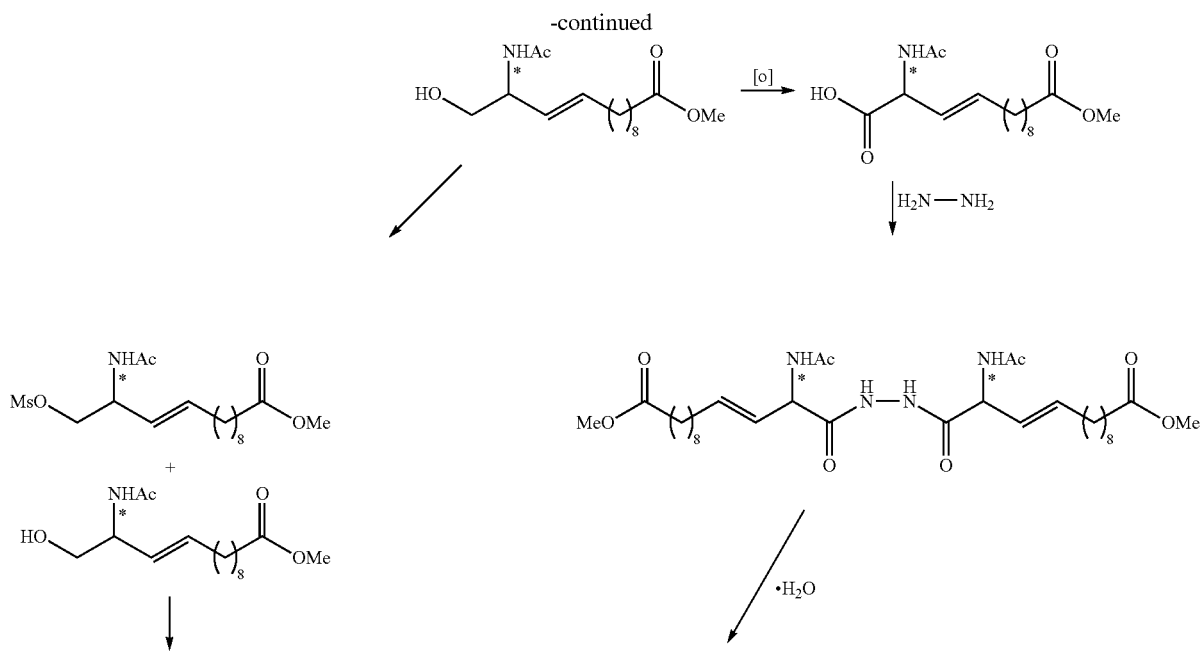
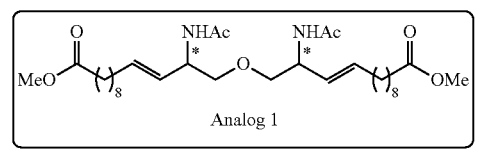
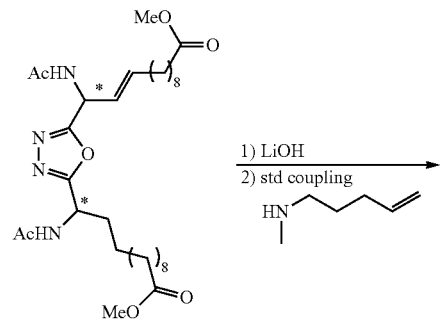
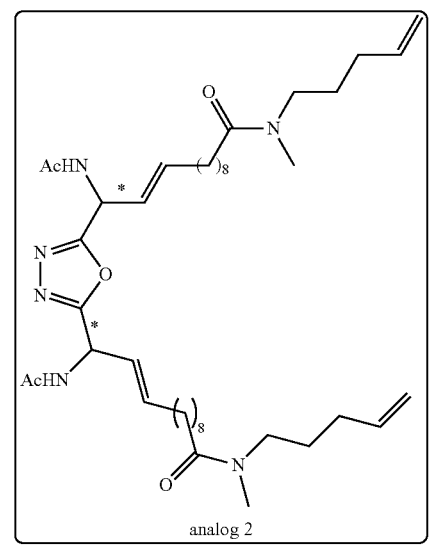

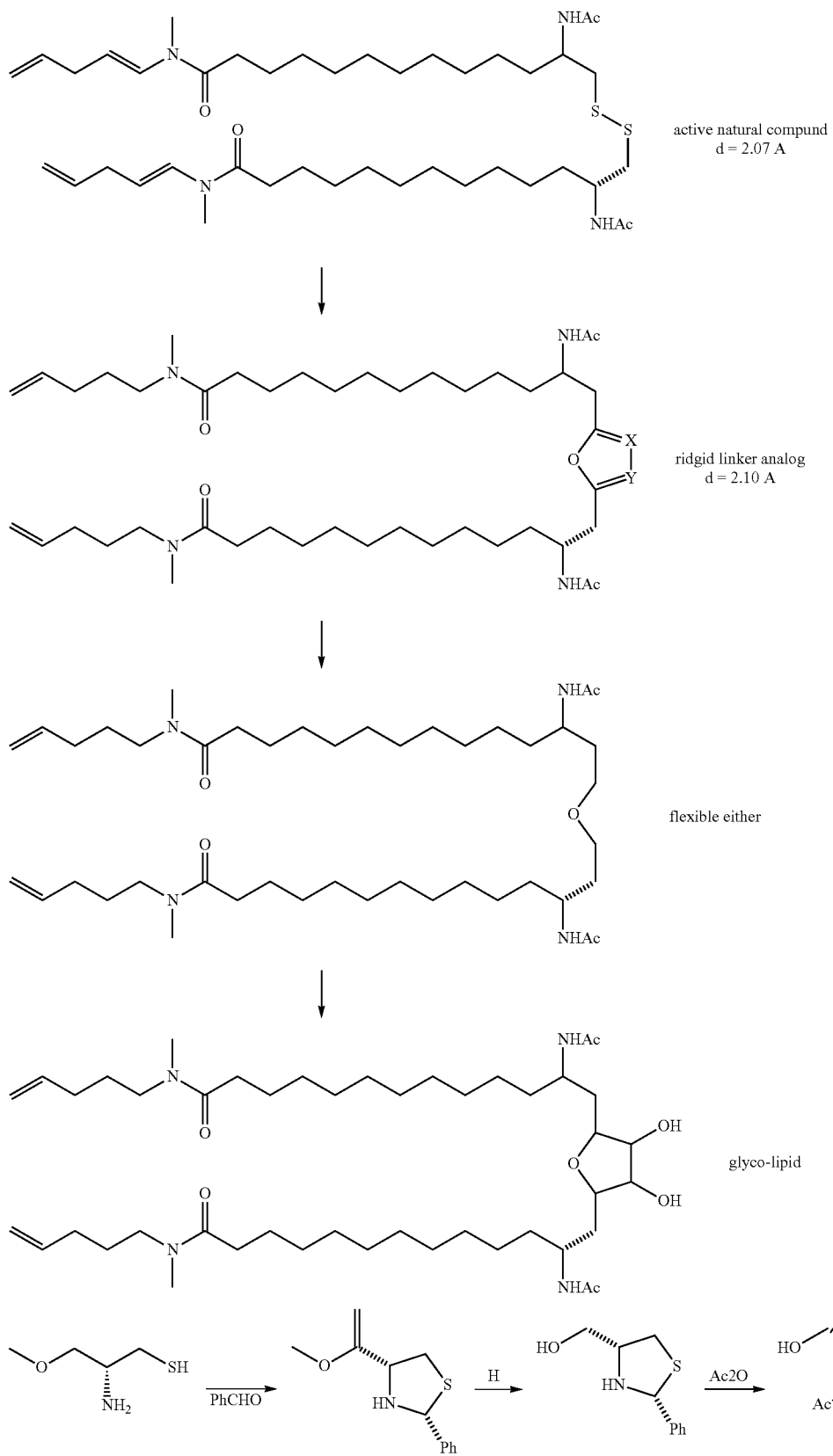
Analoging Natural Compound for Drugability

-continued

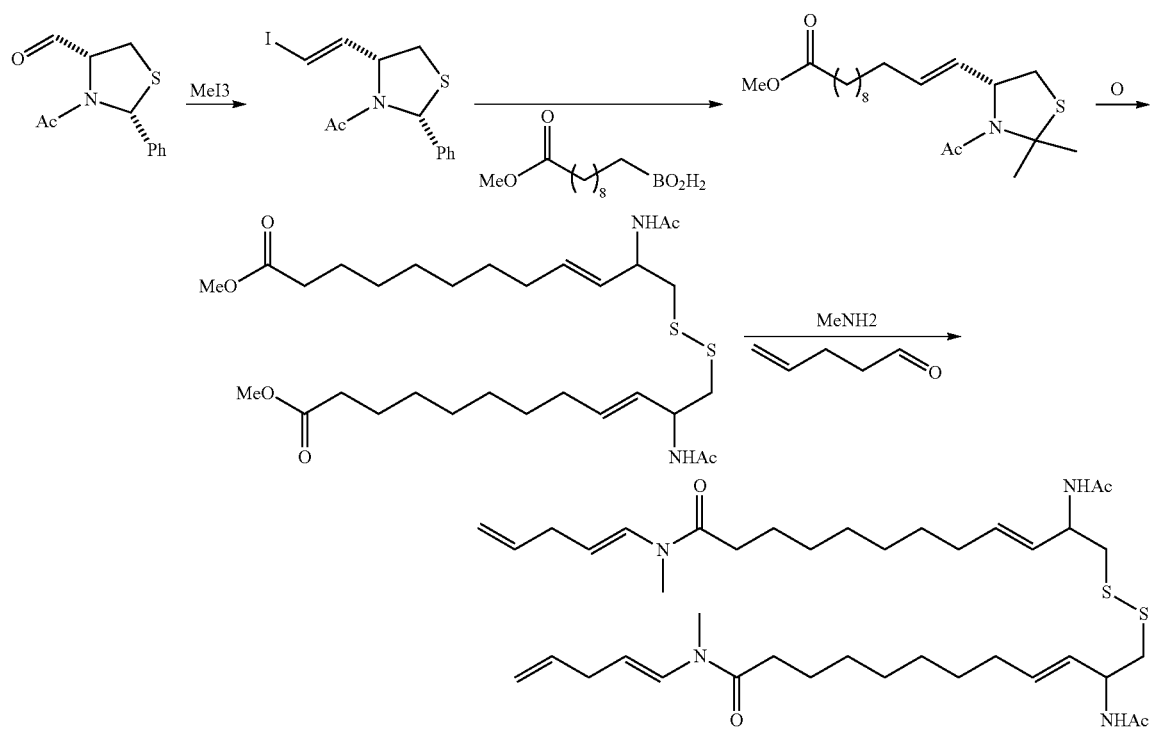

| | A linker length | |
|---|---|---|
| (NHAc-CH-CH2-S-S-CH2-CH-NHAc structure with Lip groups) | 6.31 | Disulfide linker of natural product |
| (ether linkage structure) | 4.77 | simplest flexible, stable ether linkage |
| (ester linkage structure) | 5.01 | NHAc shielded ester linkage (may be esterase cleavable) |
| (ethylene glycol type structure with R1, R2) | 5.93 | ethylene glycol type linkage with R groups for further analoging R1/R2 could be ring structure for inducing ridgidity |
| (diether structure with R3) | 5.51 | ideal flexible linker for phospholipid formation at R3 position |
| (hydrazide linker structure) | 4.67 | flexible hydrazide peptide like linker |

| A linker length | | |
|---|---|---|
| 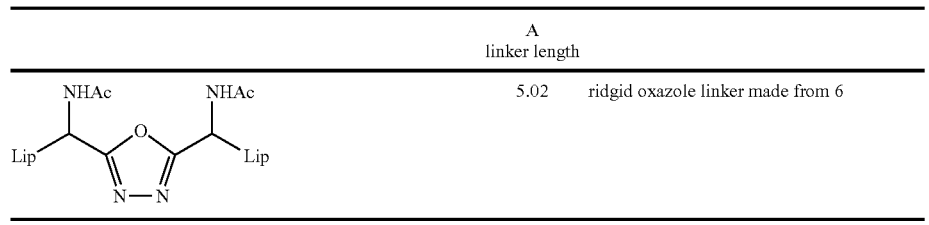 | 5.02 | ridgid oxazole linker made from 6 |

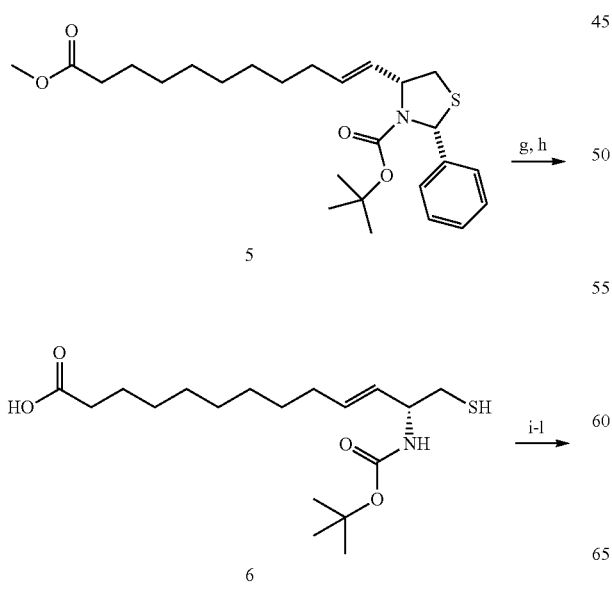

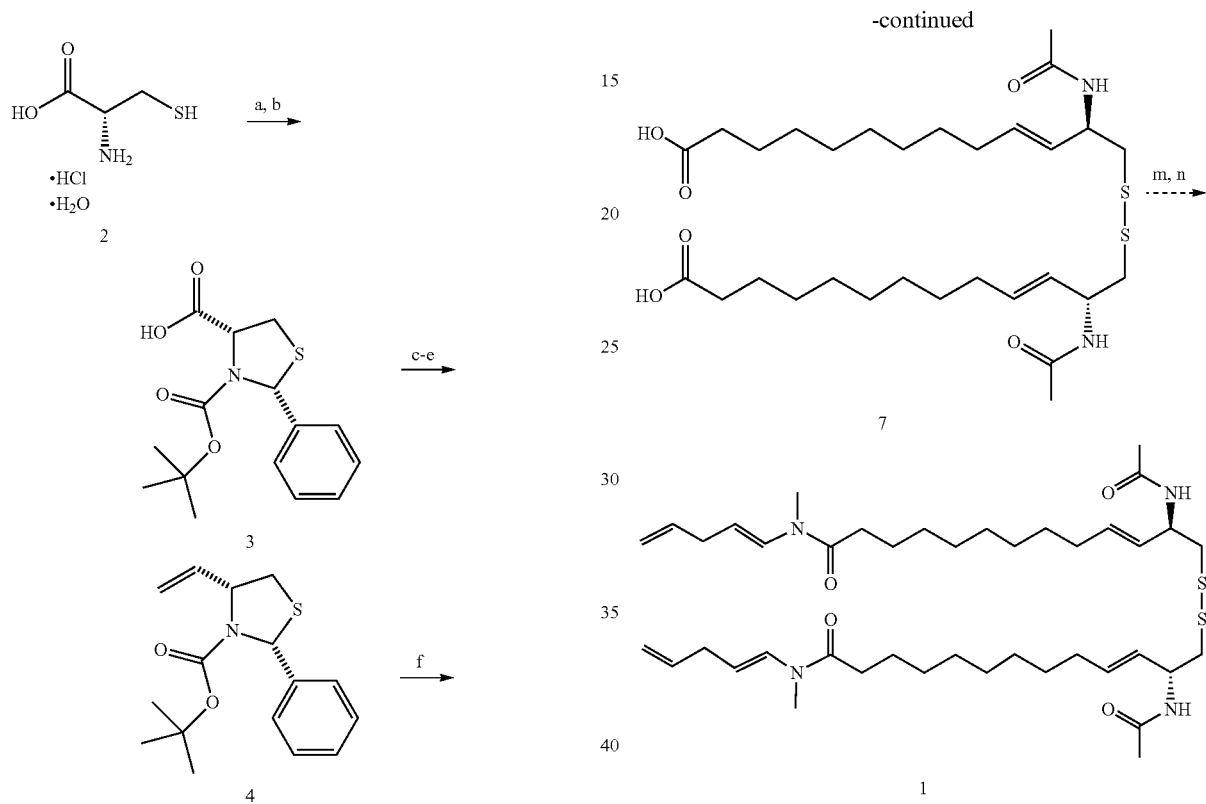

Example 2

Synthetic Schemes for Making Somocystinamide A Lipopeptides and Somocystinamide A Lipopeptide Analogs of the Invention This example describes an exemplary means to synthesize somocystinamide A. L-cysteine is ketide extended with five (5) malonyl CoA derived acetate units, followed by linkage of an N-methyl glycine moiety, and then further extension by two additional acetates. Decarboxylation to produce the terminal olefin and dimerization completes the synthesis.

The invention provides a synthesis scheme to produce gram quantities of somocystinamide A, and starting material for somocystinamide A analogs. The synthetic strategy of the invention allows for simultaneous analoging of derivatives of the somocystinamide A natural compound. Thus using the somocystinamide A natural compound as a design scaffold synthetic analogs of the invention are constructed, which in some embodiments, have improved "drugability", i.e., hydrolytic and proteolytic stability and pharmacological properties.

Example 3

Nanoparticles of the Invention

The invention provides nanoparticles and liposomal membranes comprising the somocystinamide A lipopeptides and analogs of the invention as, e.g., pharmaceutical compositions comprising them.

In one aspect, somocystinamide A lipopeptides and analogs of the invention are incorporated into liposomal membranes to produce stable nanoparticles of about 100 nM in size; these showed full retention of potency in tumor cell lines. The invention also provides nanoparticles of any size, e.g., from anywhere between about 10 to 1000 nM, 50 to 500 nM, or 75 to 250 nM in size.

We have demonstrated that somocystinamide A can be incorporated into liposomal membranes and produced stable nanoparticles of 100 nM in size which showed full retention of potency in tumor cell lines. Further, we have manufactured liposomal nanoparticles which target tumor vasculature via specific ligands (e.g., RGD). The invention provides targeted nanoparticles incorporating the somocystinamide A and its synthetic analogs.

Example 4

Demonstrating the Efficacy of Compounds of the Invention as Apoptotic Cascade-inducing and Anticancer Agents The invention provides nanoparticles and liposomal membranes comprising somocystinamide A lipopeptides and somocystinamide A lipopeptide analogs, including monomeric forms, as discussed herein, as pharmaceutical compositions to treat any condition ameliorated by inhibition of neovascularization, e.g., cancer. While the invention is not limited by any particular mechanism of action, this example discusses alternative mechanisms of action of compounds of this invention.

Action of scA on Tumor Cells.

Somatocystinamide A, or scA (also designated "MCC1144"), is a lipophilic metabolite isolated from seaborne cyanobacteria. From a biological standpoint, scA and analogs can partition into biological membranes and should be able to freely distribute between the inner and outer leaflet of a plasma membrane. scA's sulfur-sulfur bond may be reduced upon exposure to the cytosol, thus permitting the two halves of the scA molecule to dissociate and to act as monomers; and these monomers may have two significant mechanisms of action: first, a monomer might act as an analog of a monomeric bioactive lipid, such as ceramide; second, a monomer might act as a modifying group for cellular components, such as a transmembrane or a membrane associated receptor. Both possible actions may be able to modify the distribution of lipid subdomains, also called "lipid rafts", on the surface of the cells, thus promoting signaling by several cell surface receptors, including, e.g., the so-called "death receptors" which initiate the apoptotic cascade (lipid rafts can be visualized, e.g., by fluorescent microscopy, see, e.g., U.S. Patent App. Pub. No. 20060205760; and compounds can be tested for their ability to interact with a lipid raft, see, e.g., U.S. Patent App. Pub. No. 20060040331—describing methods of screening cellular polypeptides for pro-apoptotic or anti-apoptotic activity; and U.S. Patent App. Pub. No. 20050079507—describing biological membrane microarrays for target evaluation). Structural features of the monomeric molecules are illustrated in FIG. 1b.

Figure 22:
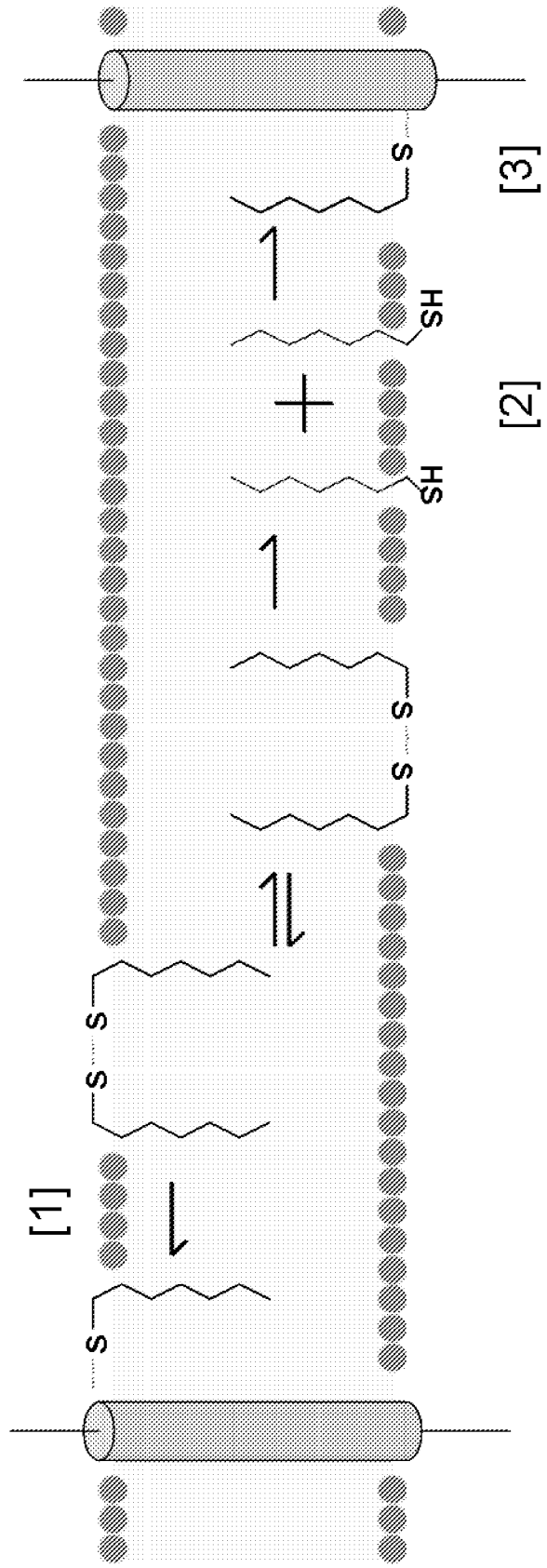
FIG. 22 illustrates an exemplary, possible general principle of action of a compound of this invention, is activation of a so-called "death receptor" to initiate an apoptotic cascade, as described in detail in Example 4, below.

An exemplary, possible general principle of action of a compound of this invention, is activation of a so-called "death receptor" to initiate an apoptotic cascade, is shown in the cartoon illustrated as FIG. 22. In this exemplary model, scA intercalates (inserts) into the outer leaflet of the plasma membrane. At this point, some csA may engage in sulfhydryl exchange with cell surface proteins, possibly disrupting existing disulfide bonds and ultimately altering the lipid microdomain distribution of the cell surface proteins. The scA can also redistribute to the inner leaflet of the membrane, where it is reduced. The monomers can act similar to LPA or short chain ceramides, altering the lipid microenvironment, leading to aggregation of proteins in isolated lipid rafts. In one alternative embodiment, the free sulfhydryl may form disulfide or thioester bonds with transmembrane (or membrane proximal) constituents, such as lipids or proteins, to target the resultant molecules to lipid micro-domains such as "lipid rafts" and initiate "inappropriate" (or appropriate in some circumstances, e.g., if cell death is desired) cell signaling events.

Of these alternative means of action, pre-reduction of scA attenuates an activity, although this mechanism could also reflect competition for scA reactivity by serum components present in the tissue culture media.

Alternative Mechanisms of Action

Figure 23:
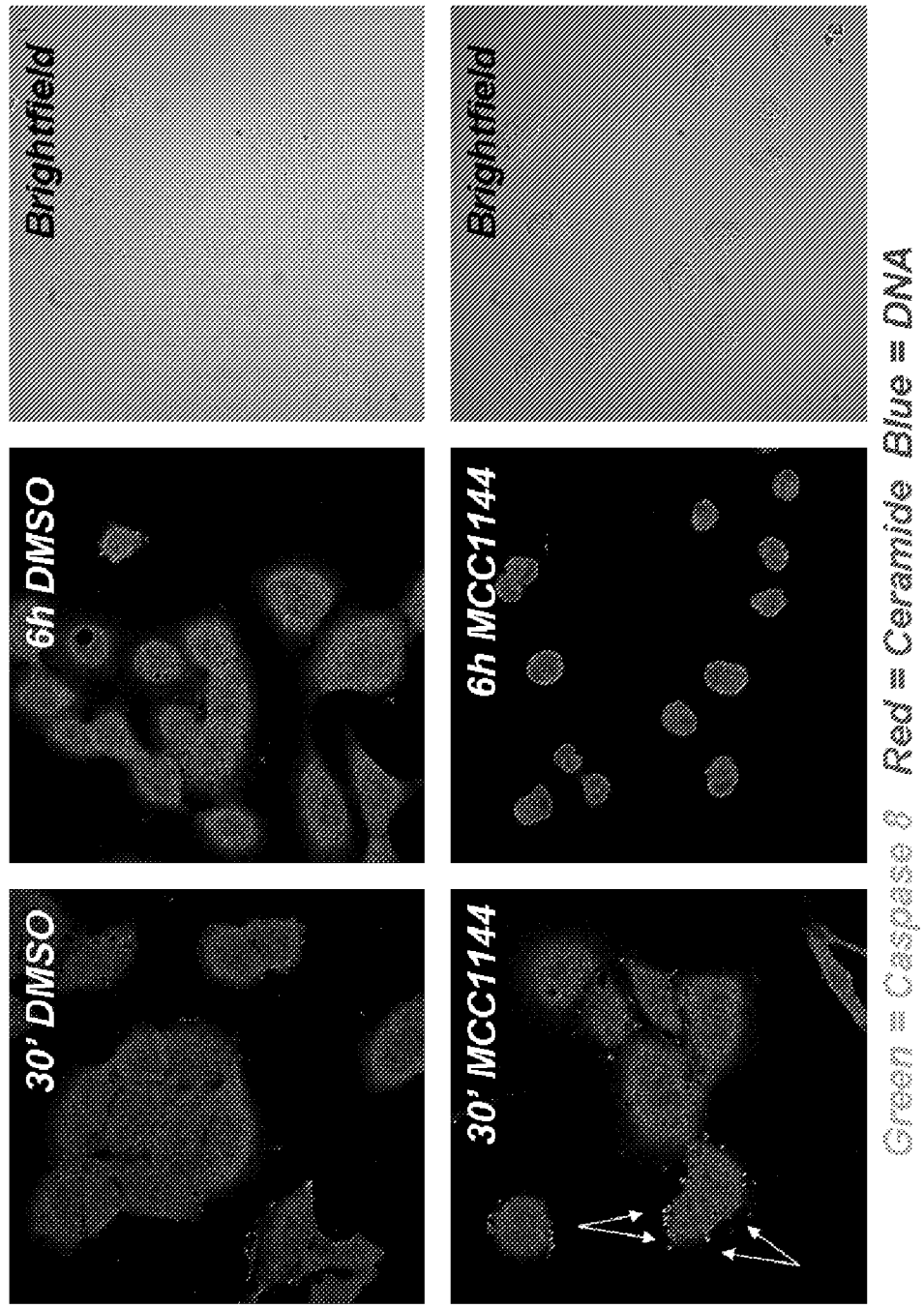
FIG. 23 illustrates confocal microscopy images of cell nuclear shrinkage and rounding induced by somocystinamide A, as described in detail in Example 4, below.

Addition of ScA (MCC1144) to a cell membrane can leads to the extrusion of filapodia, followed by retraction and rounding. Ceramide clusters in rafts, and blebs appear on the cell surface within 15 minutes of contact with the cell membrane, characteristic of apoptosis. As shown in FIG. 23, nuclear shrinkage and rounding are characteristic by 6 hours (after contacting cells with ScA). Interestingly, filapodial remains can still be seen extruded in the shrunken and dying cells.

To examine the mechanistic requirements for this apoptosis, we took two approaches. In the first, we used a neuroblastoma cell line that lacked expression of caspase 8, one of the apical proteases controlling cell survival. We compared the capacity of scA to impair the proliferation of these cells relative to a cell line in which we had reconstituted caspase 8 expression ectopically. We found a 50 fold difference in sensitivity to the apoptosis-inducing activity of ScA, suggesting that it was dramatically enhanced by the presence of caspase 8. This suggests that the drug may act to fire death receptors as well as other cell membrane signaling molecules, e.g., such as those that control cell ruffling or filapodia extension.

Figure 24:
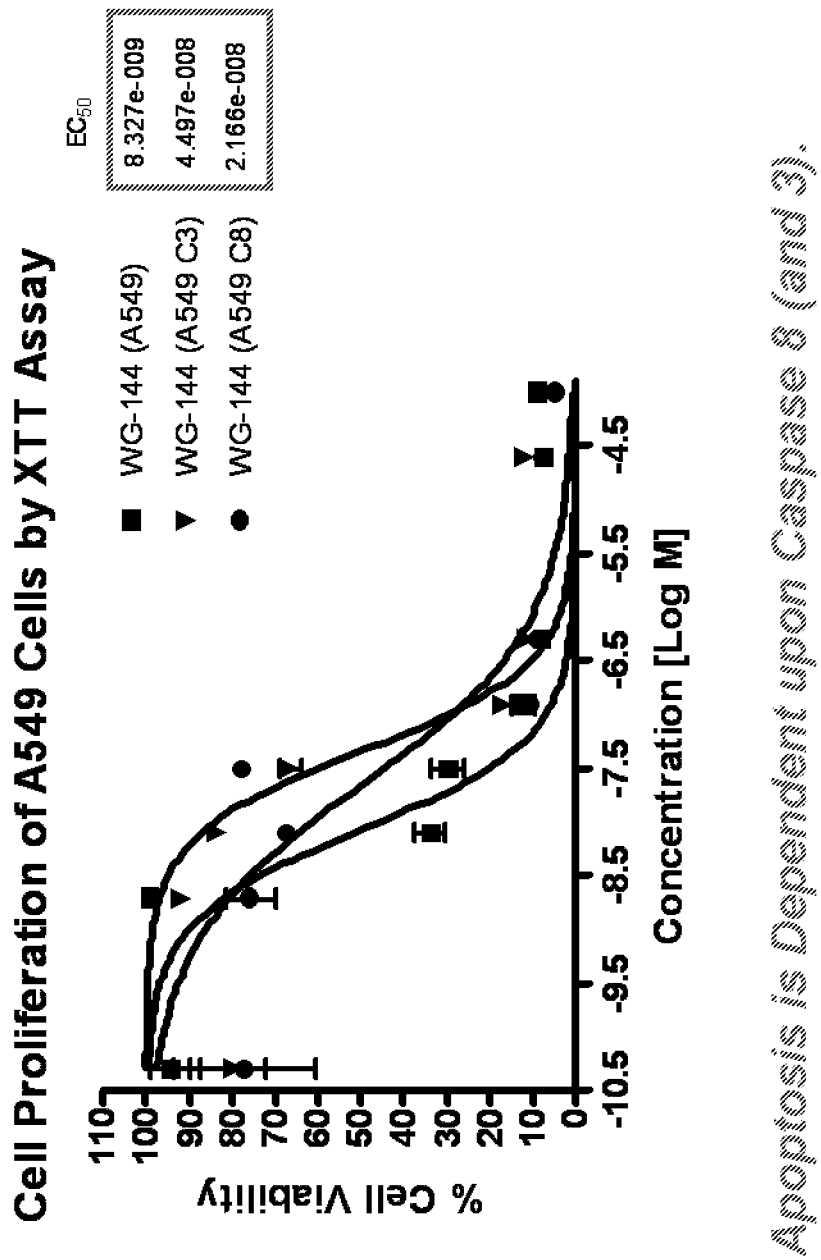
FIG. 24 graphically illustrates data showing the effects of ScA on cells that have either been infected with caspase 8-expressing lentivirus or caspase 3-expressing lentivirus, as described in detail in Example 4, below.

To confirm these studies, we next generated a lentivirus vector encoding shRNA to silence the expression of caspase 8 and its downstream target, caspase 3 in A549 lung cancer cells. Infection of the cells with either lentivirus (caspase 8-expressing and caspase 3-expressing) was sufficient to attenuate the pro-apoptotic response induced by scA (see data graphically illustrated in FIG. 24), confirming that the extrinsic death pathway is a principle mediator of scA mediated killing. Nonetheless, killing is still observed in cells lacking caspase 8, suggesting that csA has ancillary mechanism of action, particularly as one approaches higher concentrations, e.g., in the nanomolar range. The results demonstrate that scA is a potent mediator of tumor cell and endothelial cell apoptosis.

In summary, while the invention is not limited by any particular mechanism of action, this example discussed alternative mechanisms of action of compounds of this invention, including reduced and unreduced forms of scA and its analogs.

Example 5

Synthetic Scheme for Making Somocystinamide A Lipopeptides and Somocystinamide A Lipopeptide Analogs of the Invention The invention provides compositions comprising somocystinamide A lipopeptides and somocystinamide A lipopeptide analogs, including monomeric forms, as discussed herein, and pharmaceutical compositions comprising these compounds. This example describes exemplary methods for making selected compositions of this invention.

Figure 25:
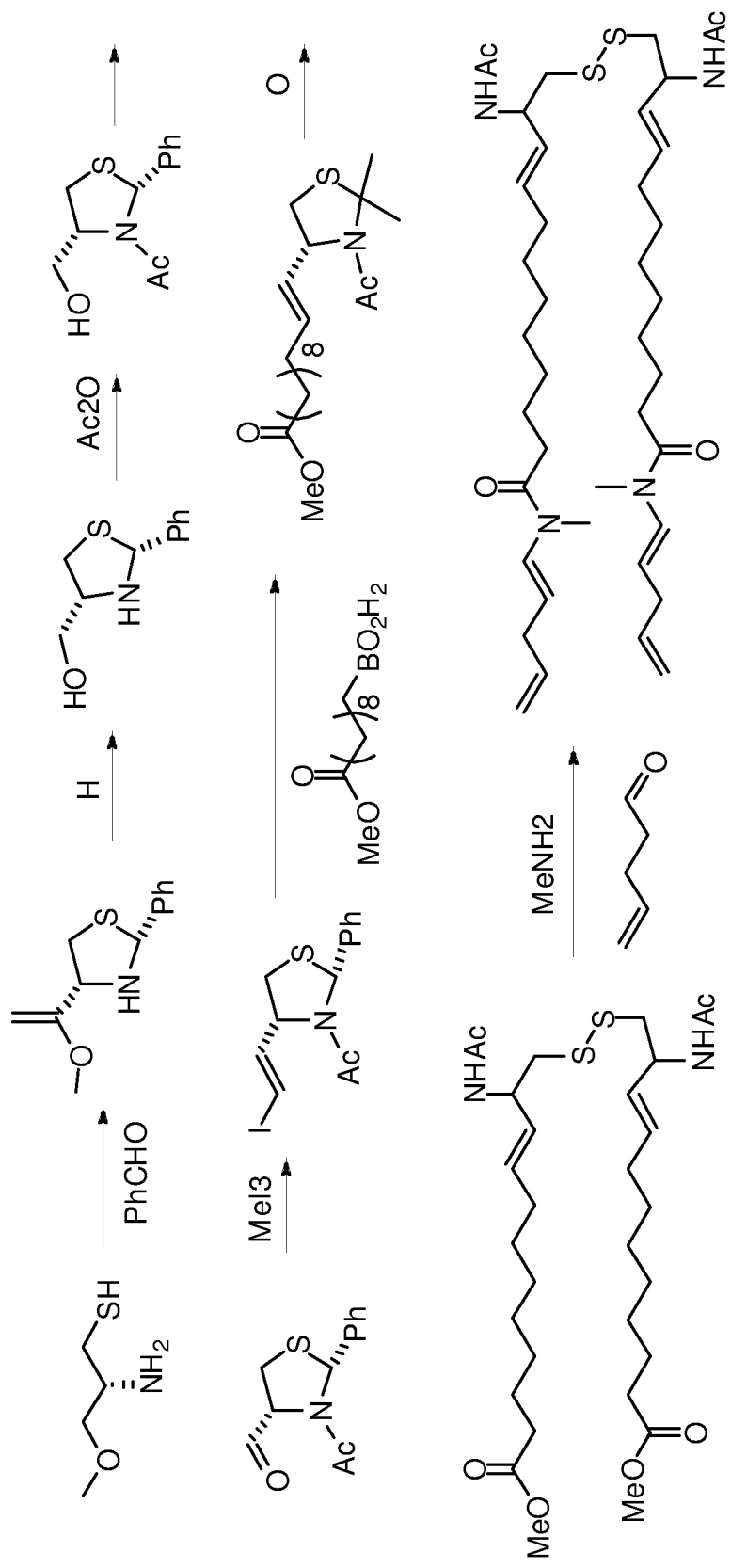
FIG. 25(a) illustrates an exemplary total synthesis of somocystinamide A.
FIG. 25(b) illustrates an exemplary synthetic strategy for alternative exemplary compounds of this invention—the somocystinamide A analogs of the invention, as described in detail in Example 5, below.
Figure 25:
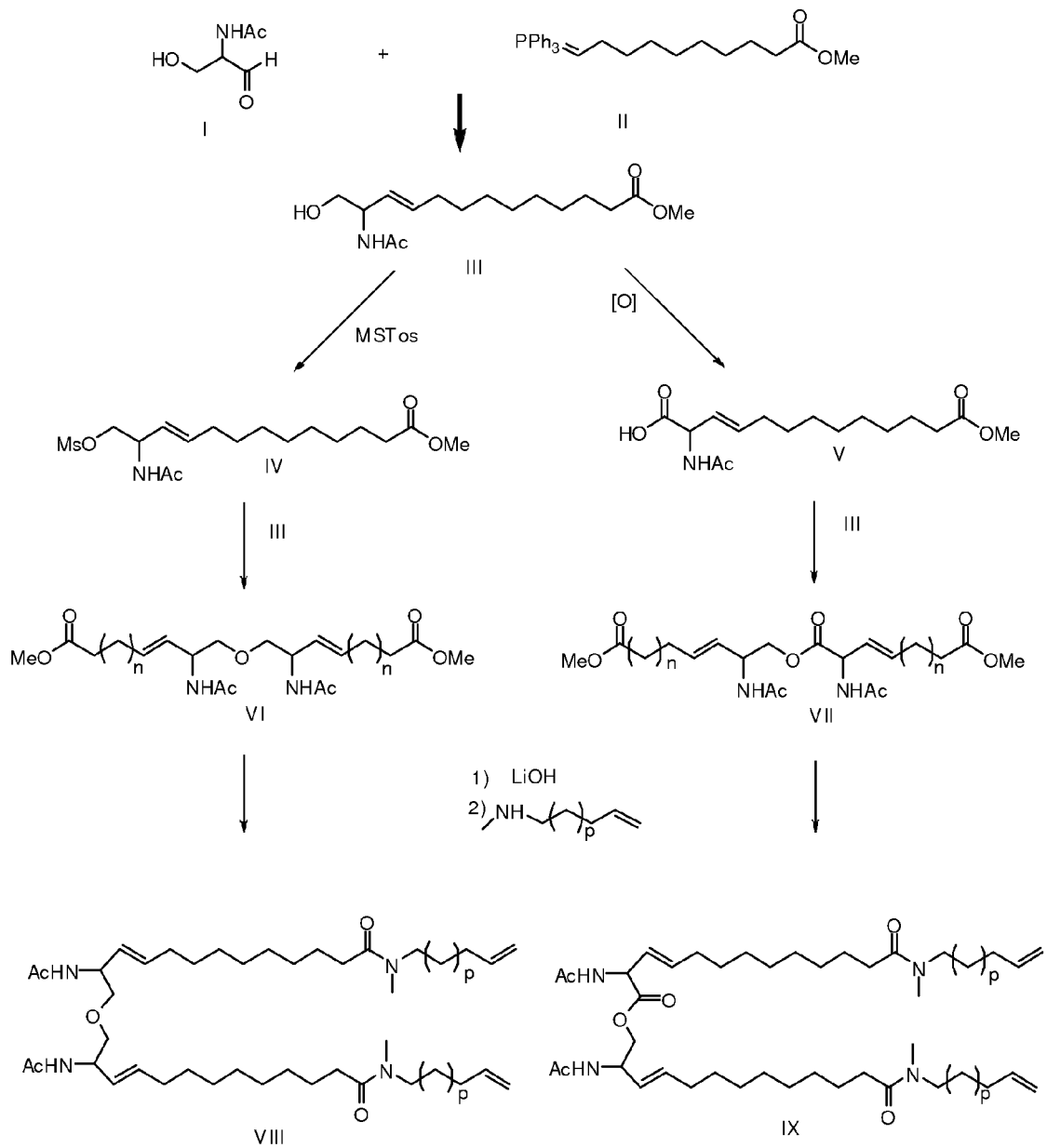

In alternative embodiments, the procedures illustrated in FIG. 25a and FIG. 25b can be used to obtain (generate) gram quantities of compounds of the invention; and this protocol can be optimized for yield.

In another embodiment, the invention provides methods comprising use of somocystinamide A as a pharmacophore for the design of various analogs, and the invention provides methods for making somocystinamide A lipopeptide analogs comprising alternative methods of making somocystinamide A lipopeptide. Exemplary rationale for making the various analogs of this invention, as described herein ("analoging" somocystinamide A lipopeptide) are 1) to address potential in vivo pharmacological stability issues of the somocystinamide A lipopeptide natural product (i.e. disulfide bridge and ene group next to the N-methylamide; 2) to expand the structural diversity of the natural compound; and, 3) to gain further insight into which structural features of a molecule of this invention contributes to its potency.

FIG. 25(a) illustrates an exemplary total synthesis of somocystinamide A; and FIG. 25(b) illustrates an exemplary synthetic strategy for alternative exemplary compounds of this invention—the so-called "somocystinamide A analogs" of the invention. FIG. 26 illustrates alternative exemplary compounds of this invention having, e.g., different linkers, which can be used for the further synthesis of new analogs.

This exemplary synthetic scheme starts with the commercially available compounds I and II (see FIG. 25a and FIG. 25b); intermediate III is synthesized, which upon further reaction results in versatile heterobifunctional intermediates IV and V.

Reaction of exemplary compounds IV and V with III yield further exemplary lipids of this invention comprising either ether or shielded ester linkages. Alternatively, exemplary compounds III and IV can be used to generate exemplary compounds of this invention having lipid structures with different linker moieties, as exemplified in FIG. 26. Further reactions of exemplary compounds VI and VII can yield of exemplary compound products comprising hydrolytically stable amide segments. Using this exemplary synthetic strategy outlined in FIG. 25a and FIG. 25b, the lipid component of the molecule also can be further modified to make the exemplary compounds of this invention having either shorter or longer hydrocarbon chains, n and p.

Example 6

Synthetic Scheme for Making Somocystinamide A Lipopeptides and Somocystinamide A Lipopeptide Analogs of the Invention The invention provides compositions comprising somocystinamide A lipopeptides and somocystinamide A lipopeptide analogs, including monomeric and dimeric forms, as discussed herein, and pharmaceutical compositions comprising these compounds. This example, as illustrated in FIG. 27, a schematic illustrating a synthetic scheme for making somocystinamide A lipopeptides and somocystinamide A lipopeptide analogs of the invention, details an exemplary method for making selected compositions of this invention.

Figure 27:
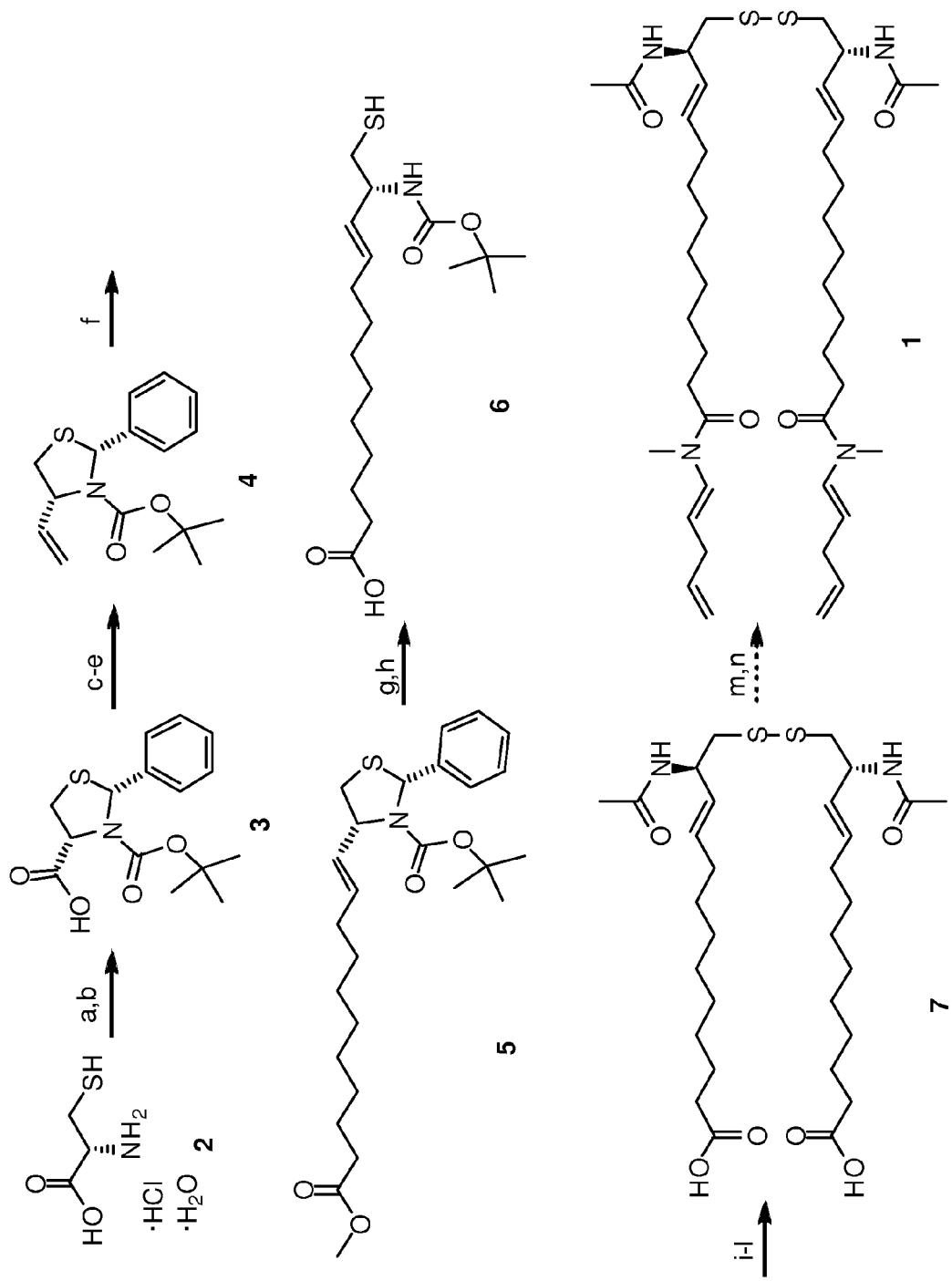
FIG. 27, a schematic illustrating a synthetic scheme for making somocystinamide A lipopeptides and somocystinamide A lipopeptide analogs of the invention, details an exemplary method for making selected compositions of this invention, as described in detail in Example 6, below.

In FIG. 27: a) PhCHO, EtOH/$H_2O$. b) $Boc_2O$, NaOH, dioxane/$H_2O$, 66% over 2 steps. c) $BH_3.Me_2S$, THF, 94%. d) $(COCl)_2$, DMSO, $Et_3N$, $CH_2Cl_2$, 92%. e) $Ph_3PCH_3.Br$, n-BuLi, THF, 62%. f) methyl 10-octenoate, $2^{nd}$ generation Hoveyda catalyst, $CH_2Cl_2$, 81%. g) LiOH, $H_2O$/THF. h) Na, $NH_3(l)$, 93% over 2 steps. i) $CH_2N_2$, $Et_2O$/MeOH, 66%. j) TFA, $CH_2Cl_2$. k) $Ac_2O$, $Et_3N$, $CH_2Cl_2$, 85%. l) LiOH, $H_2O$/THF, 100%. m) $(COCl)_2$, DMF, $CH_2Cl_2$. n) $MeNH_2$, 4-pentenal, pyridine, $CH_2Cl_2$.

The synthesis of somocystinamide A (1) begins with cysteine that is fully protected at amino and thiol groups (3). The carboxylic acid is reduced to an alcohol and is then oxidized back to an aldehyde, which is transformed to an olefin via a Wittig reaction. Ruthenium catalyzed metathesis of the olefin (4) with methyl 10-octenoate yields the trans olefin 5 in good yield. The benzaldehyde protecting group is reductively cleaved off by the treatment with sodium metal in liquid ammonia (6). Upon methylation, deprotection of the Boc group, acetylation, and basic hydrolysis, the dimeric acetamide (7) is obtained. This material is treated with oxalyl chloride to form the acid chloride, which is then coupled to the in-situ generated imine to obtain the somocystinamide A lipopeptide (1).

Example 7

Identifying Compounds of the Invention as Anticancer Agents and Demonstrating their Efficacy The invention provides compositions comprising somocystinamide A (ScA) lipopeptides and ScA lipopeptide analogs, including monomeric and dimeric forms, as described and illustrated herein, and pharmaceutical compositions comprising these compounds.

By screening for novel anticancer drugs in chemical libraries isolated from marine organisms, we identified the lipopeptide somocystinamide A (ScA) as a pluripotent inhibitor of angiogenesis and tumor cell proliferation. While the invention is not limited by any particular mechanism of action, the anti-proliferative activity of ScA was due largely to induction of programmed cell death, or apoptosis.

Sensitivity to ScA was significantly increased among cells expressing caspase 8, while siRNA knockdown of caspase 8 increased survival following exposure to ScA. ScA rapidly and efficiently partitioned into liposomes while retaining full antiproliferative activity. Consistent with the induction of apoptosis via the lipid compartment by ScA, we noted accumulation and aggregation of ceramide in ScA-treated cells, and subsequent co-localization with caspase 8. Angiogenic endothelial cells were extremely sensitive to ScA. Picomolar concentrations of ScA disrupted proliferation and endothelial tubule formation in vitro. Systemic treatment of zebrafish or local treatment of the chick chorioallantoic membrane with ScA resulted in dose-dependent inhibition of angiogenesis, while topical treatment with ScA blocked tumor growth among caspase 8-expressing tumors. Together, the results reveal an unexpected mechanism of action for this novel lipopeptide of this invention and its analogs as described herein, and demonstrate their efficacy as anti-angiogenesis and anti-cancer drugs.

We had previously reported that ScA isolated from mixed assemblage *L. majuscala/Schizothrix* species yielded cytotoxic effects against a murine neuroblastoma cell line (11). These studies were somewhat limited by the relatively low abundance of this compound.

Results

ScA Induces Apoptosis Selectively via Caspase 8. In continuing investigations, we now document that freshly isolated ScA shows potent anti-proliferative activity against a number of human tumor cells (Table 1). Microscopic examination reveals that the loss of proliferation is associated with a "blebbing" morphology, as illustrated in FIGS. 28A and 28B, while biochemical analysis revealed proteolytic processing of cellular proteins such as caspase 8 and PARP that are hallmark indicators of apoptosis, as illustrated in FIG. 28C.

To determine if caspase 8 expression could account for increased ScA activity, we examined the ability of ScA to induce apoptosis in wild type Jurkat cells or those deficient in caspase 8. Compared to wild type cells, apoptosis was dramatically decreased among caspase 8-deficient Jurkat cells exposed to ScA, as illustrated in FIG. 28D. Extending these studies, we knocked down expression of caspase 8 (knocked down approximately 80% of its activity) using short hairpin RNA approach in the A549 cell line, and found a five-fold loss in sensitivity to ScA, as illustrated in FIG. 28E. Finally, we also tested NB7 neuroblastoma tumor cell, which are deficient for caspase 8 expression, as well as the matched sister line, NB7C8, which is reconstituted for physiological levels of C8 expression (12). In this case, the expression of caspase 8 increased the potency ($IC_{50}$) of ScA by fifty fold, as illustrated in FIG. 28F. The results implicate caspase 8 as an effector of apoptosis following ScA treatment.

In summary, tumor cell lines, with types as listed, were tested for their capacity to proliferate in the presence of ScA. The dose at which a 72 hour proliferation was reduced to half that of diluent-treated controls, as measured by a standard XTT assay, is shown. FIG. 28A to F illustrates ScA can induce apoptosis selectively via caspase 8 dependent mechanisms.

Figure 28:
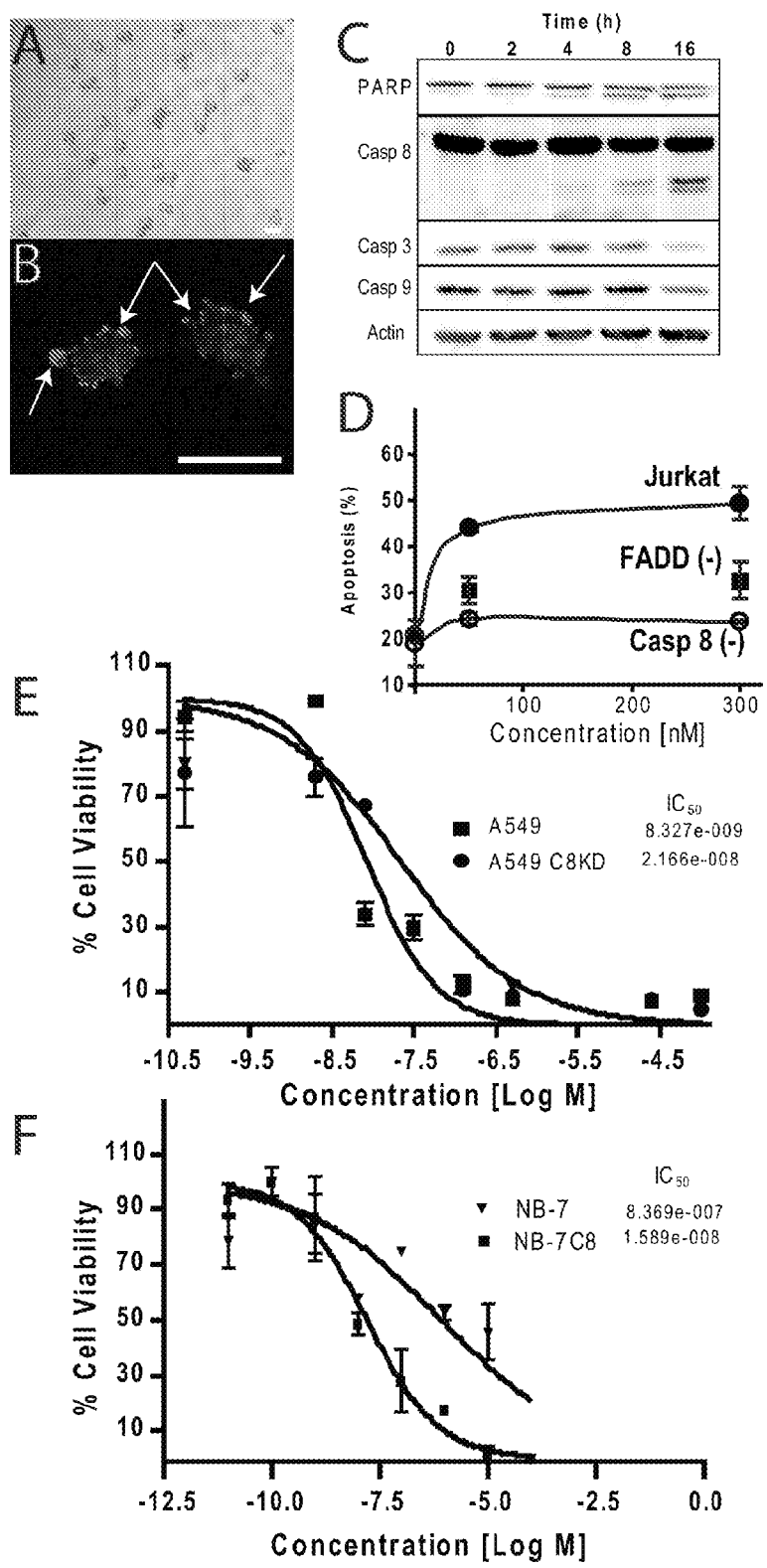
FIG. 28(A) illustrates an observed in via bright field microscopy showing the results of treatment of A549 cells with 100 nM ScA, and that it induces a blebbing morphology.
FIG. 28(B) illustrates a photomicrograph of A549 cells fixed and co-stained using antibodies directed against ceramide (red channel), where the nuclear compartment was visualized using DAPI to stain DNA (blue channel)
FIG. 28(C): illustrates an immunoblot analysis of Jurkat cells performed following treatment with 100 nM ScA, where cell lysates were probed for caspases 8, 3 and 9 and for PARP and actin.
FIG. 28(D) graphically illustrates data showing caspase 8 deficient (Casp 8), FADD deficient (FADD –) or parental Jurkat cells (Jurkat) after incubation with 50 or 300 nM for 6 hours, where the analysis is for the presence of apoptotic cells via FACs analysis of DNA content.
FIG. 28(E) graphically illustrates data showing A549 cells subjected to lentivirus-delivered shRNA-mediated knockdown of caspase 8, or treated with a scrambled shRNA lentivirus, where cells were then cultured in the presence of increasing doses of ScA.
FIG. 28(F) graphically illustrates data showing the viability of neuroblastoma cultures deficient in caspase expression, or reconstituted for caspase 8 expression, as described in detail in Example 7, below.

FIG. 28(A): Treatment of A549 cells with 100 nM ScA induces a blebbing morphology, as observed in via bright field microscopy. FIG. 28(B): A549 cells were fixed and costained using antibodies directed against ceramide (red channel) (Bars in A/B=25 µM). Arrows indicate regions of "blebbing." The nuclear compartment was visualized using DAPI to stain DNA (blue channel). The assessments were performed two hours after treatment with 300 nM ScA. FIG. 28(C): Immunoblot analysis of Jurkat cells was performed following treatment with 100 nM ScA. 25 µg of cell lysates was probed for caspases 8, 3 and 9 and for PARP and actin (loading control) as indicated. FIG. 28(D): Caspase 8 deficient (Casp 8), FADD deficient (FADD −) or parental Jurkat cells (Jurkat) were incubated with 50 or 300 nM for 6 hours and analyzed for the presence of apoptotic cells via FACs analysis of DNA content. Results shown are the mean and standard error of triplicate determinations. FIG. 28(E): A549 cells subjected to lentivirus-delivered shRNA-mediated knockdown of caspase 8, or treated with a scrambled shRNA lentivirus. Cells were then cultured in the presence of increasing doses of ScA, as indicated. Viability was measured by XTT assay after 72 hours, and normalized to controls not treated with drug. FIG. 28(F): similarly, the viability of neuroblastoma cultures deficient in caspase expression, or reconstituted for caspase 8 expression, was determined as for the A549 cells above. Both experiments are representative, with each point shown the mean±SE of triplicate wells.

Caspase 8 is an effector of death receptor (DR)-mediated apoptosis following death receptor ligation by an appropriate agonist . This triggers the recruitment of the adaptor protein FADD and subsequent formation of the death-inducing signaling complex (13). Accordingly, Jurkat cells lacking FADD were protected from ScA-mediated killing, see FIG. 28D, implicating DR-mediated killing in this process. However, NB7C8 cells are resistant to DR-mediated killing (12), and similarly A549 cells do not undergo Fas-mediated apoptosis (14), although both cell lines were sensitive to ScA-induced killing. In agreement with these results, the addition of the Fas agonist CH11 did not cooperate with ScA to promote cell death. However, death receptor "ligation" is not strictly required for apoptosis induced by death receptors, rather, it appears that ligand-mediated redistribution of membrane components may be critical for death (15-17).

ScA partitions into phospholipids and alters membrane structure. The invention provides liposomes comprising compositions of this invention, including methods for using them, e.g., for the delivery of compositions of this invention as drugs via liposomes, e.g., using liposomes carriers as described in (18).

As ScA and other ScA-based compositions of this invention are lipophilic compounds (ScA with a logP=10.3), we assessed the capacity of ScA to partition from liquid phase into 100 nanometer liposomes (nanosomes). Interchelation of ScA within the nanosomes was essentially complete within thirty minutes, with no residual unincorporated drug detected.

Testing whether the liposome-borne ScA maintained cytotoxic activity, we found that apoptosis induced by treatment of cells with ScA nanosomes mimicked treatments with ScA as a "free" compound, as illustrated in FIG. 29B. Treatment with control, unloaded nanosomes had no effect on cell viability. Together, these results demonstrate the efficacy of nanoparticle-based, e.g., nanosome-based or lipid-based, delivery of compounds of this invention to cells in vitro, ex vivo or in vivo, including ScA and the ScA-based compounds of this invention. These data also implicate the lipid compartment in ScA-mediated cell death.

It is known that alterations to the cell lipid compartment can promote caspase-mediated cell killing. For example, ceramide-enriched membrane domains can promote death receptor clustering and activation of caspase 8 (17, 19, 20), while treatment with arachidonic acid can mediate caspase 3-dependent cell death (Cao et al. 2000). We examined the A549 cells for evidence of alteration to the lipid compartment following exposure to ScA. We observed an accumulation, and aggregation, of cell surface ceramide (FIG. 29B, red channel) which was absent among cells treated with diluent (unpublished observations) or those treated with arachidonic acid (control) (FIG. 29B). While the invention is not limited by any particular mechanism of action, this result supported the notion that ScA acted via alterations to the plasma membrane.

To evaluate whether observed alterations to membrane lipid distribution corresponded to interactions with apoptotic effectors, in particular caspase 8, we next examined whether these aggregated "clusters" of ceramide in the membrane co-localized with this caspase (FIG. 29B, green channel, colocalization is shown in the yellow channel). The results supported the notion that ScA partitions within cell membranes, alters the lipid compartment and induces the external death pathway in susceptible cells.

Although ceramide was used as a reporter of changes within the organization of the lipid compartment, it remains unclear which lipids (if any) directly contribute to apoptosis. However, it was not simply the lipophilic nature of ScA which resulted in pro-apoptotic activity. ScA is a disulfide-linked lipopeptide dimer (FIG. 29C), and in parallel structure-function studies we found that individual monomers retained essentially no ability (<0.1% potency) to induce apoptosis. Similarly, chemical modification of either the lipopeptide tail of the molecule or manipulations of the disulfide bond abrogated all tumoricidal activity of the compound. Thus, the combination of lipo-peptide dimer and disulfide moieties appears critical to ScA activity.

Figure 29:
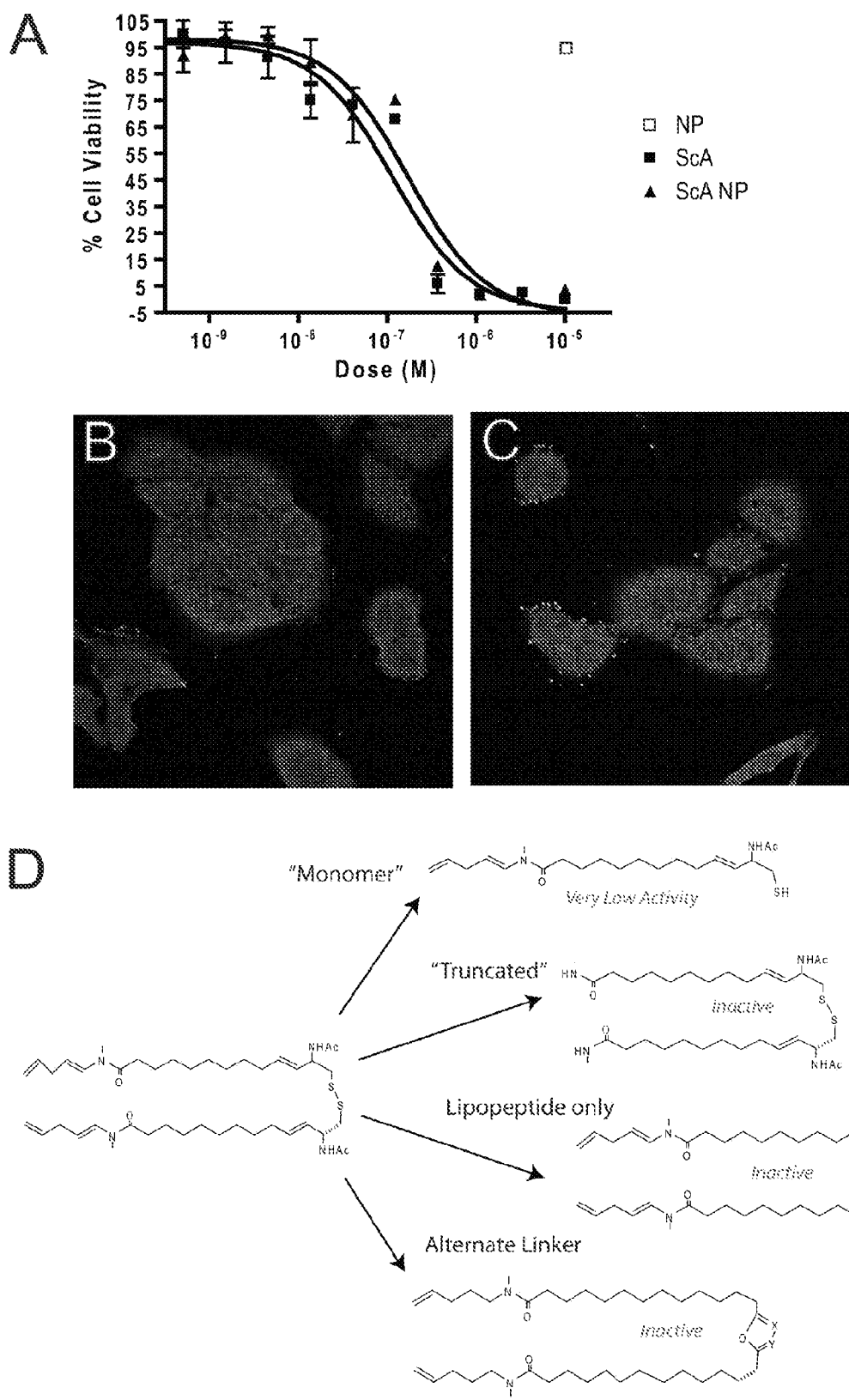
FIG. 29 illustrates data showing that ScA partitions into the lipid compartment.

In summary, FIG. 29 illustrates data showing that ScA partitions into the lipid compartment. FIG. 29(A) graphically illustrates data of cell viability assessed by XTT assays, where ScA was mixed with DOPE:cholesterol:DSPC:DSPE-mPEG to form liposomes, A549 cells were cultured with "free" ScA added in DMSO diluent or with ScA incorporated into nanosomes, and cell viability assessed by XTT assay.

FIG. 29B and FIG. 29C illustrate an image of A549 cells stained with anti-ceramide (red Channel) DAPI (blue channel) and anti-caspase 8 (green channel) 30 minutes after treatment with 300 nM arachidonic acid, a control lipid, FIG. 29(B) or 300 nM ScA FIG. 29(C), colocalization of the green and red channels is shown by the merge (yellow signal).

FIG. 29(D) illustrates a limited structure-function analysis of the required elements for ScA (shown at left) activity, where derivatives of ScA synthesized or derived included a "monomeric" form (with less than 0.1% activity), and forms in which the disulfide was replaced with alternative linkers, which showed no activity below 50 µM. A "truncated" lipopeptide which maintained the disulfide linkage also lacked activity below 50 µM. As illustrated in FIG. 29(D), the ScA monomer analog had activity, but relatively "lower" activity, the truncated form of ScA analog had no activity (at least by this assay), the "lipopeptide only" form of ScA analog had no activity (at least by this assay), and the "alternative" form of ScA analog had no activity (at least by this assay).

Anti-angiogenic and anti-tumoral effects of ScA. The compositions of the invention are cytotoxic for angiogenic cells, including angiogenic endothelial cells; thus, the compositions and methods of the invention are used to ameliorate dysfunctional angiogenesis, including blood vessel growth associated with cancers (tumors). Angiogenic endothelial cells are susceptible to apoptosis initiated by caspase 8 (20-22). We therefore tested the effect of ScA treatment on endothelial cells in vitro and in vivo. Cultured endothelial cells were extremely sensitive to ScA (FIG. 3A), with an $IC_{50}$ in the picomolar range. In agreement with these results, we found that ScA potently blocked endothelial cell tube formation in vitro, as illustrated in FIG. 30B, demonstrating that ScA and ScA-based compositions of the invention (e.g., disulfide-linked lipopeptide dimers of the invention) can act both on endothelial and on tumor cells in vitro, ex vivo, and in vivo.

Figure 30:
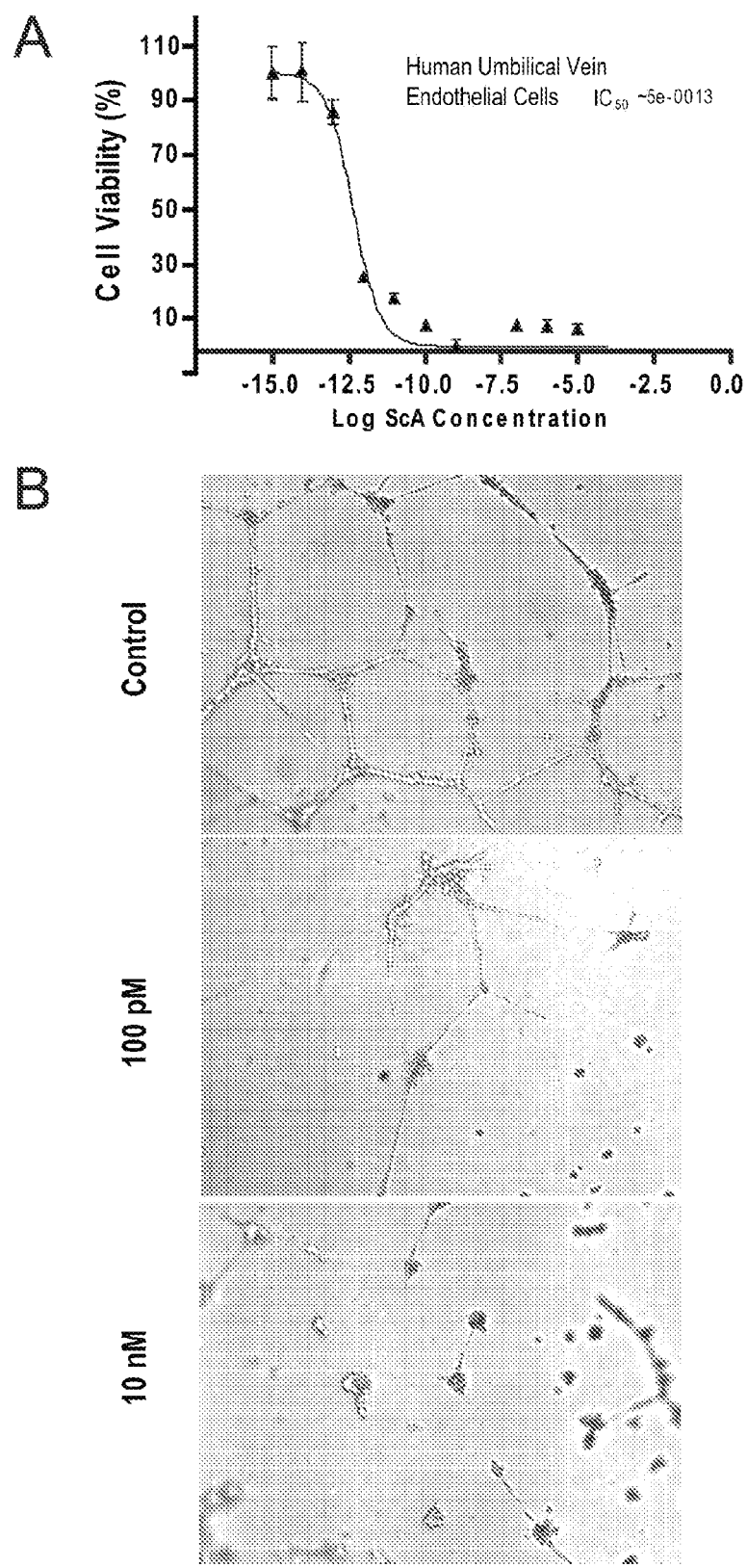
FIG. 30 illustrates data showing that endothelial cells are highly sensitive to ScA, and other ScA-based compositions of the invention.

In summary, FIG. 30 illustrates data showing that endothelial cells are highly sensitive to ScA, and other ScA-based compositions of the invention. FIG. 30(A) graphically illustrates data showing the results of an XTT assay, where human endothelial cells were incubated with ScA at decreasing concentrations, as shown in the figure, and viability assessed by XTT assay after 72 hours, data shown are the mean±SE of triplicate wells from a representative experiment. FIG. 30(B): Human endothelial cells were plated on Matrigel-coated surfaces, and allowed to form tubules for 48 hours in the presence of DMSO diluent (upper panel). When ScA was added (lower panels) cell viability was compromised, and endothelial cell tube formation was disrupted in dose-dependent manner.

Figure 31:
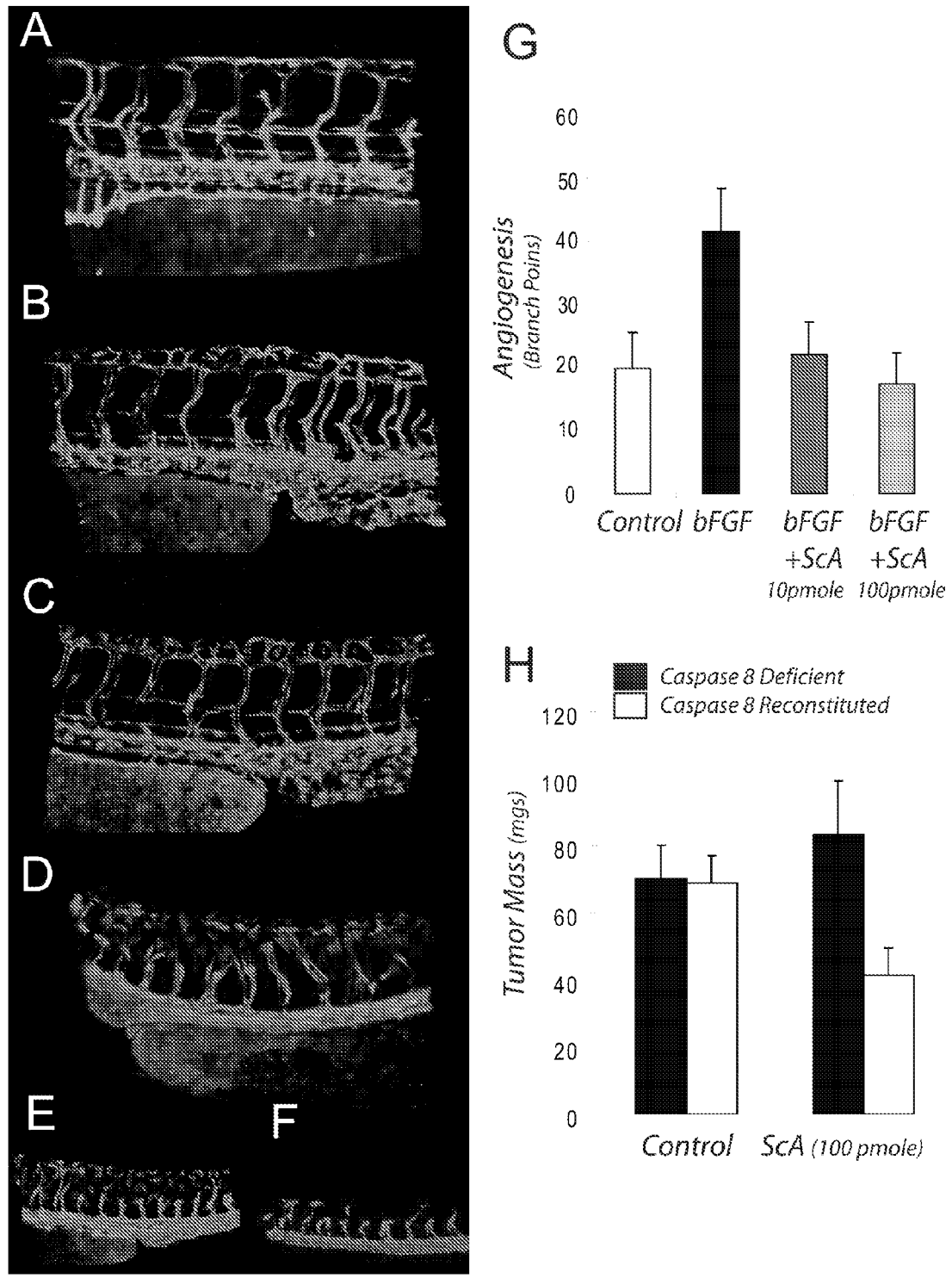
FIG. 31 illustrates data demonstrating the antiangiogenic and antitumor activity of ScA compositions of the invention.

We first examined whether systemic exposure to ScA blocked developmental angiogenesis in zebrafish. During development of the zebrafish, intersegmental vessels sprout and grow upwards from the dorsal aorta, and then the tips join to form a dorsal vein, as illustrated in FIG. 31. In a dose-dependent manner, as illustrated in FIGS. 31B-F, ScA blocked blood vessel growth and angiogenesis, although all of the fish remained viable during the 24 hour period of the study. Similarly, local introduction of ScA into the chick chorioallantoic membrane potently blocked growth factor-induced angiogenesis, as illustrated in FIG. 31G. The results demonstrate the sensitivity of endothelial cells to ScA in vivo, in agreement with our observations in vitro, and indicate that ScA acts as an anti-angiogenic agent in vivo.

In summary, FIG. 31 illustrates data demonstrating the antiangiogenic and antitumor activity of ScA compositions of the invention. FIG. 31(A-F): Transgenic Tg(fli1:EGFP) zebrafish embryos in which GFP is expressed in endothelial cells were incubated without (A) or with increasing concentrations of ScA: 80 nM in FIG. 31(B), 160 nM in FIG. 31(C), 300 nM in FIG. 31(D) 1.6 µM in FIG. 31(E) or 3 µM in FIG. 31(F), and blood vessel morphology recorded by fluorescence microscopy. FIG. 31(G) Filter disks impregnated with 100 ng of bFGF were placed on the chorioallantoic membrane of eleven day old chicks to induce angiogenesis in the absence or presence of ScA, as shown. After 72 hours (h), disks were removed and the vascularity of the underlying chorioallantoic membrane determined by direct counting of branch points using a dissecting microscope. FIG. 31(H): NB7 neuroblastoma cells lacking caspase 8 (filled bar) or NB7-C8 cells reconstituted for caspase 8 expression (open bars) were seeded into ten day old chick chorioallantoic membranes to form tumors. After 72 hours, ScA was added topically to each growing tumor mass. Tumors were harvested and resected on day 8, and mass (wet weight) determined. Data shown is the mean±SD (N=8-12). The mass of the NB7C8 is significantly decreased (p<0.002).

To test the capacity of ScA to directly inhibit tumor growth in vivo, neuroblastoma tumors expressing (or lacking) caspase 8 were seeded into the chick chorioallantoic membrane, and a tumor mass allowed to establish for three days. Tumors were then treated topically with 100 picomoles of ScA, and allowed to grow a further five days before being harvested. In this case, we observed an inhibition of tumor growth selectively in the caspase 8-expressing tumor cells. The results show that, in addition to an antiangiogenic effect, low levels of ScA can also act to inhibit the growth of caspase 8-expressing tumor cells in vivo.

Discussion

This invention describes pro-apoptic, anticancer activity of Somocystinamide A (ScA) and ScA analogs. ScA is a lipopeptide derived from the cyanobacteria Lyngbya majuscule (25, 26). We show here that ScA selectively activates a caspase 8-dependent cell death pathway. Interestingly, apoptosis occurs among tumor lines which are normally resistant to treatment with death receptor agonists that act via caspase 8. This is of particular interest, as many tumors tend to maintain caspase 8 expression likely due to its ability to also fulfill non-apoptotic roles (10, 27), but are resistant to death receptor mediated killing (28). Other natural products, including the complex heterocycle gambogic acid (29) and the related kaurene diterpene (30), also activate caspase 8-dependent killing. Although gambogic acid is structurally unrelated to ScA and acts via distinct molecular pathways (29), the shared property of caspase 8 activation is interesting, and it is conceivable that such compounds could function as defensive adaptations (9).

ScA induces alterations in the plasma membrane lipid compartment, as indicated by clustering of ceramide on the cell surface associated with activation of caspase 8 and cell death. At micromolar concentrations, ScA can induce cell death via caspase 8—independent pathways, as shown by its capacity to induce apoptosis in caspase 8 deficient cells. This is in agreement with other lipid agents, such as ceramide, which can induce apoptosis via several different actions (19, 31). Nonetheless, the cytotoxic actions of ScA at nanomolar and picomolar concentrations are caspase 8-dependent. Our results group the cell lines examined into two categories; those that are sensitive in the lower nanomolar ranges, and those in which near micromolar and above concentrations are required to induce cell death (Table 1). All of the more sensitive lines can be killed by caspase 8-mediated pathways. However, we expect that metabolic pathways which regulate the lipid composition of the plasma membrane will also act as independent factors that can modulate cell sensitivity to ScA.

ScA contains a disulfide bond which is anticipated to be reduced upon exposure to the inner leaflet of the plasma membrane. However, noting that the invention is not limited by any particular mechanism of action, it is not yet clear whether covalent modification of membrane components by ScA is necessary to activate (or inactivate) ScA mediated killing. ScA does represent an uncommon structure among compounds isolated from marine cyanobacteria, containing a disulfide moiety and lipopeptide tails, and the cytotoxic activity of ScA requires both lipopeptide and disulfide moieties to initiate caspase 8-dependent death. Truncation of the lipopeptide, or reduction or substitution of the sulfhydryl bonds completely abrogated the cytocidal activity of ScA.

However, ScA integrated into nanosomes maintained full activity, suggesting an alternative mechanism for delivery in which ScA would be sequestered and protected within a hydrophobic environment (the invention provides nanosomes, including liposomes and other lipid delivery moieties, comprising a composition of this invention, e.g., ScA or an ScA analog of this invention). This may be particularly desirable for in vivo applications, based on the ability of liposomes to stabilize and provide a targeting function for ScA. For example, interchelation within nanosomes would be expected to protect the disulfide bond moiety from metabolic degradation following administration in vivo. Thus, in alternative embodiments for practicing the compositions and methods of this invention, nanosomes, including liposomes and other lipid delivery moieties, are used to delivery ScA and/or an ScA analog of this invention to cells in vitro, ex vivo and/or in vivo.

Synthesis of ScA involves known organic chemistry reactions, and can be accomplished via more than one approach. Alternative reaction schemes can be used to optimize yield and purity for large scale production. Storage of ScA in an inert dry atmosphere may be necessary to avoid hydrolytic degradation of its unsaturated amide, but the compound is otherwise quite stable. Similarly, the production of nanosomes of this invention can involve assembly from commercially available structural and targeting components, occurring in quantitative yields via standard liposome production techniques. ScA is an active natural compound which appears unencumbered by issues with complex sythesis or upscaling commonly associated with natural products.

The invention provides targetable nanoplatforms comprising compositions of this invention (e.g., ScA and ScA analogs of this invention); and these nanoplatforms, including nanosomes, liposomes and other lipid delivery moieties, of the invention can be designed to home to specific tumor or vascular beds, e.g., as described in (32). This therapeutic approach of this invention takes advantage of the limited solubility of ScA and analogs in aqueous media to act directly at the plasma membrane of susceptible and/or targeted cells. Toxic and relatively insoluble drugs, such as taxols, may be co-delivered with nanoplatform mediated delivery mechanisms of this invention.

While the invention is not limited by any particular mechanism of action, the ability of ScA to readily partition within the nanosome lipid component is advantageous for the targeted delivery of this compound to tumors. The targeted nanosome embodiments of this invention can overcome issues in terms of solubility and metabolism of ScA while in circulation in vivo. Drugs such as ScA do not compete for interior "cargo" space designated for soluble drug payloads. Thus, the lipid-based delivery embodiments of this invention can be an efficient design for the delivery of combination therapies. Given the sensitivity of proliferating endothelial cells to ScA and the ScA analogs of this invention, targeted delivery to cells of the vascular compartment will promote a potent and specific anti-angiogenic response.

Materials and Methods

Confocal microscopy. For confocal analysis A549 cells were seeded on glass coverslips, treated with ScA, DMSO or arachidonic acid (controls) at 1 or 0.1 uM concentration for 30 minutes or 6 hours. After treatment, the cells were fixed 10 minutes at room temperature with 4% PFA, washed twice with PBS, permeabilized 2 minutes at room temperature with 0.1% triton in PBS and blocked for 30 minutes with sterile 2% BSA in PBS. The staining was performed at room temperature for 2 hours (h), with mouse monoclonal anti-human ceramide (Alexis) and rabbit anti-human caspase 8 (BD Pharmingen) antibodies followed by secondary goat anti-mouse ALEXA FLUOR568™ and goat anti-rabbit ALEXA FLUOR488™ antibodies (Invitrogen). The blue DNA binding dye TOPRO-3™ (Molecular Probes) was added together with the secondary antibodies. The cells were washed three times with PBS between the different incubation steps and the incubation with the secondary fluorescently labeled antibodies was performed in the dark. All antibodies were diluted in PBS. Confocal images were recorded on a Nikon ECLIPSE C1™ confocal microscope.

Cell lines. Cells and cell lines were maintained in either DMEM or RPMI supplemented with 10% FCS. The caspase-deficient NB7 neuroblastoma cells have been previously described (33). C8-deficient and reconstituted jurkat cells were provided by Dr. Steve Hedrick (UCSD). Silencing of Caspase-8 gene expression in the A549 cells was performed through the use of delivering shRNA in a lentiviral format. Briefly 293 T cells were transfected with caspase-8, (Open Biosystems) or scrambled (Addgene) shRNAs in pLK0.1 lentiviral vector, together with lentiviral packaging plasmids (PMLDL, VSV-G and RSV-REV) using fugene6. The ratio of target ShRNAs and packaging plasmids was ShRNA/PMLDL/VSV-G/RSV-REV, 10/10/6/4 µg. Lentiviral supernatants from 293 T cells were harvested after 48 hours and used to infect A549 cells. Viral constructs were incubated for 24 h with A549 cell lines prior to replacing media with selective media containing puromycin (1 µg/ml). The suppression of caspase-8 was verified by western blot.

Cytotoxicity Assay. Cytotoxicity of ScA was assessed using the XTT cell proliferation assay. Briefly cells were plated on 96 well plates (5,000 per well) and incubated over night at 37° C. to allow for attachment and spreading. After 24 h, ScA was added from a DMSO stock, previously frozen at −80C as added directly from serial dilutions in DMSO at concentrations ranging from 100 uM to 100 fM. After 72 h, XTT (Aldrich Chemicals) was added to a final concentration of 250 ug/well. The plates were then incubated under standard tissue culture conditions until the control wells (DMSO) reached an OD value between 1.0-1.5. as measured at 450 nm using a microtiter plate reader. The cell viability-drug dilution profiles were obtained from sigma plots, and drug concentrations which inhibited growth by 50% were calculated from multiple runs. ($IC_{50}$)

Preparation of Liposomes. Cholesterol:Dope:Dspc:Sca:Dspe-Mpeg (in 1:1:1:0.16:0.16 molar ratio) in chloroform were taken in 30 mL glass culture tubes, dried under a stream of nitrogen gas and vacuum-dessicated for a minimum of 6 h to remove any residual organic solvent. The dried lipid film was hydrated in sterile deionized water in a total volume of 1 mL for a minimum of 12 h. Liposomes were vortexed for 2-3 minutes to remove any adhering lipid film and sonicated in a bath sonicator (ULTRASONIK 28X™) for 2-3 minutes at room temperature to produce multilamellar vesicles (MLV). MLVs were then sonicated with a Ti-probe (using a BRANSON450™ sonifier at 100% duty cycle and 25 W output power) in an ice bath for 1-2 minutes to produce small unilamellar vesicles (SUVs) as indicated by the formation of a clear translucent solution. The solution was pressure filtered in sequence though 200 and then 100 nm nucelopore polycarbonate membranes to obtain liposome nanoparticles of 100 nm with a polydispersity factor of less than 0.1.

Endothelial Cell Tube Formation. 96-well plates were coated with 200 uL matrigel per well and stored at 4° C. until use. HUVEC cells were harvested and cell suspensions were prepared at a density of 200,000/ml., and added at 100 ul per well to the plates. ScA in DMSO were added to each well at 10 nM 100 pM and 1 pM concentration with 1% DMSO as control. The plates were incubated at 37° C. under standard incubator conditions and the results were observed microcopically for tube formation.

Zebrafish Experiments. Blood vessel formation in Zebrafish: Transgenic Tg(fli1:EGFP) zebrafish embryos were purchased from www.zfin.org as reported elsewhere (34). Adult fish and embryos were maintained according to "Zebrafish—A Practical Approach" (35). ScA compound in DMSO stock solution was diluted directly into the water and zebrafish intersegmental vessels were imaged using Nikon c1-si confocal microscope after the times specified. Raw image datasets were processed using IMARIS 3D™ image analysis software. All animal procedures were conducted in accordance with all appropriate regulatory standards under protocol #S06008 approved by the University of California San Diego (UCSD) Institutional Animal Care and Use Committee.

Chick Chorioallantoic membrane studies. The CAM studies were performed using 10 day old chick embryos as we've previously described (36). For the tumor studies, $5 \times 10^6$ NB7 or NB7-C8 neuroblastoma tumor cells were seeded into the CAMs on 10 day old embryos and the tumor allowed to develop until day 18 (12).

Western blotting Cells were treated as indicated and extracts were prepared by lysis in RIPA buffer (100 mM Tris, pH7.5; 150 mM NaCl; 1 mM EDTA; 1% deoxycholate; 1% Triton X-100; 0.1% SDS; 50 mM NaF; COMPLETE PROTEASE INHIBITORT™, Boehringer Mannheim) on ice. Cell extracts (25 μg) were resolved by 8% SDS-PAGE, transferred to nitrocellulose and probed with antibodies. Caspase-8 was probed with polyclonal antibody from (Millipore) or affinity-purified catalytic domain-specific antisera ($C_{8-531}$) prepared at UCSD. Caspase-3 (Chemicon MAB4703, 1:500), caspase-9 (Santa Cruz Biotechnology sc17784, 1:100), actin (Sigma, 1:5000) and PARP (Santa Cruz Biotechnology sc556493, 1:500) were probed with mouse monoclonal antibodies. Bound antibodies were detected with horseradish peroxidase-conjugated secondary antibodies (BioRad) and the ECL system (Pierce).

FACS analysis Cell viability was analyzed by flow cytometry following propidium iodide (PI) staining, as described elsewhere (37). Briefly, after each treatment, cells were harvested in ice cold PBS, washed two times in PBS at 4° C. and resuspended in 10 μg/ml PI. The extent of apoptosis was determined by plotting PI fluorescence versus the forward scatter parameter, using CELL QUEST™ software.

References:
1. Monga, M. Sausville, E. A. (2002) Developmental therapeutics program at the NCI: molecular target and drug discovery process. *Leukemia* 16, 520-6.
2. Venter, J. C., Remington, K., Heidelberg, J. F., Halpern, A. L., Rusch, D., et al. (2004) Environmental genome shotgun sequencing of the Sargasso Sea. *Science* 304, 66-74.
3. Yooseph, S., Sutton, G., Rusch, D. B., Halpern, A. L., Williamson, S. J., et al. (2007) The Sorcerer II Global Ocean Sampling expedition: expanding the universe of protein families. *PLoS Biol* 5, e16.
4. Rusch, D. B., Halpern, A. L., Sutton, G., Heidelberg, K. B., Williamson, S., et al. (2007) The Sorcerer II Global Ocean Sampling expedition: northwest Atlantic through eastern tropical Pacific. *PLoS Biol* 5, e77.
5. Rao, P. V., Gupta, N., Bhaskar, A. S. Jayaraj, R. (2002) Toxins and bioactive compounds from cyanobacteria and their implications on human health. *J Environ Biol* 23, 215-24.
6. Kim, J., Park, E. J. (2002) Cytotoxic anticancer candidates from natural resources. *Curr Med Chem Anticancer Agents* 2, 485-537.
7. Shimizu, Y. (2003)Microalgal metabolites. *Curr Opin Microbiol* 6, 236-43.
8. Osborne, N. J., Webb, P. M., Shaw, G. R. (2001) The toxins of Lyngbya majuscula and their human and ecological health effects. *Environ Int* 27, 381-92.
9. Moore, R. E. (1996)Cyclic peptides and depsipeptides from cyanobacteria: a review. *J Ind Microbiol* 16, 134-43.
10. Barnhart, B. C., Legembre, P., Pietras, E., Bubici, C., Franzoso, G., et al. (2004) CD95 ligand induces motility and invasiveness of apoptosis-resistant tumor cells. *Embo J* 23, 3175-85.
11. Nogle, L. M., Gerwick, W. H. (2002) Somocystinamide A, a novel cytotoxic disulfide dimer from a Fijian marine cyanobacterial mixed assemblage. *Org Lett* 4, 1095-8.
12. Stupack, D. G., Teitz, T., Potter, M. D., Mikolon, D., Houghton, P. J., et al. (2006) Potentiation of neuroblastoma metastasis by loss of caspase-8. *Nature* 439, 95-9.
13. Peter, M. E., Krammer, P. H. (2003) The CD95(APO-1/Fas) DISC and beyond. *Cell Death Differ* 10, 26-35.
14. O'Donnell D. R., Milligan, L., Stark, J. M. (1999) Induction of CD95 (Fas) and apoptosis in respiratory epithelial cell cultures following respiratory syncytial virus infection. *Virology* 257, 198-207.
15. Muppidi, J. R., Siegel, R. M. (2004) Ligand-independent redistribution of Fas (CD95) into lipid rafts mediates clonotypic T cell death. *Nat Immunol* 5, 182-9.
16. Malorni, W., Giammarioli, A. M., Garofalo, T., Sorice, M. (2007) Dynamics of lipid raft components during lymphocyte apoptosis: The paradigmatic role of GD3. *Apoptosis* 12, 941-949.
17. Elyassaki, W., Wu, S. (2006) Lipid rafts mediate ultraviolet light-induced Fas aggregation in M624 melanoma cells. *Photochem Photobiol* 82, 787-92.
18. Perez-Lopez, M. E., Curiel, T., Gomez, J. G., Jorge, M. (2007) Role of pegylated liposomal doxorubicin (Caelyx) in the treatment of relapsing ovarian cancer. *Anticancer Drugs* 18, 611-7.

19. Rotolo, J. A., Zhang, J., Donepudi, M., Lee, H., Fuks, Z., et al. (2005) Caspase-dependent and -independent activation of acid sphingomyelinase signaling. *J Biol Chem* 280, 26425-34.
20. Erdreich-Epstein, A., Tran, L. B., Bowman, N. N., Wang, H., Cabot, M. C., et al. (2002) Ceramide signaling in fenretinide-induced endothelial cell apoptosis. *J Biol Chem* 277, 49531-7.
21. Erdreich-Epstein, A., Shimada, H., Groshen, S., Liu, M., Metelitsa, L. S., et al. (2000) Integrins alpha(v)beta3 and alpha(v)beta5 are expressed by endothelium of high-risk neuroblastoma and their inhibition is associated with increased endogenous ceramide. *Cancer Res* 60, 712-21.
22. Erdreich-Epstein, A., Tran, L. B., Cox, O. T., Huang, E. Y., Laug, W. E., et al. (2005) Endothelial apoptosis induced by inhibition of integrins alphavbeta3 and alphavbeta5 involves ceramide metabolic pathways. *Blood* 105, 4353-61.
23. Giovannoni, S., Stingl, U. (2007) The importance of culturing bacterioplankton in the 'omics' age. *Nat Rev Microbiol* 5, 820-6.
24. Giovannoni, S. J., Stingl, U. (2005) Molecular diversity and ecology of microbial plankton. *Nature* 437, 343-8.
25. Orsini, M. A., Pannell, L. K., Erickson, K. L. (2001) Polychlorinated acetamides from the cyanobacterium *Microcoleus lyngbyaceus*. *J Nat Prod* 64, 572-7.
26. Sims, J. K., Zandee van Rilland, R. D. (1981)Escharotic stomatitis caused by the "stinging seaweed" *Microcoleus lyngbyaceus* (formerly *Lyngbya majuscula*). Case report and literature review. *Hawaii Med J* 40, 243-8.
27. Helfer, B., Boswell, B. C., Finlay, D., Cipres, A., Vuori, K., et al. (2006)Caspase-8 promotes cell motility and calpain activity under nonapoptotic conditions. *Cancer Res* 66, 4273-8.
28. Schimmer, A. D., Thomas, M. P., Hurren, R., Gronda, M., Pellecchia, M., et al. (2006) Identification of small molecules that sensitize resistant tumor cells to tumor necrosis factor-family death receptors. *Cancer Res* 66, 2367-75.
29. Kasibhatla, S., Jessen, K. A., Maliartchouk, S., Wang, J. Y., English, N. M., et al. (2005) A role for transferrin receptor in triggering apoptosis when targeted with gambogic acid. *Proc Natl Acad Sci USA* 102, 12095-100.
30. Kondoh, M., Suzuki, I., Sato, M., Nagashima, F., Simizu, S., et al. (2004) Kaurene diterpene induces apoptosis in human leukemia cells partly through a caspase-8-dependent pathway. *J Pharmacol Exp Ther* 311, 115-22.
31. Santana, P., Pena, L. A., Haimovitz-Friedman, A., Martin, S., Green, D., et al. (1996) Acid sphingomyelinase-deficient human lymphoblasts and mice are defective in radiation-induced apoptosis. *Cell* 86, 189-99.
32. Torchilin, V. P. (2006) Multifunctional nanocarriers. *Adv Drug Deliv Rev* 58, 1532-55.
33. Teitz, T., Wei, T., Valentine, M. B., Vanin, E. F., Grenet, J., et al. (2000) Caspase 8 is deleted or silenced preferentially in childhood neuroblastomas with amplification of MYCN. *Nat Med* 6, 529-35.
34. Lawson, N. D., Weinstein, B. M. (2002) In vivo imaging of embryonic vascular development using transgenic zebrafish. *Dev Biol* 248, 307-18.
35. Nusslein-Volhard, C., Dahm, R. (2003) *Zebrafish* (Oxford University Press.
36. Storgard, C., Mikolon, D., Stupack, D. G. (2005) Angiogenesis assays in the chick CAM. *Methods Mol Biol* 294, 123-36.
37. Tones, V. A., Tapia, J. C., Rodriguez, D. A., Parraga, M., Lisboa, P., et al. (2006) Caveolin-1 controls cell proliferation and cell death by suppressing expression of the inhibitor of apoptosis protein survivin. *J Cell Sci* 119, 1812-23.

Example 8

Synthetic Schemes for Making Somocystinamide A Lipopeptide

Figure 32:
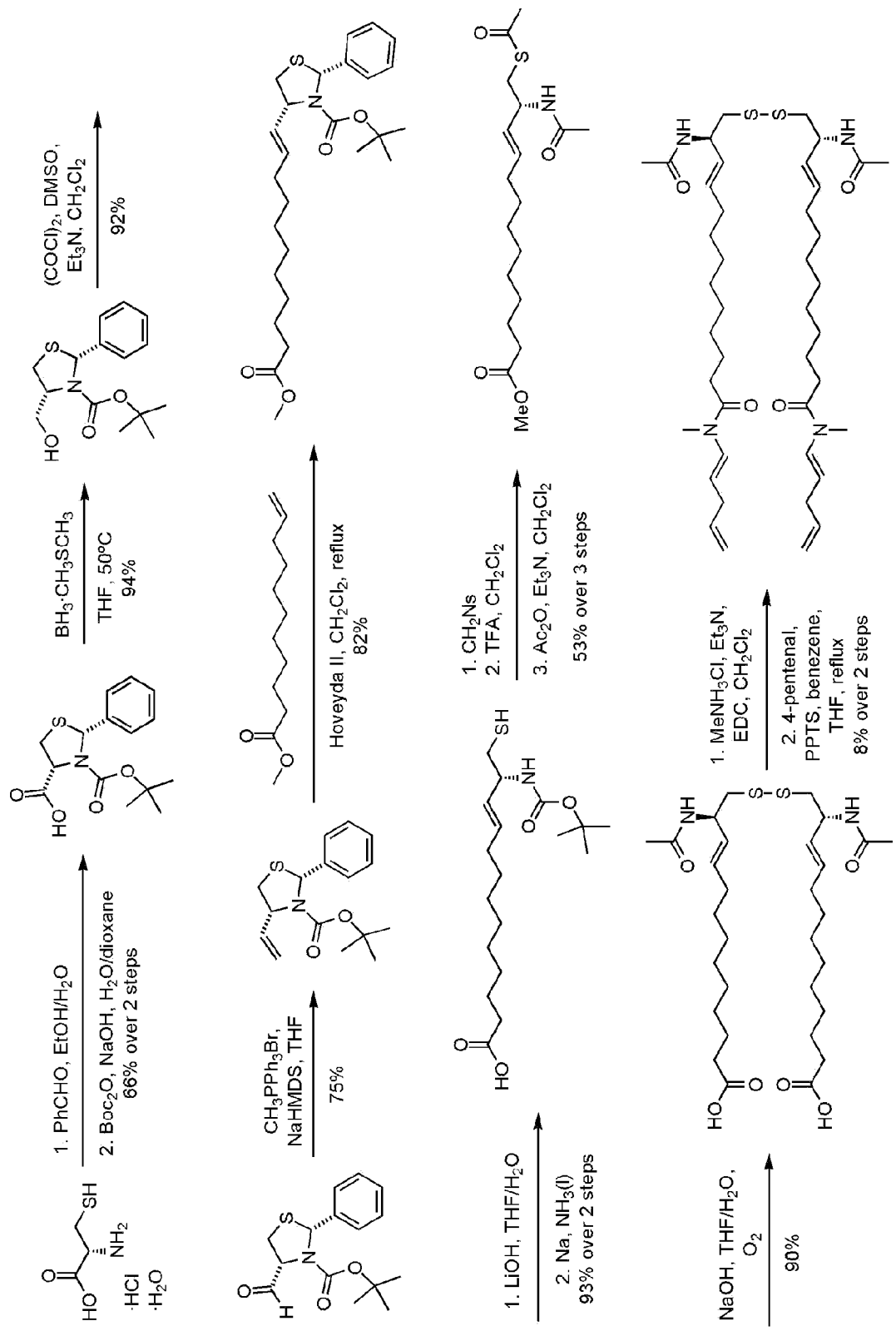
FIG. 32 illustrates an exemplary protocol of this invention for synthesize somocystinamide A.

Any protocol can be used to synthesize somocystinamide A to practice this invention; e.g., to synthesize somocystinamide A for use as a drug, or to synthesize somocystinamide A as an intermediate for further processing to make a compound of this invention. The invention provides a novel protocol of this invention for synthesize somocystinamide A, comprising the following synthetic scheme (see also FIG. 32):

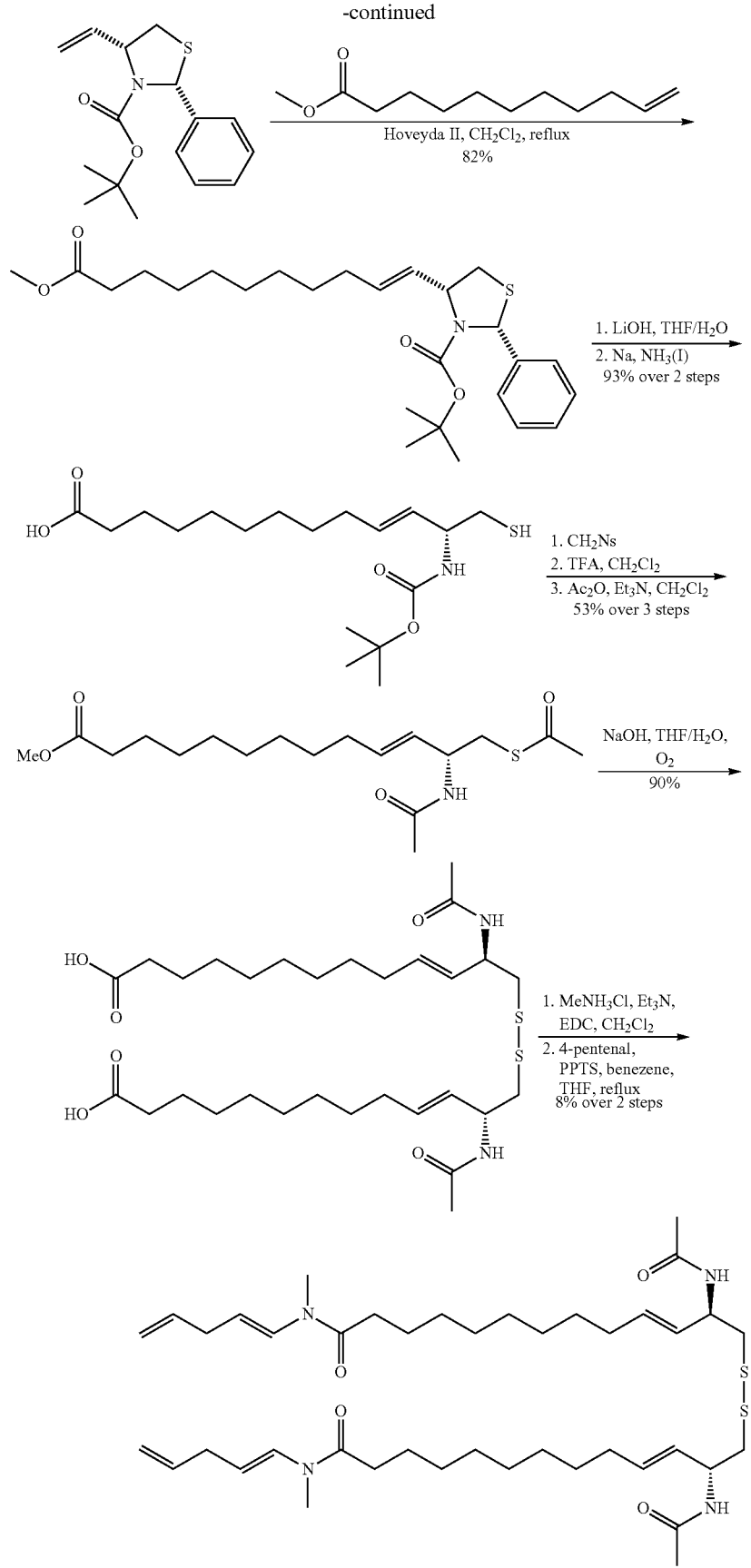

Example 9

Synthetic Schemes for Making Somocystinamide A Lipopeptides and Somocystinamide A Lipopeptide Analogs of the Invention This example describes an exemplary means synthetic protocol for the total synthesis of somocystinamide A.

Unless noted otherwise, all materials were purchased from commercial sources and were used without further purification. Anhydrous benzene was purchased from EMD. Tetrahydrofuran (THF) was distilled from sodium/benzophenone. Et$_3$N and CH$_2$Cl$_2$ were distilled from CaH. Ac$_2$O was distilled from quinone. Dimethyl sulfoxide (DMSO), oxalyl chloride, and trifluoroacetic acid (TFA) were distilled without desiccant. All reactions were carried out under dry argon atmosphere unless otherwise noted. Reaction temperatures herein recorded are external temperatures unless otherwise noted. Flash chromatography was performed using EMD silica gel (230-400 mesh). TLC was performed using EM Science pre-coated silica gel plates (Merck 60 F$_{254}$).

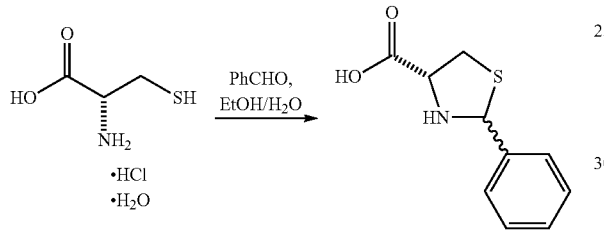

(R)-2-phenylthiazolidine-4-carboxylic acid. To the suspension of L-cysteine hydrochloride monohydrate (99.24 g, 565.1 mmol) in H$_2$O (535 mL) were added EtOH (420 mL) and benzaldehyde (83.1 mL, 818 mmol) under stirring. After a few minutes, the mixture became a thick cream, which could not be stirred. Enough H$_2$O/EtOH (3:2) solution was added to assist in stirring the mixture. After 2.5 hrs, the mixture was filtered and the solid was washed with H$_2$O and hexane successively. Upon drying under high vacuum, white powder (121.19 g) was obtained, which was used in the next step without further purification.

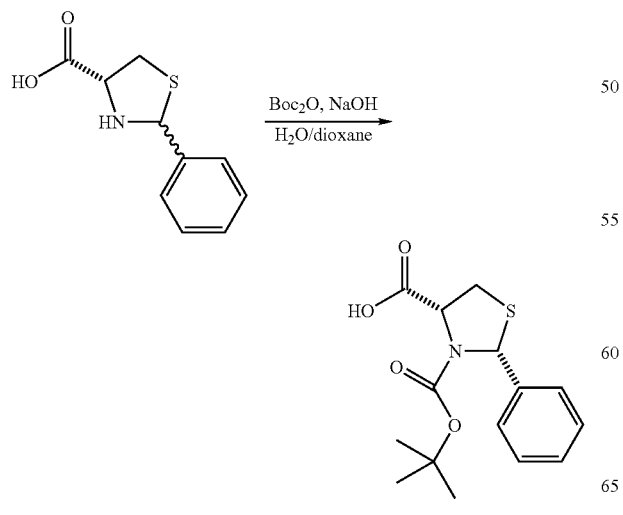

(2R,4R)-3-(tert-butoxycarbonyl)-2-phenylthiazolidine-4-carboxylic acid. The suspension of the thiazolidine (63.10 g, from the previous step) in 1,4-dioxane (520 mL) was cooled to 0° C. while stirring. Then H$_2$O (260 mL) and 1M NaOH solution (260 mL) were added successively. Subsequently, Boc$_2$O (73.87 g, 338.5 mmol) was added in one portion. The solution was stirred and was kept at 0° C. for 30 min. Then approximately half of the solvents were removed under vacuum. Enough 1% H$_2$SO$_4$ solution was added to bring the pH to ~2. The mixture was extracted with EtAcO (400 mL×4). The combined organic layer was dried over MgSO$_4$. Upon filtration, most of the solvents were removed and the mixture was triturated with hexane to obtain white powder (79.89 g, 258.2 mmol, 86% over 2 steps).

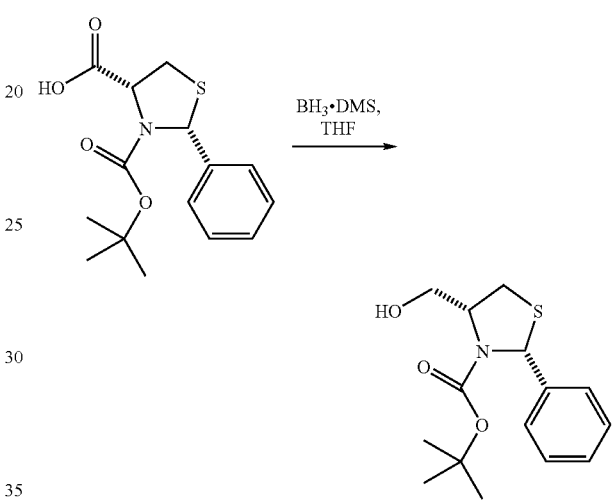

(2R,4R)-tert-butyl 4-(hydroxymethyl)-2-phenylthiazolidine-3-carboxylate. To the suspension of the carboxylic acid (62.03 g, 200.5 mmol) in THF (100 mL) was added 2M BH$_3$·S(CH$_3$)$_2$ in THF (200 mL, 400 mmol) dropwise at rt. The mixture was warmed and was stirred at 45~50° C. for 16 hrs and it became a clear colorless solution. After cooling to rt, the reaction mixture was carefully poured into a mixture of crushed ice and water (~500 mL). Enough of the mixture of 1M NaOH solution and 10% H$_2$SO$_4$ solution (1:1, ~25 mL) was added to bring the pH to 2. The aqueous layer was extracted with Et$_2$O (250 mL×4). The combined organic layer was washed with H$_2$O (100 mL), saturated NaHCO$_3$ solution (100 mL), and brine (100 mL) and was dried over MgSO$_4$. Upon filtration, the solvents were removed in vacuo to obtain a colorless glass (54.75 g, 185.3 mmol, 92% yield), which was pure by TLC analysis and was used in the next step without further purification. TLC Rf=0.34 EtAcO/hexane (1:2).

-continued

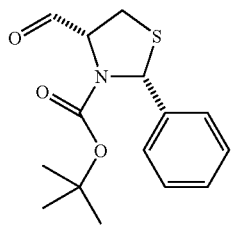

(2R,4R)-tert-butyl 4-formyl-2-phenylthiazolidine-3-carboxylate. To the solution of oxalyl chloride (3.26 mL, 38.5 mmol) in CH$_2$Cl$_2$ (150 mL) at −70° C. was added a solution of DMSO (6.58 mL, 92.6 mmol) in CH$_2$Cl$_2$ (40 mL) dropwise over 15 min while stiffing, during which evolution of gases was observed. After 10 min of stirring the solution at −70° C., the solution of the alcohol (10.25 g, 34.70 mmol) in CH$_2$Cl$_2$ (45 mL) was added dropwise over 15 min. The solution was stirred and kept at −65~−70° C. for 60 min. Then Et$_3$N (24.2 mL, 17.4 mmol) was added at −70° C. under stiffing, after which the reaction mixture turned pale pink. After keeping the mixture at −65° C. for 10 min, it was taken out of the dry ice bath and warmed to rt. Then the mixture was poured into an ice-cold 0.5 M KHSO$_4$ aqueous solution (150 mL). The aqueous layer was still basic and enough 10% H$_2$SO$_4$ solution was added to lower the pH to 2. The aqueous layer was extracted with CH$_2$Cl$_2$ (100 mL×2). The combined organic layer was washed with brine (100 mL) and was dried over MgSO$_4$. Filtration and removal of solvents yielded yellow gummy oil (9.866 g, 33.62 mmol, 97% yield), which solidified upon standing in a freezer.

(2R,4R)-2-phenyl-4-vinylthiazolidine-3-tert-butyl carboxylate. To the suspension of MePPh$_3$.Br (13.37 g, 37.43 mmol) in THF (150 mL) at −78° C. (dry ice bath) was added 1.0 M NaHMDS (43 mL, 43 mmol) dropwise under vigorous stiffing, which resulted in a yellow solution. The dry ice bath was removed and the solution stirred for 45 min at rt. The solution was cooled again to −78° C. and a solution of the aldehyde (8.302 g, 28.30 mmol) in THF (100 mL) was added dropwise. Then the solution was warmed to rt over night under stirring. Consumption of the aldehyde was confirmed by TLC analysis. Then 1.0 M aqueous NH$_4$Cl (100 mL) and Et$_2$O (100 mL) were added successively. The aqueous phase was extracted with Et$_2$O (100 mL×2). The combined organic phase was washed with brine, dried over Na$_2$SO$_4$, and was filtered through a plug of silica gel. Upon evaporation of solvents, the residue was purified by flash column chromatography (3:97 to 1:9 Et$_2$O/hexane) and a white solid (6.04 g, 20.7 mmol) was obtained (74% yield).

(2R,4R)-3-tert-butoxycarbonyl-4-((E)-11-methoxy-11-oxoundec-1-enyl)-2-phenylthiazolidine- To the solution of the thiazolidine olefin (5.500 g, 18.87 mmol) in CH$_2$Cl$_2$ (95 mL) was added methyl undecenoate (9.2 mL, 41 mmol) at rt. The solution was then subjected to vacuum-sonication-Ar introduction cycle three times for degassing. Then second generation Hoveyda-Grubbs catalyst (592 mg, 0.944 mmol) was addedin one portion. After 20 min of stirring at rt, the solution was refluxed for 16 hrs. Then the solvents were removed under vacuum and the residue was subjected to flash column chromatography (hexane to 1:9 Et$_2$O/ hexane) to obtain colorless oil (7.174 g, 15.54 mmol, 82% yield). Along with the desired product was isolated the cis isomer (TLC Rf=0.52 Et$_2$O/ hexane 3:7, 539 mg, 1.17 mmol, 6% yield). TLC Rf 0.47 Et$_2$O/hexane (3:7).

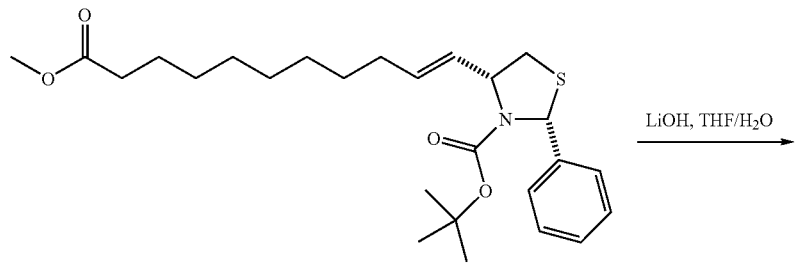

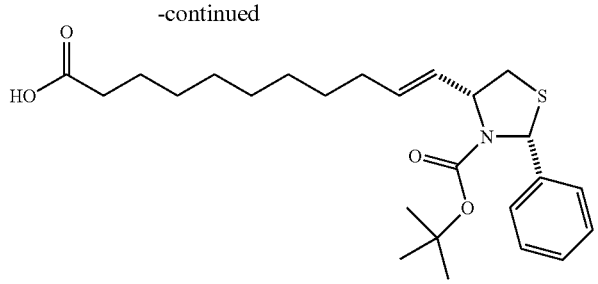

(E)-11-((2R,4R)-3-(tert-butoxycarbonyl)-2-phenylthiazolidin-4-yl)undec-10-enoic acid. The solution of the methyl ester (11.40 g, 24.70 mmol) in THF (240 mL) was cooled to 0° C. A solution of LiOH.H$_2$O (10.07 g, 240.2 mmol) in H$_2$O (120 mL) was added in one portion. Then the reaction mixture was stirred and warmed gradually over night to rt. Upon seeing some intact starting material on TLC, MeOH (25 mL) was added at rt. 6 hrs later, the solution was cooled to 0° C. and Et$_2$O (200 mL) and 1M NaHSO$_4$ solution (300 mL) were added, after which the pH was ca 2~3. Upon phase separation, the aqueous layer was extracted with Et$_2$O (150 mL×3). The combined organic layer was washed with brine (250 mL), dried over MgSO$_4$, and was filtered. Upon removal of the solvents, a gummy oil (11.27 g) was obtained, which was used in the next step without further purification.

The carboxylic acid (8.030g, from the previous step) was dissolved in Et$_2$O (50 mL) and was cooled to 0° C. Ethereal solution of CH$_2$N$_2$ (0.14 M, 170 mL, 24 mmol) was added dropwise over 30 min. Then N$_2$ was bubbled in for 45 min to remove excess CH$_2$N$_2$. Upon removal of the solvent in vacuo, white crystals were obtained (8.74 g). The crystals were dissolved in CH$_2$Cl$_2$ (200 mL) and was cooled to 0° C. Then TFA (50 mL) was added dropwise over 30 min. Upon further stiffing at 0° C. for 30 min, the volatiles were removed in vacuo to yield orange oil. Residual TFA was removed under hi-vacuum for 1 hr. This TFA salt was dissolved in CH$_2$Cl$_2$ (220 mL) and the solution was cooled to 0° C. Then Et$_3$N (30.6 mL, 220 mmol) and Ac$_2$O (10.4 mL, 110 mmol) were added slowly under stirring. The solution was let warm to rt over night under stirring. Then the volatiles were removed in vacuo. The residues were dissolved in Et$_2$O (200 mL) and 0.5

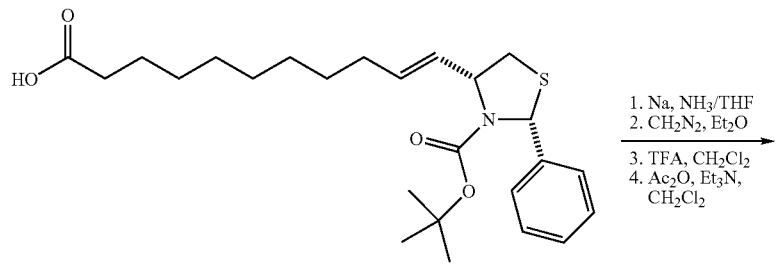

1. Na, NH$_3$/THF
2. CH$_2$N$_2$, Et$_2$O
3. TFA, CH$_2$Cl$_2$
4. Ac$_2$O, Et$_3$N, CH$_2$Cl$_2$

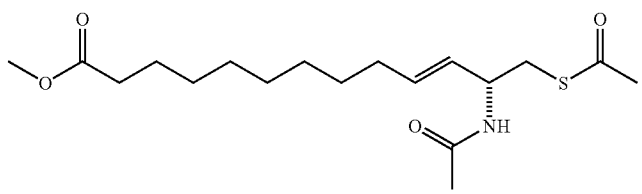

(R,E)-methyl 12-acetamido-13-(acetylthio)tridec-10-enoate. To the solution of the thiazolidine (11.145 g from the previous step) in THF (10 mL) was added NH$_3$(l) (350 mL) that was distilled over Na. To this mixture was added cubic pieces (5~7 mm) of Na under vigorous stiffing until dark blue color persisted. The mixture was kept refluxing at rt and Na pieces were added as necessary to keep the color for a total of 2 hrs. Then NH$_4$Cl was carefully added until the color disappeared. NH$_3$ was removed under gentle stream of N$_2$ to obtain a colorless oil (8.260g).

M HCl solution (200 mL) was added. Upon phase separation, the aqueous phase was extracted with Et$_2$O (200 mL×2). The combined organic phase was washed with H$_2$O (150 mL), saturated NaHCO$_3$ solution (100 mL), H$_2$O (100 mL), and brine (100 mL) successively. After flash column chromatography (15:85 EtAcO/hexane to 1:1 EtAcO/hexane), the desired product was obtained as a white solid (~4.2 g, 12 mmol, 50% yield over 5 steps). The disulfide methyl ester was also isolated as a colorless oil (173 mg, 0.275 mmol, 1% yield).

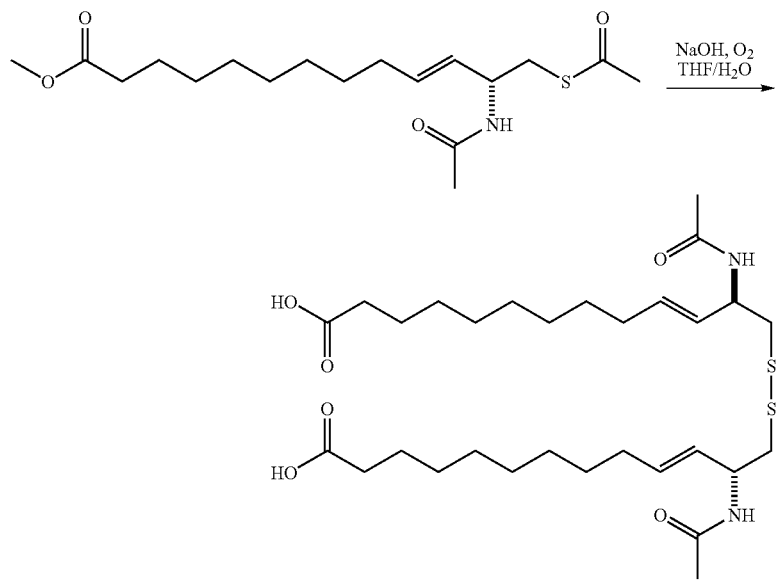

Somocystinoic acid. To the solution of the methyl ester (487 mg, 1.36 mmol) in THF (40 mL) was added 1M NaOH solution (20 mL) at rt under stirring. O₂ was continuously bubbled into the mixture while stirring at rt until the consumption of the thiol was observed by TLC (20 hrs). The reaction mixture was diluted with Et₂O (30 mL) and 1M KHSO₄ solution (40 mL) was added at 0° C. Upon phase separation, the aqueous layer was extracted with Et₂O (30 mL) and EtAcO (30 mL×2). The combined organic layer was dried over MgSO₄ and was filtered. Removal of the solvents in vacuo yielded pale yellow oil (463 mg), which was used without further purification for the next step.

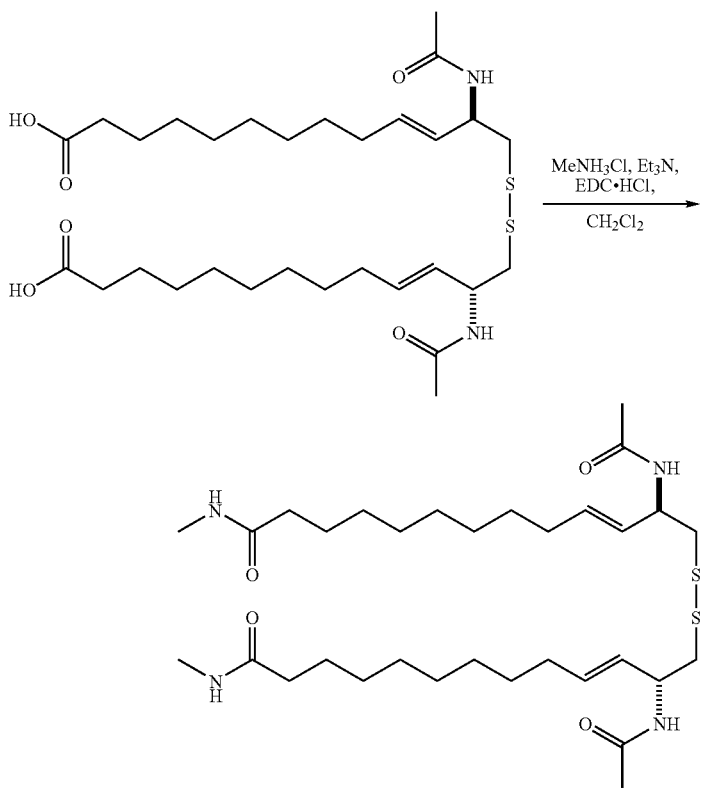

Somocystinoic acid N,N-dimethyl amide. To the suspension of somocystinoic acid (72 mg, 0.1198 mmol) in CH₂Cl₂ (8 mL) was added MeNH₃Cl (24 mg, 0.36 mmol), Et₃N (84 µL, 0.60 mmol), and EDC.HCl (50 mg, 0.26 mmol), and DMAP (5 mg) successively at 0° C. under stirring. The reaction was immediately warmed to rt and was stirred at rt for 5 hrs. After 3 hrs into the reaction, white precipitates appeared. The solvents were removed under vacuum. The residues were taken up in CH$_2$Cl$_2$/MeOH (2:1) and the mixture was washed with saturated NaHCO$_3$ solution and was dried over Na$_2$SO$_4$. Upon removal of the solvents, sufficiently pure material for the next step was obtained as a white solid (52 mg, 0.083 mmol, 69% yield over 2 steps).

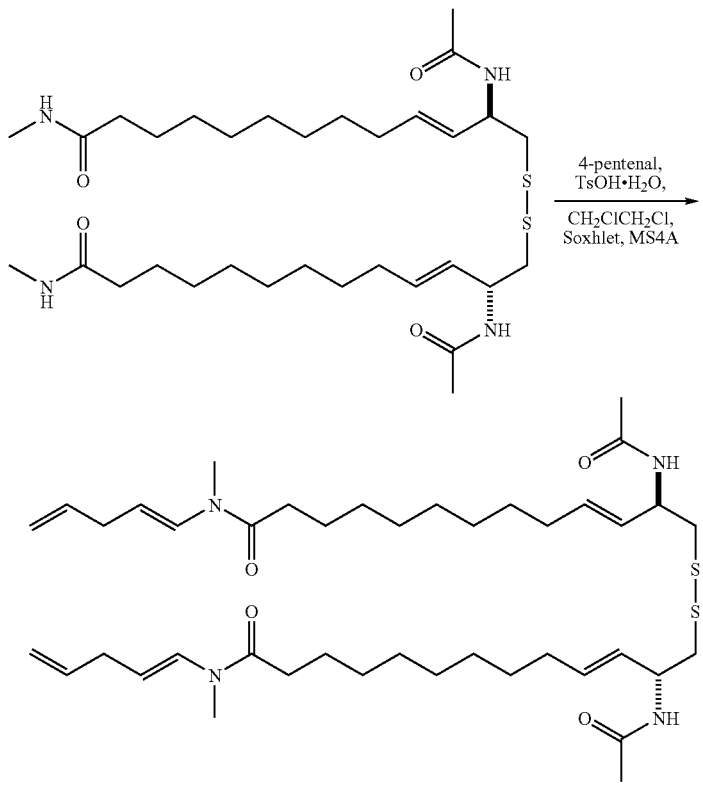

Somocystinamide A. The suspension of the methyl amide (12.8 mg, 0.0204 mmol) in 1,2-dichloroethane (25 mL) was degassed three times by vacuum-sonication-Ar introduction cycle. Then 4-pentenal (20 µL, 0.203 mmol) and TsOH.H$_2$O (1 mg, 0.005 mmol) were added successively at rt. The reaction mixture was refluxed over night under stirring in a Soxhlet apparatus that is equipped with glass wool and molecular sieves 4 Å so as to remove residual H$_2$O. After cooling to 0° C., Et$_3$N (50 µL) was added and the solution was diluted with CH$_2$Cl$_2$ (10 mL) and H$_2$O (20 mL). The aqueous layer was extracted with CH$_2$Cl$_2$ (20 mL×3). The combined organic layer was dried over Na$_2$SO$_4$. Upon filtration and removal solvents in vacuo, the residues were subjected to flash column chromatography (EtAcO to 1:1:8 MeOH/CH$_2$Cl$_2$/EtAcO) to obtain somocystinamide A (3.7 mg, 0.0049 mmol, 24% yield) as an off-white amorphous solid.

In an alternative aspect, the invention provides a method for synthesizing Somocystinamide A comprising:

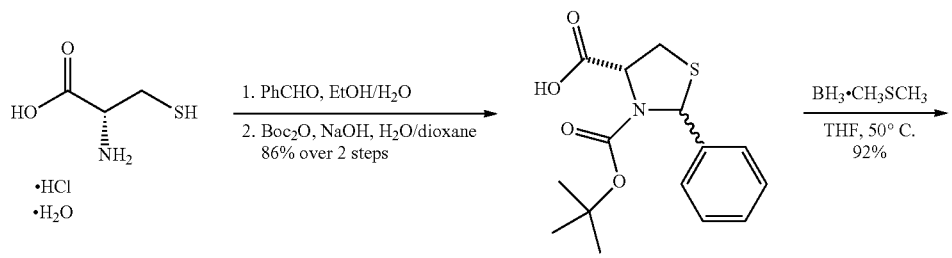

-continued
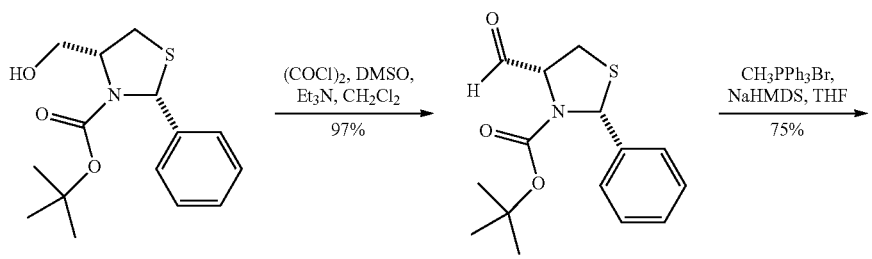
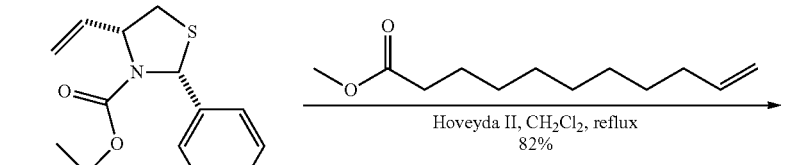
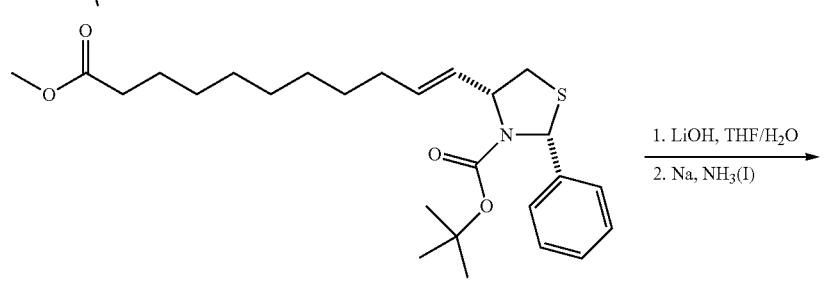
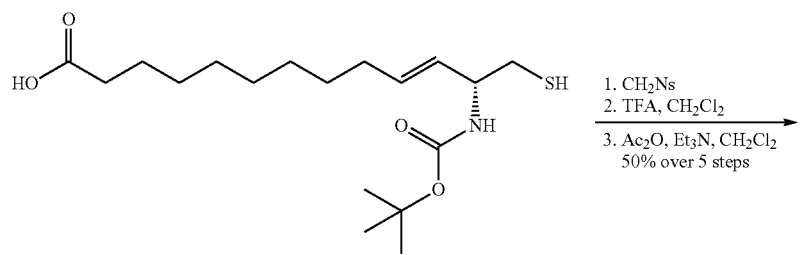
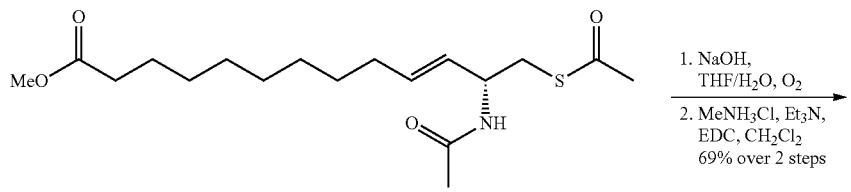
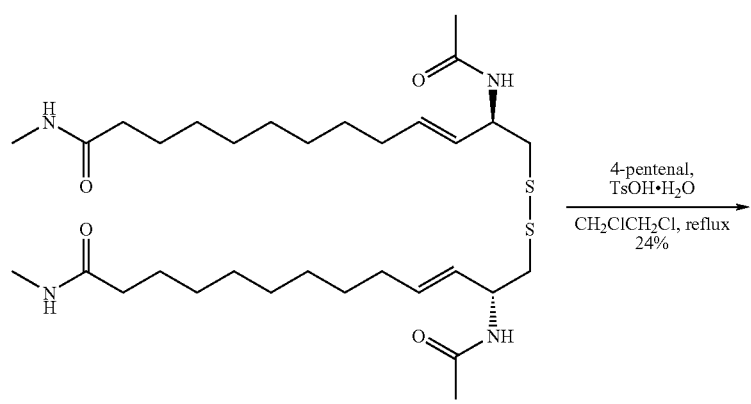

-continued

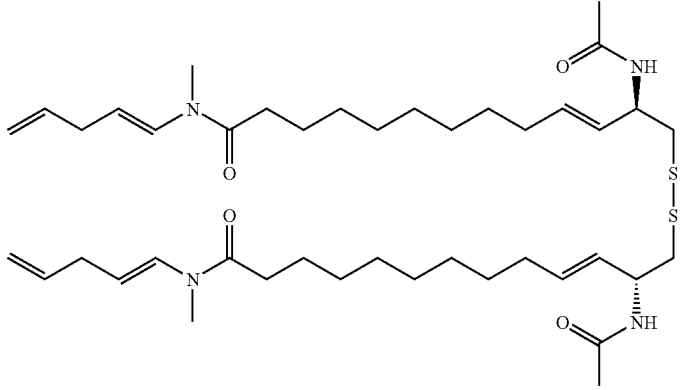

Accordingly, the invention provides a synthetic scheme for synthesizing somocystinamide A, as described above. The invention provides a synthetic scheme for synthesizing somocystinoic acid N,N-dimethyl amide, as described above. The invention provides a synthetic scheme for synthesizing somocystinoic acid, as described above. The invention provides a synthetic scheme for synthesizing (R,E)-methyl 12-acetamido-13-(acetylthio)tridec-10-enoate, as described above. The invention provides a synthetic scheme for synthesizing (E)-11-((2R,4R)-3-(tert-butoxycarbonyl)-2-phenylthiazolidin-4-yl)undec-10-enoic acid, as described above. The invention provides a synthetic scheme for synthesizing (2R,4R)-3-tert-butoxycarbonyl-4-((E)-11-methoxy-11-oxoundec-1-enyl)-2-phenylthiazolidine, as described above. The invention provides a synthetic scheme for synthesizing (2R,4R)-tert-butyl 4-(hydroxymethyl)-2-phenylthiazolidine-3-carboxylate, as described above. The invention provides a synthetic scheme for synthesizing (2R,4R)-3-(tert-butoxycarbonyl)-2-phenylthiazolidine-4-carboxylic acid, as described above.

A number of embodiments of the invention have been described. Nevertheless, it will be understood that various modifications may be made without departing from the spirit and scope of the invention. Accordingly, other embodiments are within the scope of the following claims.

The invention claimed is:
1. A method for killing a melanoma cancer cell comprising:
contacting the melanoma cancer cell with a somocystinamide A.
2. The method of claim 1, wherein the melanoma cancer cell is a cutaneous or intraocular melanoma cell.
3. The method of claim 1, wherein the somocystinamide A is formulated as a nanoparticle, or a liposomal nanoparticle.
4. The method of claim 1, wherein the somocystinamide A is formulated as a liposome or a multilayered liposome.
5. The method of claim 4, wherein the liposome is about 100 nM in size.
6. The method of claim 1, wherein the somocystinamide A, is administered with compound selected from the group consisting of: a thrombospondin, an angiostatin 5, a pigment epithelium-derived factor, an angiotensin, a laminin peptide, a fibronectin peptide, a plasminogen activator inhibitor, a tissue metalloproteinase inhibitor, an interferon, an interleukin 12, a platelet factor 4, an IP-10, a Gro-β, a thrombospondin, a 2-methoxyoestradiol, a proliferin-related protein, a carboxiamidotriazole, a marimastat, a pentosan polysulphate, an angiopoietin 2, an interferon-alpha, a herbimycin A, a sulfonated distamycin A derivative, a 16K prolactin fragment, a linomide, a thalidomide, a pentoxifylline, a genistein, a TNP-470, an endostatin, a paclitaxel, a docetaxel, a polyamine, a proteasome inhibitor, a kinase inhibitor, a signaling peptide, an accutin, a cidofovir, a vincristine, a bleomycin, a platelet factor 4, a minocycline, a 1,2-dithiol-3-thione, and any combination thereof.
7. The method of claim 1, wherein the somocystinamide A is formulated as a pharmaceutical composition, or is formulated with a pharmaceutically acceptable carrier.
8. The method of claim 7, wherein the pharmaceutical composition is administered parenterally, topically, orally, by local administration, by aerosol or transdermally.
9. The method of claim 7, wherein the pharmaceutical composition is formulated for human or veterinary use.
10. The method of claim 7, wherein the pharmaceutical composition is formulated in a unit dosage form.
11. The method of claim 10, wherein the unit dosage form comprises a tablet, a pill, a powder, a dragee, a capsule, a liquid, a lozenge, a soft sealed capsule, a gel, a syrup, a slurry, an aerosol or a suspension.
12. The method of claim 7, wherein the pharmaceutical composition is formulated as an aqueous suspension or an oil-based suspension, a liquid, a powder, an emulsion, a lyophilized powder, a spray, a cream, a lotion, a controlled release formulation, a tablets, a pill, a gel, on patch, or in an implant.
13. The method of claim 7, wherein the pharmaceutical composition is administered topically by applicator stick, solution, suspension, emulsion, gel, cream, ointment, paste, jelly, paint, powder or aerosol.
14. A method for treating, ameliorating, or slowing the progression of, a melanoma in an individual in need thereof, comprising administering a pharmaceutical composition comprising a somocystinamide A.
15. The method of claim 14, wherein the somocystinamide A is formulated as a liposome or a multilayered liposome.
16. The method of claim 14, wherein the somocystinamide A, is administered with compound selected from the group consisting of: a thrombospondin, an angiostatin 5, a pigment epithelium-derived factor, an angiotensin, a laminin peptide, a fibronectin peptide, a plasminogen activator inhibitor, a tissue metalloproteinase inhibitor, an interferon, an interleukin 12, a platelet factor 4, an IP-10, a Gro-β, a thrombospondin, a 2-methoxyoestradiol, a proliferin-related protein, a carboxiamidotriazole, a marimastat, a pentosan polysulphate, an angiopoietin 2, an interferon-alpha, a herbimycin A, a sulfonated distamycin A derivative, a 16K prolactin fragment, a linomide, a thalidomide, a pentoxifylline, a genistein, a TNP-

470, an endostatin, a paclitaxel, a docetaxel, a polyamine, a proteasome inhibitor, a kinase inhibitor, a signaling peptide, an accutin, a cidofovir, a vincristine, a bleomycin, a platelet factor 4, a minocycline, a 1,2-dithiol-3-thione, and any combination thereof.

17. The method of claim 14, wherein the pharmaceutical composition is administered parenterally, topically, orally, by local administration, by aerosol or transdermally.

18. The method of claim 17, wherein the pharmaceutical composition is administered topically by applicator stick, solution, suspension, emulsion, gel, cream, ointment, paste, jelly, paint, powder or aerosol.

19. The method of claim 14, wherein the pharmaceutical composition is formulated as an aqueous suspension or an oil-based suspension, a liquid, a powder, an emulsion, a lyophilized powder, a spray, a cream, a lotion, a controlled release formulation, a tablets, a pill, a gel, on patch, or in an implant.

20. The method of claim 14, wherein the pharmaceutical composition is formulated for human or veterinary use.

* * * * *